United States Patent [19]

Matsumoto

[11] Patent Number: 5,650,525
[45] Date of Patent: Jul. 22, 1997

[54] 1,2-DIOXETANE DERIVATIVES, INTERMEDIATES FOR SYNTHESES THEREOF AND METHODS OF PRODUCING THE INTERMEDIATES

[76] Inventor: Masakatsu Matsumoto, 8-1-509, Araisono 4-chome, Sagamihara-shi, Kanagawa-ken, Japan

[21] Appl. No.: 403,212

[22] Filed: Mar. 13, 1995

[30]  Foreign Application Priority Data

| Mar. 11, 1994 | [JP] | Japan | 6-067801 |
| Mar. 11, 1994 | [JP] | Japan | 6-067802 |
| Jul. 12, 1994 | [JP] | Japan | 6-181926 |
| Sep. 29, 1994 | [JP] | Japan | 6-259066 |
| Oct. 21, 1994 | [JP] | Japan | 6-281511 |

[51] Int. Cl.$^6$ ............................................ C07D 305/14
[52] U.S. Cl. ................................................... 549/510
[58] Field of Search .................................... 549/510

[56]  References Cited

U.S. PATENT DOCUMENTS 5,112,960  5/1992  Bronstein et al. .................. 536/18.1

FOREIGN PATENT DOCUMENTS 0254051  1/1988  European Pat. Off. .
WO8906226  7/1989  WIPO .

OTHER PUBLICATIONS

Matsumoto et al, "J. Chem. Soc., Chem. Comm.", vol. 21, pp. 2449–2450, 1994.

*Primary Examiner*—Ba K. Trinh
*Attorney, Agent, or Firm*—Cooper & Dunham LLP

[57]  ABSTRACT

A chemiluminescent 1,2-dioxetane derivative having a formula (I):

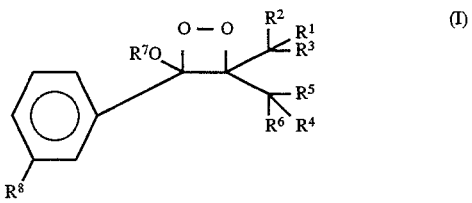

wherein $R^1$ and $R^4$ each represent, individually, hydrogen, an alkyl group, an alkoxyl group, a hydroxyl group, or $-OSi(R^9R^{10}R^{11})$ in which $R^9$, $R^{10}$ and $R^{11}$ each represent an alkyl group; $R^2$, $R^3$, $R^5$ and $R^6$ each represent, individually, hydrogen or an alkyl group, provided that $R^2$, $R^3$, $R^5$ and $R^6$ each cannot be hydrogen at the same time, and that $R^2$ and $R^3$, and $R^5$ and $R^6$, each taken together, can form a cycloalkyl group; $R^7$ represents an alkyl group; $R^8$ represents hydrogen, an alkoxyl group, a phosphate salt group, or $-OSi(R^9R^{10}R^{11})$; intermediates for synthesizing the above 1,2-dioxetane derivative; and methods of producing the intermediates are provided.

4 Claims, 2 Drawing Sheets

1,2-DIOXETANE DERIVATIVES, INTERMEDIATES FOR SYNTHESES THEREOF AND METHODS OF PRODUCING THE INTERMEDIATES

BACKGROUND OF THE INVENTION

1. Field of the Invention

The present invention relates to 1,2-dioxetane derivatives which can be used, for instance, as chemiluminescent reagents for immunoassays, and also to intermediates for the syntheses of the 1,2-dioxetane derivatives. The present invention further relates to methods of producing the intermediates.

2. Discussion of Background

Conventionally, varieties of 1,2-dioxetane compounds have been synthesized, and in particular, 1,2-dioxetane compounds substituted with a spiroadamantyl group at the 3 positions thereof are known to be useful as chemiluminescent substrates, for instance, as disclosed in Japanese Patent Publications 5-21918 and 5-45590.

However, it cannot be said that such conventional 1,2-dioxetane compounds are sufficiently thermally stable and have a chemiluminescence with sufficiently high intensity for use in practice, so that an improved chemiluminescent compound has been desired.

SUMMARY OF THE INVENTION

It is therefore a first object of the present invention to provide a chemiluminescent 1,2-dioxetane derivative which is thermally more stable and has a chemiluminescence with higher intensity.

A second object of the present invention is to provide intermediates for the synthesis of the 1,2-dioxetane derivative.

A third object of the present invention is to provide methods of producing the intermediates.

The first object of the present invention can be achieved by a 1,2-dioxetane derivative of formula (I):

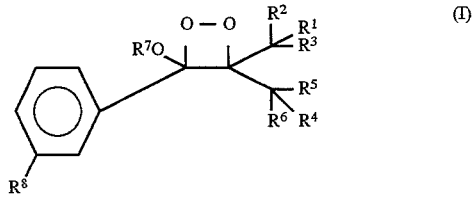

wherein $R^1$ and $R^4$ each represent, individually, hydrogen, an alkyl group, an alkoxyl group, a hydroxyl group, or $-OSi(R^9R^{10}R^{11})$ in which $R^9$, $R^{10}$ and $R^{11}$ each represent an alkyl group; $R^2$, $R^3$, $R^5$ and $R^6$ each represent, individually, hydrogen or an alkyl group, provided that $R^2$, $R^3$, $R^5$ and $R^6$ each cannot be hydrogen at the same time, and that $R^2$ and $R^3$, and $R^5$ and $R^6$, each taken together, can form a cycloalkyl group; $R^7$ represents an alkyl group; $R^8$ represents hydrogen, an alkoxyl group, a phosphate group, a phosphate salt group, or $-OSi(R^9R^{10}R^{11})$.

The second object of the present invention can be achieved by a compound of formula (II):

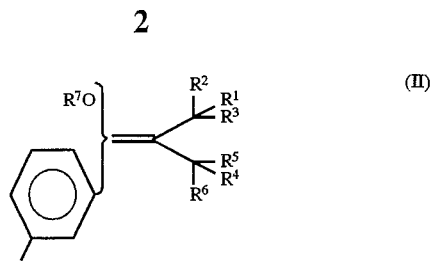

wherein $R^1$ and $R^4$ each represent, individually, hydrogen, an alkyl group, an alkoxyl group, a hydroxyl group, or $-OSi(R^9R^{10}R^{11})$ in which $R^9$, $R^{10}$ and $R^{11}$ each represent an alkyl group; $R^2$, $R^3$, $R^5$ and $R^6$ each represent, individually, hydrogen or an alkyl group, provided that $R^2$, $R^3$, $R^5$ and $R^6$ each cannot be hydrogen at the same time, and that $R^2$ and $R^3$, and $R^5$ and $R^6$, each taken together, can form a cycloalkyl group; $R^7$ represents an alkyl group; $R^{28}$ represents hydrogen, a hydroxyl group, an alkoxyl group, a phosphate group, a phosphate salt group, or $-OSi(R^9R^{10}R^{11})$ in which $R^9$, $R^{10}$ and $R^{11}$ each represent an alkyl group.

The second object of the present invention can also be achieved by a compound of formula (III):

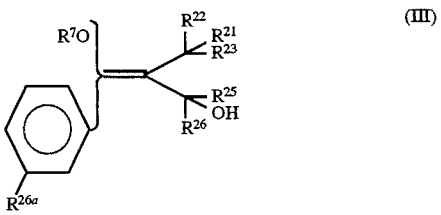

wherein $R^{21}$ represents hydrogen, a hydroxyl group or an alkyl group; $R^{22}$, $R^{23}$, $R^{25}$ and $R^{26}$ each represent, individually, hydrogen or an alkyl group, provided that $R^{21}$, $R^{22}$, $R^{23}$, $R^{25}$ and $R^{26}$ cannot be hydrogen at the same time and that any of two selected from the group consisting of $R^{21}$, $R^{22}$ and $R^{23}$, taken together, can form a cycloalkyl group; $R^7$ represents an alkyl group; and $R^{28a}$ represents hyrogen, an alkoxyl group, or $-OSi(R^9R^{10}R^{11})$ in which $R^9$, $R^{10}$ and $R^{11}$ each represent an alkyl group.

The second object of the present invention can also be achieved by a compound of formula (IVa):

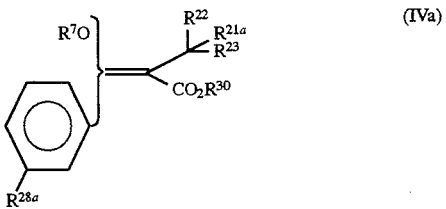

wherein $R^{21a}$, $R^{22}$ and $R^{23}$ each represent, individually, hydrogen or an alkyl group, provided that any of two selected from the group consisting of $R^{21a}$, $R^{22}$ and $R^{23}$, taken together, can form a cycloalkyl group; $R^7$ represents an alkyl group; and $R^{28a}$ represents hydrogen, an alkoxyl group or $-OSi(R^9R^{10}R^{11})$ in which $R^9$, $R^{10}$ and $R^{11}$ each represent an alkyl group; and $R^{30}$ is an alkyl group.

The second object of the present invention can also be achieved by a compound of formula (IVb):

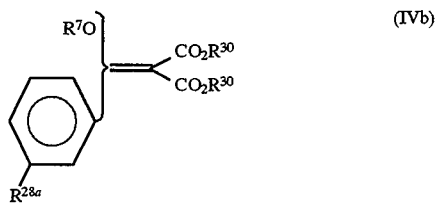

(IVb)

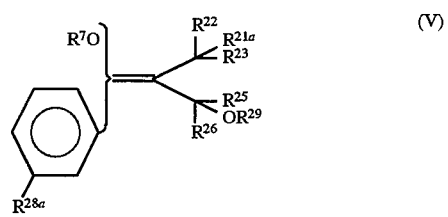

(V)

wherein $R^7$ represents an alkyl group; and $R^{28a}$ represents hydrogen, and alkoxyl group or $-OSi(R^9R^{10}R^{11})$ in which $R^9$, $R^{10}$ and $R^{11}$ each represent an alkyl group; and $R^{30}$ is an alkyl group.

The third object of the present invention can be achieved by a method of producing a compound of formula (V):

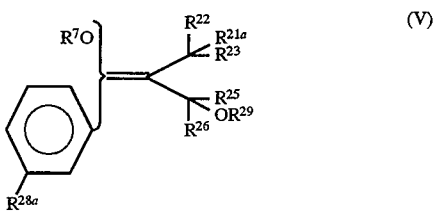

(V)

wherein $R^{21a}$, $R^{22}$, $R^{23}$, $R^{25}$ and $R^{26}$ each represent, individually, hydrogen or an alkyl group, provided that any of two selected from the group consisting of $R^{21a}$, $R^{22}$ and $R^{23}$, taken together, can form a cycloalkyl group; $R^7$ represents an alkyl group; and $R^{28a}$ represents hydrogen, an alkoxyl group, or $-OSi(R^9R^{10}R^{11})$ in which $R^9$, $R^{10}$ and $R^{11}$ each represent an alkyl group; and $R^{29}$ is an alkyl group, comprising the step of allowing compound of formula (IIIa):

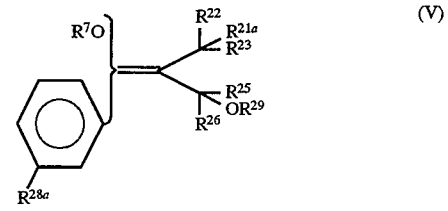

(IIIa)

wherein $R^{21a}$, $R^{22}$, $R^{23}$, $R^{25}$, $R^{26}$, $R^7$ and $R^{28a}$ are respectively the same as defined in formula (V), to react with an alkylating agent of formula $R^{29}$-X, wherein $R^{29}$ is an alkyl group and X is a halogen atom, an alkyl or aryl sulfonyloxy group, or an alkylsulfuric group, in the presence of a base.

In the above method, the compound of formula (IIIa) can be obtained by allowing a compound of formula (IVa):

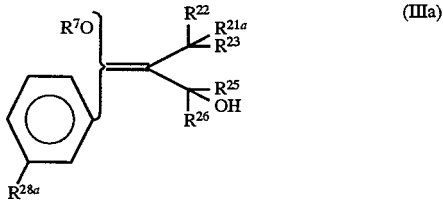

(IVa)

wherein $R^{21a}$, $R^{22}$, $R^{23}$, $R^7$ and $R^{28a}$ are respectively the same as defined in formula (IIIa), and $R^{30}$ is an alkyl group, to react with a metal hydride or an alkyl metal reagent.

The third object of the present invention can also be achieved by a method of producing a compound of formula (V):

wherein $R^{21a}$, $R^{22}$, $R^{23}$, $R^{25}$ and $R^{26}$ each represent, individually, hydrogen or an alkyl group, provided that any of two selected from the group consisting of $R^{21a}$, $R^{22}$ and $R^{23}$, taken together, can form a cycloalkyl group; $R^7$ represents an alkyl group; and $R^{28a}$ represents hydrogen, an alkoxyl group or $-OSi(R^9R^{10}R^{11})$ in which $R^9$, $R^{10}$ and $R^{11}$ each represent an alkyl group; and $R^{30}$ is an alkyl group, comprising the steps of (i) allowing a compound of formula (IIIa):

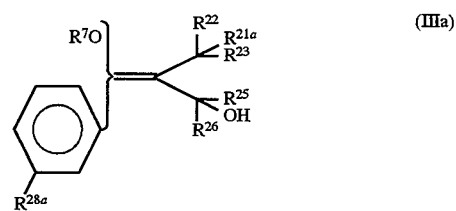

(IIIa)

wherein $R^{21a}$, $R^{22}$, $R^{23}$, $R^{25}$, $R^{26}$, $R^7$ and $R^{28a}$ are respectively the same as defined in formula (V), to react with an alkylsulfonyl chloride, an arylsulfonyl chloride or a halogenating agent, and then (ii) allowing the reaction product to react with an alcohol of formula $R^{29}$—OH, wherein $R^{29}$ is an alkyl group.

In the above method, the compound of formula (IIIa) can also be obtained by allowing a compound of formula (IVa):

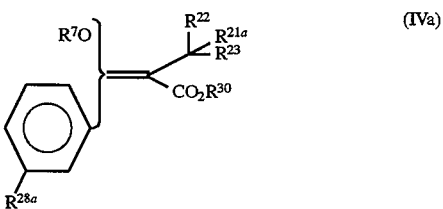

(IVa)

wherein $R^{21a}$, $R^{22}$, $R^{23}$, $R^7$ and $R^{28a}$ are respectively the same as defined in formula (IIIa), and $R^{30}$ is an alkyl group, to react with a metal hydride or an alkyl metal reagent.

The third object of the present invention can also be achieved by a method of producing a compound of formula (IIIa):

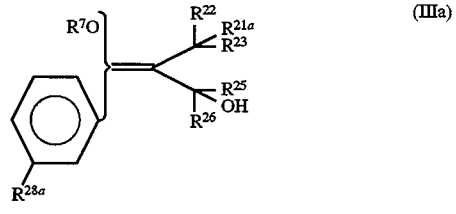

(IIIa)

wherein $R^{21a}$, $R^{22}$, $R^{23}$, $R^{25}$ and $R^{26}$ each represent, individually, hydrogen or an alkyl group, provided that any of two selected from the group consisting of $R^{21a}$, $R^{22}$ and $R^{23}$, taken together, can form a cycloalkyl group; $R^7$ represents an alkyl group; and $R^{28a}$ represents hydrogen, an alkoxyl group, or $-OSi(R^9R^{10}R^{11})$ in which $R^9$, $R^{10}$ and $R^{11}$ each represent an alkyl group, comprising the step of allowing a compound of formula (IVa):

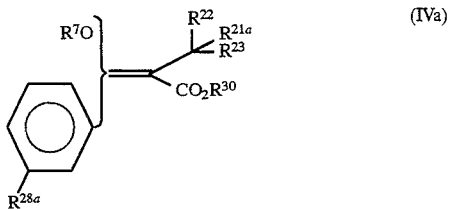

wherein $R^{21a}$, $R^{22}$, $R^{23}$, $R^7$ and $R^{28a}$ are respectively the same as defined in formula (IIIa), and $R^{30}$ is an alkyl group, to react with a metal hydride or an alkyl metal reagent.

The third object of the present invention can also be achieved by a method of producing a compound of formula (IVa):

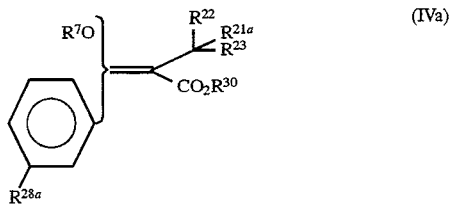

wherein $R^{21a}$, $R^{22}$ and $R^{23}$ each represent, individually, hydrogen or an alkyl group, provided that any of two selected from the group consisting of $R^{21a}$, $R^{22}$ and $R^{23}$, taken together, can form a cycloalkyl group; $R^7$ represents an alkyl group; and $R^{28a}$ represents hydrogen, an alkoxyl group or $-OSi(R^9R^{10}R^{11})$ in which $R^9$, $R^{10}$ and $R^{11}$ each represent an alkyl group; and $R^{30}$ is an alkyl group, comprising the step of allowing a compound of formula (VI):

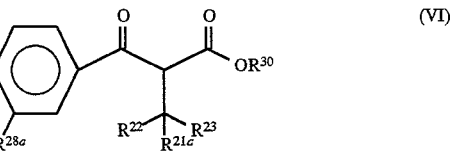

wherein $R^{21a}$, $R^{22}$, $R^{23}$, $R^{28a}$ and $R^{30}$ are respectively the same as defined in formula (IVa), to react with an alkylating agent of formula $R^7$-X, in which $R^7$ is the same as defined in formula (IVa), and X represents a halogen atom, an alkyl or arylsulfonyloxy group, or an alkylsulfuric group.

The third object of the present invention can also be achieved by a method of producing a compound of formula (IVa):

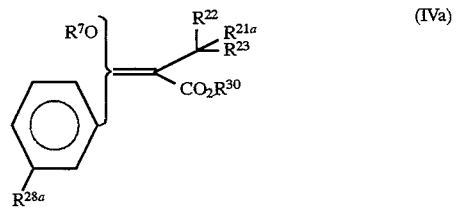

wherein $R^{21a}$, $R^{22}$ and $R^{23}$ each represent, individually, hydrogen or an alkyl group, provided that any of two selected from the group consisting of $R^{21a}$, $R^{22}$ and $R^{23}$, taken together, can form a cycloalkyl group; $R^7$ represents an alkyl group; and $R^{28a}$ represents hydrogen, an alkoxyl group or $-OSi(R^9R^{10}R^{11})$ in which $R^9$, $R^{10}$ and $R^{11}$ each represent an alkyl group; and $R^{30}$ is an alkyl group, comprising the step of allowing a compound of formula (VI):

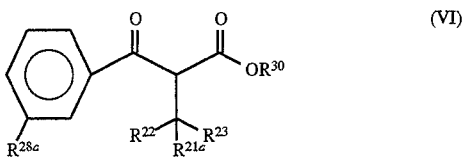

wherein $R^{21a}$, $R^{22}$, $R^{23}$, $R^{28a}$ and $R^{30}$ are respectively the same as defined in formula (IVa), to react with a compound of formula $R^7$—OH, in which $R^7$ is the same as defined in formula (IVa), in the presence of an acid catalyst.

DESCRIPTION OF THE PREFERRED EMBODIMENTS

Figure 1:
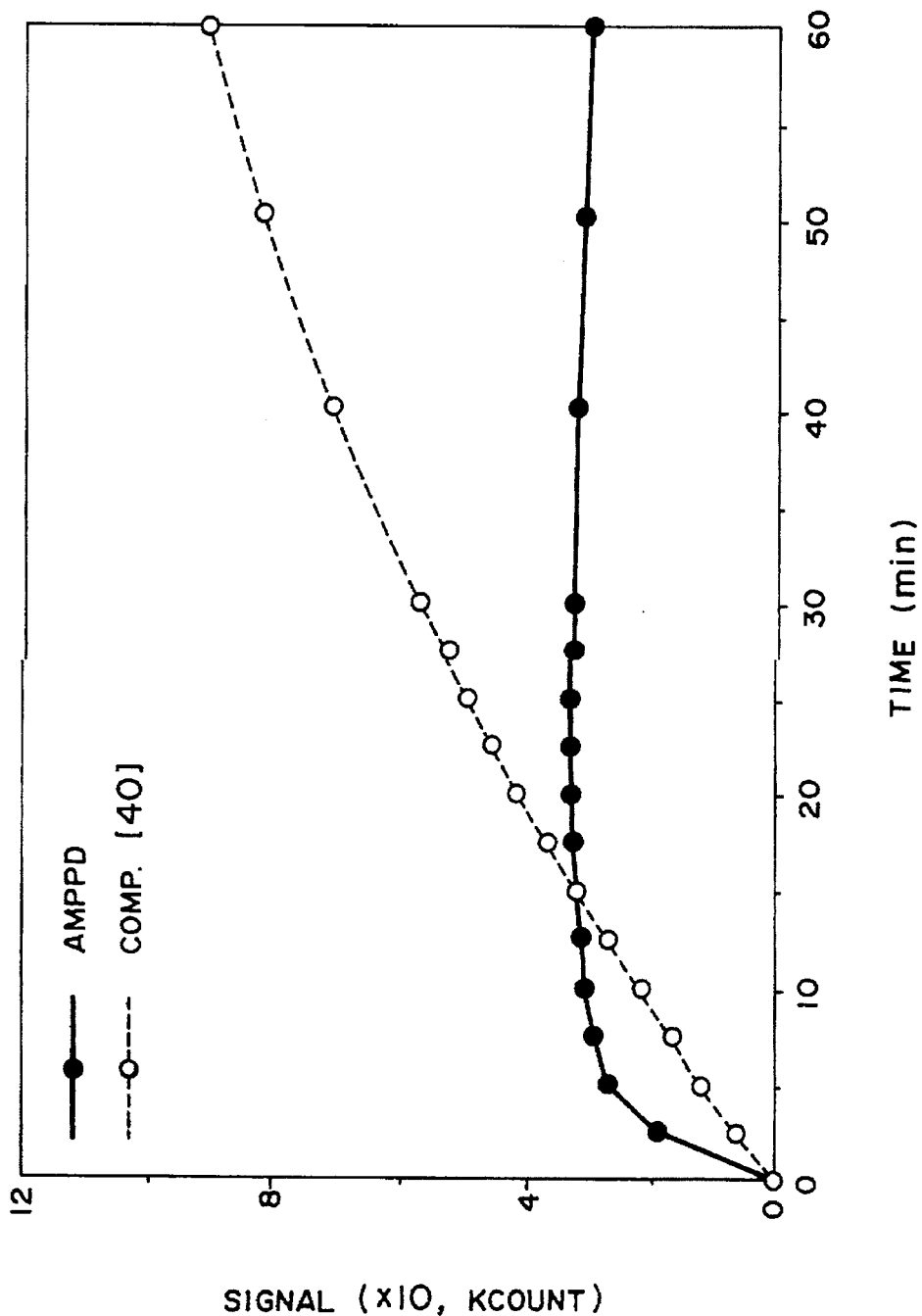
FIG. 1 is a graph showing the chemiluminescence of 3-isopropoxy-4,4-diisopropyl-3-(3'-phosphoryloxy)phenyl-1,2-dioxetane disodium salt (Compound [40]) synthesized in Example 26 in comparison with the chemiluminescence of a commercially available AMPPD (3-(2'-spiroadamantan)-4-methoxy-4-(3''-phosphoryloxy)phenyl-1,2-dioxetane disodium salt).

The 1,2-dioxetane derivative of formula (Ia), which corresponds to formula (I) in which $R^1$ and $R^4$ are respectively $R^{1a}$ and $R^{4a}$, each of which represents hydrogen or an alkyl group, can be synthesized in accordance with the following reaction scheme (I):

Reaction Scheme (I)

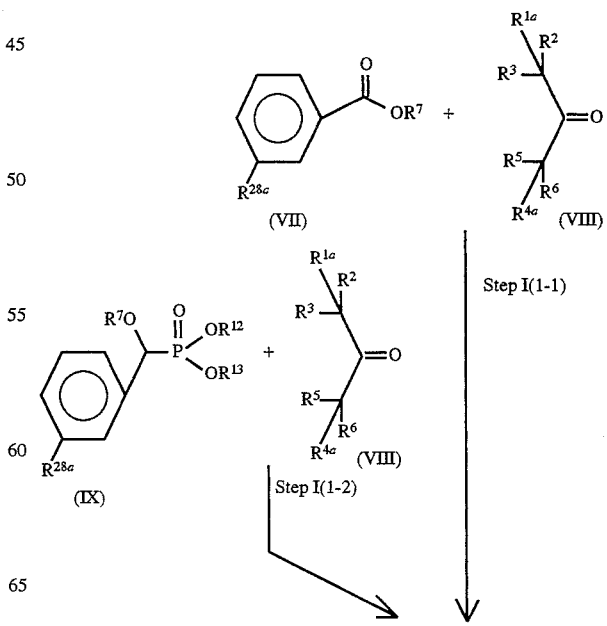

-continued
Reaction Scheme (I)

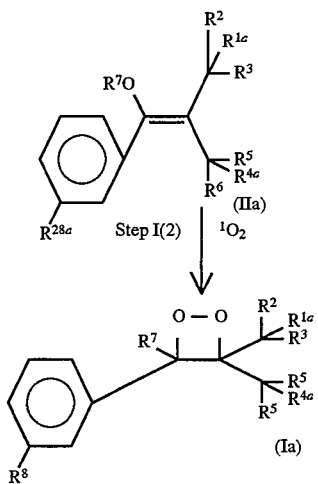

In the above reaction scheme (I), $R^2$, $R^3$, $R^5$ and $R^6$ each individually represent hydrogen or an alkyl group, and cannot be hydrogen at the same time, and $R^2$ and $R^3$, and $R^5$ and $R^6$, each taken together, can form a cyclic alkyl group; $R^7$ represents an alkyl group; $R^{12}$ and $R^{13}$ each represent an alkyl group or can together form a cycloalkyl group; $R^8$ represents hydrogen, an alkoxyl group, a phosphate salt group, or —$OSi(R^9R^{10}R^{11})$ in which $R^9$, $R^{10}$ and $R^{11}$ each represent an alkyl group; and $R^{28a}$ represents hydrogen, an alkoxyl group, or —$OSi(R^9R^{10}R^{11})$ in which $R^9$, $R^{10}$ and $R^{11}$ each represent an alkyl group.

[Step I(1—1) in Reaction Scheme (I)]

In this step, an aromatic carboxylic acid ester of formula (VII) is allowed to react with a ketone compound of formula (VIII), whereby an enol ether compound of formula (IIa) is produced.

As mentioned above, $R^{28a}$ in the aromatic carboxylic acid ester of formula (VII) may be hydrogen, an alkoxyl group, or —$OSi(R^9R^{10}R^{11})$ in which $R^9$, $R^{10}$ and $R^{11}$ each represent an alkyl group.

The aromatic carboxylic acid ester of formula (VII) in which $R^{28a}$ is the above-mentioned —$OSi(R^9R^{10}R^{11})$ can be easily produced by silylating a compound of the following formula (VIIa):

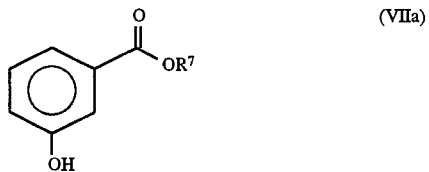

The aromatic carboxylic acid ester of formula (VII) in which $R^{28a}$ is an alkoxyl group is an industrially easily available compound.

The ketone compound of formula (VIII) is also easily available.

It is required that the reaction in Step I(1—1) be carried out in the presence of titanium. It is preferable that the titanium for use in this reaction be employed under a reduced condition, which can be obtained by reducing titanium halide such as titanium trichloride by use of a reducing agent such as lithium aluminum hydride and a base such as triethylamine.

Furthermore, the reaction can be carried out in an organic ether such as tetrahydrofuran (THF). The reaction proceeds at 0° to 100° C., but it is preferable that the reaction be carried out by refluxing the reaction mixtures in THF.

[Step I(1-2) in Reaction Scheme (I)]

In this step, an arylmethylphosphonate of formula (IX) is allowed to react with a ketone compound of formula (VIII), whereby an enol ether compound of formula (IIa) is produced.

The arylmethylphosphonate of formula (IX) employed in this step can be easily produced in accordance with a method described in Japanese Patent Publication 5-45590.

In the case where $R^{28a}$ in the enol ether compound of formula (IIa) is an alkoxyl group, the compound can be used as a starting material for the next Step I(2) by replacing $R^{28a}$ with a hydroxyl group, followed by silylating or phosphorylating the compound.

[Step I(2) in Reaction Scheme (I)]

In this step, the compound of formula (IIa) is allowed to react with singlet oxygen, whereby a 1,2-dioxetane derivative of formula (Ia) is produced.

The reaction of the compound of formula (IIa) with singlet oxygen can be carried out by dissolving the compound of formula (IIa) in a solvent such as dichloromethane, dichloroethane, carbon tetrachloride or alcohol, and subjecting the solution to the irradiation with visible light in the presence of a photosensitizer such as Methylene Blue, Rose Bengale or tetraphenylporphine in an atmosphere of oxygen. It is preferable that this reaction be carried out at −80° C. to 0° C.

The 1,2-dioxetane derivative of formula (Ib), which corresponds to formula (I) in which $R^1$ and $R^4$ are respectively $R^{1b}$ and $R^{4b}$, each of which represents hydrogen, a hydroxyl group, an alkyl group, an alkoxyl group or —$OSi(R^9R^{10}R^{11})$, but at least one of which is a hydroxyl group, an alkoxyl group or —$OSi(R^9R^{10}R^{11})$, can be synthesized in accordance with the following reaction scheme (II):

Reaction Scheme (II)

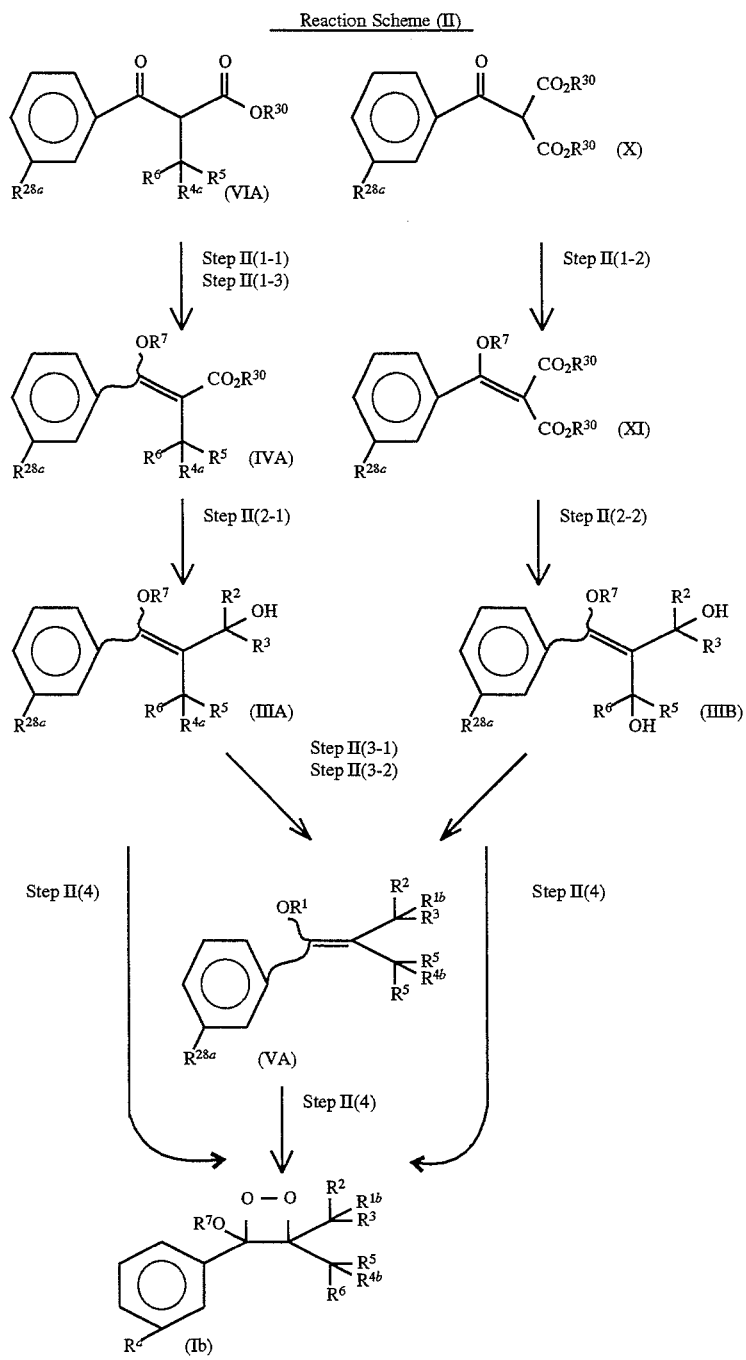

In the above reaction scheme (II), $R^2$, $R^3$, $R^5$ and $R^6$ each individually represent hydrogen or an alkyl group, and cannot be hydrogen at the same time, and $R^2$ and $R^3$, and $R^5$ and $R^6$, each taken together, can form a cycloalkyl group; $R^7$ represents an alkyl group; $R^5$ represents hydrogen, an alkoxyl group, a phosphate salt group, or —$OSi(R^9R^{10}R^{11})$ in which $R^9$, $R^{10}$ and $R^{11}$ each represent an alkyl group; $R^{28a}$ represents hydrogen, an alkoxyl group, or —$OSi(R^9R^{10}R^{11})$ in which $R^9$, $R^{10}$ and $R^{11}$ each represent an alkyl group; and $R^{30}$ represents an alkyl group.

[Step I(1—1) and Step II(1-2) in Reaction Scheme (II)]

In each of these steps, an enol ether compound of formula (IVA) or (XI) is produced by allowing an alkylating agent of $R^7$-X of formula (XII), in which $R^7$ is the same as defined previously, and X is a halogen atom, an alkyl or arylsulfonyloxy group or an alkylsulfuric group, to react with an ester compound of formula (VIA) or (X) in the presence of a base.

The compound of formula (VIA) which is used as a starting material in the above reaction can be easily produced by any of the following methods:

(1) A method of allowing a β-ketoester to react with an alkyl halide in the presence of a base or a Lewis acid as follows:

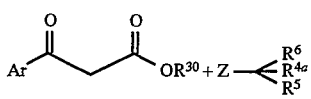

wherein Z is a halogen atom; $R^{4a}$, $R^5$, $R^6$ and $R^{30}$ are respectively the same as defined previously.

(2) A method of allowing an aromatic carboxylic acid derivative to react with an acetate in the presence of a base as follows:

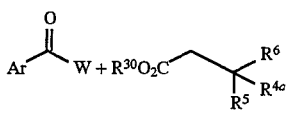

wherein W is a chlorine atom, an alkoxyl group or an amino group; and $R^{4a}$, $R^5$, $R^6$ and $R^{30}$ are respectively the same as defined previously.

(3) A method of allowing an aromatic ketone to react with a chlorocarboxylic acid ester or a carbonate ester as follows:

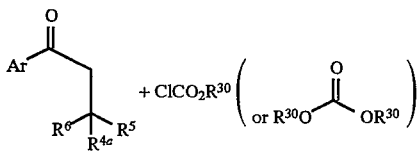

wherein $R^{4a}$, $R^5$, $R^6$ and $R^{30}$ are respectively the same as defined previously.

It is essential that Step II(1—1) and Step II(1-2) is carried out in the presence of a base.

Specific examples of such a base for use in these steps include alkaline metal alkoxides and alkaline earth metal alkoxides such as sodium methoxide, sodium etoxide, sodium t-butoxide, potassium t-butoxide and diethoxymagnesium; alkaline metal or alkaline earth metal hydrides such as lithium hydride, sodium hydride, potassium hydride and calcium hydride; alkaline metal or alkaline earth metal hydroxides such as sodium hydroxide, potassium hydroxide, calcium hydroxide and barium hydroxide; and alkaline metal carbonates such as sodium carbonate and potassium carbonate.

The reaction in each of these steps can be carried out in any of solvents, for example, ethers such as THF, dioxane, DME; amides such as DMF, DMA, N-methypyrrolidone (NMP) and HMPA; and other solvents such as DMSO, sulfolane and water. These solvents can be used alone or in combination.

When necessary, this reaction can be carried out in the presence of a phase-transfer catalyst, such as a tetraalkylammonium salt and a crown ether.

[Step II(1-3) in Reaction Scheme (II)]

In this step, the enol ether compound of formula (IVA) is synthesized by allowing the compound of formula (VIA) to react with an alcohol or $R^7$—OH of formula (XIII) in the presence of an acid catalyst.

It is essential that this step is carried out in the presence of an acid catalyst. Specific examples of the acid catalyst are mineral acids such as hydrochloric acid, sulfuric acid and phosphoric acid; organic sulfonic acids such as benzenesulfonic acid, p-toluenesulfonic acid, and salts thereof; and Lewis acids such as trifluoroboron diethyl ether complex, trichloroboron, tribromoboron, zinc chloride, and aluminum chloride.

The reaction can be carried out in an organic solvent. Examples of the solvent for the reaction include aromatic hydrocarbons such as benzene, toluene and xylene; halogenated hydrocarbons such as dichloromethane, chloroform, carbon tetrachloride and 1,2-dichloroethane; and ethers such as THF, dioxane and DME.

[Step II(2-1) and Step II(2—2)]

In each of these steps, a compound of formula (IIIA) or formula (IIIB) is produced by allowing the compound of formula (IVA) or formula (XI) to react with a reducing agent, an organic lithium reagent or a Grignard reagent.

Specific examples of the compound to be reacted with the compound of formula (IVA) or formula (XI) in these steps are as follows:

Reducing agents such as diisobutylaluminum hydride, lithium aluminum hydride, sodium aluminum hydride, sodium borohydride; alkyllithium or aryllithium compounds such as methyllithium, ethyllithium, propyllithium, butyllithium, pentyllithium, hexyllithium, butyllithium, octyllithium and phenyllithium; alkyl-magnesium halides or arylmagensium halides such as methylmagnesium chloride, methylmagnesium bromide, ethylmagnesium chloride, ethylmagnesium bromide, propylmagnesium chloride, propylmagnesium bromide, butylmagnesium chloride, butylmagnesium bromide, pentlmagnesium chloride, pentylmagnesium bromide, hexylmagnesium chloride, hexylmagnesium bromide, heptylmagnesium chloride, heptylmagnesium bromide, octylmagnesium chloride, octylmagnesium bromide, phenylmagnesium chloride and phenylmagnesium bromide.

The reaction can be carried out in an organic solvent. Examples of the solvent for the reaction include aromatic hydrocarbons such as benzene, toluene and xylene; ethers such as diethyl ether, DME, THF, dioxane and diglyme; and aromatic hydrocarbons such as heptane, hexane and pentane. These solvents can be used alone or in combination.

[Step II(3-1) in Reaction Scheme (II)]

In this step, a compound of formula (VA) is produced by allowing the compound of formula (IIIA) or formula (IIIB) to react with an alkylating agent in the presence of a base.

As the above-mentioned alkylating agent, the same alkylating agent as the alkylating agent of formula (XII) employed in Step II(1—1) and Step II(2—2) can be employed.

It is essential that the reaction in this step is carried out in the presence of a base. The same bases as employed in Step II(1—1) and Step II(2—2) can also be employed in this step. With respect to other reaction conditions for the reaction in this step, the same conditions as in Step II(1—1) and Step II(2—2) can also be adopted in this step.

[Step II(3-2) in Reaction Scheme (II)]

In this step, the previously mentioned compound of formula (VA) is produced by the steps of allowing the compound of formula (IIIA) or formula (IIIB) to react with a halogenation reagent in the presence of a base, or allowing the compound of formula (IIIA) or formula (IIIB) to react with an alkyl or arylsulfonyl chloride in the presence of a base; and then allowing the product to react with the previously mentioned alcohol of formula (XIII) in the presence of a base.

Examples of the halogenation reagent to be reacted with the compound of formula (IIIA) or (IIIB) include thionyl chloride, phosphorous trichloride, phosphorous pentachloride, phosphorous oxychloride, thionyl bromide, and phosphorous tribromide.

It is necessary that the reaction be carried out in the presence of a base. As such a base, amines such as pyridine and triethylamine are preferably employed. It is also preferably that the reaction be carried out in a solvent.

Specific examples of the solvent for the reaction are hydrocarbons such as hexane, benzene, toluene and xylene;

halogenated hydrocarbons such as dichloromethane, chloroform, carbon tetrachloride; ethers such as THF, dioxane and DME; esters such as methyl acetate and ethyl acetate; and amides such as DMF, DMA, NMP.

Furthermore, as the alkyl or arylsulfonyl chloride to be reacted with the compound of formula (IIIA) or formula (IIIB), for example, methanesulfonyl chloride, benzenesulfonyl chloride, and p-toluenesulfonyl chloride can be employed.

It is also necessary that the reaction be carried out in the presence of a base in the same manner as in the case where the halogenation reagent is reacted. As such a base, for example, the above-mentioned amines can also be employed.

The solvent for this reaction may be the same as employed in the above-mentioned reaction with the halogenation reagent.

In this step, the product can be allowed to react with the previously mentioned alcohol of formula (XIII) without isolating the product.

It is necessary that the reaction be carried out in the presence of a base, and as such a base, the same bases as employed in Step II(1—1) and Step II(1-2) can also be employed.

Furthermore, as the solvent for this reaction, the same solvents as employed in Step II(1—1) and Step II(1-2) can also be employed.

In the case where $R^{28a}$ in the enol ether compound of formula (VA) is an alkoxyl group, the compound can be used as a starting material for the next Step II(4) by replacing $R^{28a}$ with a hydroxyl group, followed by silylating or phosphorylating the compound.

[Step II(4) in Reaction Scheme (II)]

IN this step, the compound of any of formula (IIIA), (IIIB) or (VA) is allowed to react with singlet oxygen, whereby a 1,2-dioxetane derivative of formula (Ib) is produced.

The reaction of the compound of any of the above formulae with singlet oxygen can be carried out by dissolving the compound in a solvent such as dichloromethane, dichloroethane, carbon tetrachloride or alcohol, and subjecting the solution to the irradiation with visible light in the presence of a photosensitizer such as Methylene Blue, Rose Bengale or tetraphenylporphine in an atmosphere of oxygen. It is preferable that this reaction be carried out at −80° C. to 0° C.

The reaction in the above step is the same as than in Step I(2) in Reaction Scheme (I).

In the description of the present invention, the term "alkyl group" means a straight chain alkyl group having 1 to 20 carbon atoms, a branched alkyl group having 3 to 20 carbon atoms, or a cyloalkyl group having 3 to 7 carbon atoms, each of which may have a substituent.

Examples of the straight chain alkyl group include methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and icocyl group.

Examples of the substituent for the above-mentioned alkyl group include hydroxyl group, an alkoxyl group, an aryl group and a heterocyclic group.

Examples of the alkoxyl group include methoxy group, ethoxy group, propoxy group, butoxy group, pentyloxy group, hexyloxy group, methoxyethoxy group, methoxypropoxy group, ethoxyethoxy group, ethoxypropoxy group, and methoxyethoxyethoxy group.

Examples of the aryl group include phenyl group and naphthyl group.

Examples of the heterocyclic group include furyl group, thienyl group and pyridyl group.

Furthermore, in the present invention, the term "alkoxyl group" means an alkoxyl group having 1 to 20 carbon atoms, specific examples of which may be the same as mentioned above.

Furthermore, in the present invention, the term "aryl group" include aromatic hydrocarbon groups such as phenyl group and naphthyl group, and heteroaryl groups having 5 to 12 carbon atoms, which may contain nitrogen, oxygen and/or sulfur in the rings thereof.

The features of this invention will become apparent in the course of the following description of exemplary embodiments, which are given for illustration of the invention and not intended to be limiting thereof.

Reference Example 1

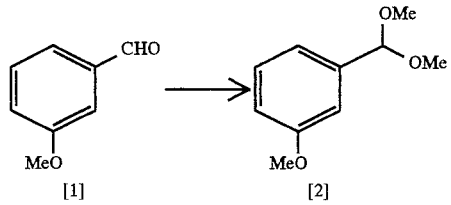

In an atmosphere of nitrogen, 1 g (5.81 mmol) of p-toluenesulfonic acid monohydrate was added to a solution of 20 ml (166 mmol) of m-anisaldehyde (Compound [1]) and 21.9 ml (199 mmol) of trimethyl orthoformate in 15 ml of anhydrous methanol, and the solution was stirred at room temperature for 22 hours.

To this solution, 2 g (23.8 mmol) of sodium hydrogencarbonate was added with stirring, and the mixture was stirred for 20 minutes. The reaction mixture was then filtered and the mother liquid was concentrated to about one-third of its original volume. The concentrated liquid was then diluted with 100 ml of ethyl acetate, and the diluted mixture was successively washed with 100 ml of a saturated aqueous solution of sodium hydrogencarbonate and then with 100 ml of a saturated aqueous solution of sodium chloride.

The organic layer was dried over anhydrous magnesium sulfate and concentrated. The residue was distilled under reduced pressure, and a distillate at 80° C./2 torr was collected, whereby m-methoxybenzaldehyde dimethylacetal (Compound [2]) was obtained in the form of a colorless oil in a yield of 27.6 g (91.0%).

$^1$HNMR (90 MHz, CDCl$_3$): δ 3.32 (s, 6H), 3.80 (s, 3H), 5.34 (s, 1H), 6.81–7.06 (m, 3H), 7.24 (t, J=7.9 Hz, 1H) ppm.

IR (liquid film): 3000, 2940, 2825, 1603, 1495, 1460, 1360, 1260, 1190, 1105, 1050 cm$^{-1}$.

Mass (m/z, %): 182 (M$^{30}$, 8), 181 (M$^+$−1, 46), 166 (30), 151 (100), 135 (85), 123 (10), 107 (52).

Reference Example 2

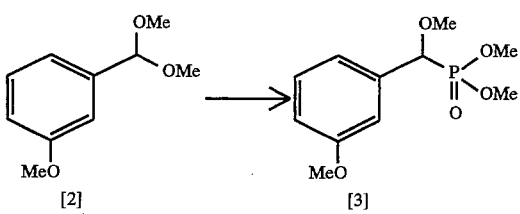

In an atmosphere of nitrogen, 27.4 g (150 mmol) of m-methoxybenzaldehyde dimethylacetal (Compound [2]) synthesized in Reference Example 1 and 17.7 ml (150 mmol) of trimethyl phosphite were dissolved in 100 ml of dichloromethane.

This reaction solution was cooled to −78° C., and 19.0 ml (150 mmol) of boron trifluoride diethyl etherate was added dropwise thereto. The temperature of the reaction mixture was then gradually elevated to room temperature. The reaction mixture was then stirred for 2.5 hours.

To this reaction mixture, 100 ml of a saturated aqueous solution of sodium hydrogencarbonate was added, and the mixture was stirred vigorously for 1 hour.

The organic layer of the mixture was then separated, washed with 100 ml of a saturated aqueous solution of sodium hydrogencarbonate, dried over anhydrous magnesium sulfate and concentrated, whereby a pale yellow oil was obtained. The thus obtained pale yellow oil was vacuum distilled at 90° C./0.2 torr, whereby the unreacted starting material (Compound [2]) was distilled away. Thus, dimethyl 1-methoxy-1-(3-methoxyphenyl)methylphosphonate (Compound [3]) was obtained in the form of a pale yellow oil in a yield of 40.5 g (95.0%).

$^1$HNMR (90 MHz, CDCl$_3$): δ 3.39 (s, 3H), 3.63 (d, J=5.1 Hz, 3H), 3.76 (d, J=5.1 Hz, 3H), 3.81 (s, 3H), 4.52 (d, J=15.6 Hz, 1H), 6.93–7.05 (m, 3H), 7.30 (t, J=7.9 Hz, 1H) ppm.

IR (liquid film): 3050, 2950, 2850, 1600, 1485, 1455, 1260, 1030 cm$^{-1}$.

Mass (m/z, %): 260 (M$^{30}$, 1), 259 (M$^+$−1, 8), 151 (100), 135 (7), 121 (10), 108 (5), 91 (4).

EXAMPLE 1

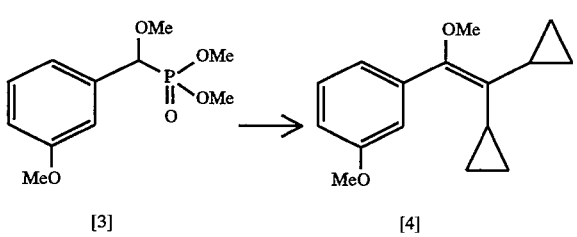

In an atmosphere of nitrogen, 1.68 ml (12.0 mmol) of diisopropylamine was added to 10 ml of anhydrous THF. To this mixture, 7.4 ml (12.0 mmol) of a 1.6M hexane solution of butyl lithium was gradually added as the mixture was ice-cooled. This mixture was then stirred at room temperature for 30 minutes, whereby a THF solution of lithium diisopropylamide was prepared.

to the thus prepared THF solution of lithium diisopropylamide, 2.46 g (10.0 mmol) of dimethyl 1-methoxy-1-(3-methoxyphenyl)methylphosphonate (Compound [3]) synthesized in Reference Example 2 was added at −78° C. The reaction mixture, with the temperature thereof raised to room temperature, was stirred for 30 minutes, and then cooled to −78° C. again, and 1.14 ml (10.0 mmol) of dicyclopropyl ketone was added thereto.

The reaction mixture, with the temperature thereof raised to room temperature, was stirred for 1 hour.

The reaction mixture, with the addition of 100 ml of a saturated aqueous solution of sodium chloride thereto, was extracted with 100 ml of hexane.

The organic layer was washed with 100 ml of a saturated aqueous solution of sodium chloride two times, dried over anhydrous magnesium sulfate and concentrated.

The residue was chromatographed on silica gel and eluted with hexane, whereby 1,1-dicyclopropyl-2-methoxy-2-(3-methoxyphenyl)ethene (Compound [4]) was obtained in a yield of 1.7 g (66%).

$^1$HNMR (400 MHz, CDCl$_3$): δ 0.07–0.11 (m, 2H), 0.39–0.43 (m, 2H), 0.66–0.79 (m, 4H), 1.14 (m, 1H), 1.78 (m, 1H), 3.38 (s, 3H), 3.81 (s,3H), 6.81–6.84 (m, 1H), 6.94–7.00 (m, 2H), 7.22–7.25 (m, 1H) ppm.

IR (liquid film): 3100, 2950, 2800, 1600, 1460, 1285, 1030 cm$^{-1}$.

Mass (m/z, %): 244 (M$^{30}$, 42), 229 (5), 213 (100), 203 (18), 185 (14), 171 (28), 159 (10), 137 (88), 128 (13), 121 (35), 115 (18).

EXAMPLE 2

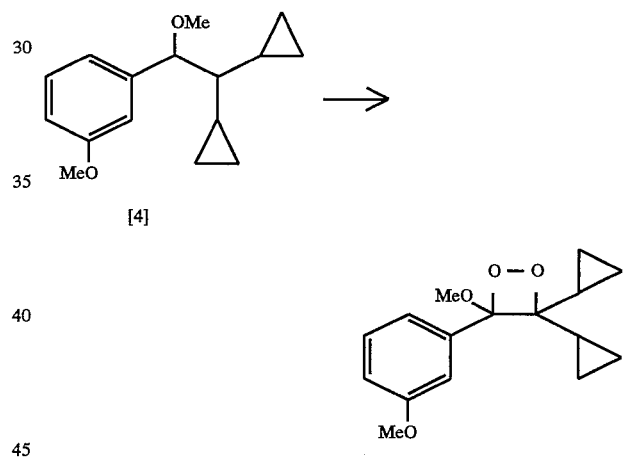

50 mg (0.20 mmol) of 1,1-dicyclopropyl-2-methoxy-2-(3-methoxyphenyl)ethene (Compound [4]) synthesized in Example 1 was dissolved in 10 ml of dichloromethane. To this solution, 5 mg (8.15 mmol) of tetraphenylphorphine was added.

This solution, with vigorously stirring in the atmosphere of oxygen at −78° C., was irradiated with a sodium lamp for 1 hour.

The reaction mixture was concentrated, and the residue was subjected to preparative TLC and developed with a mixed solvent of hexane and ethyl acetate (20:1), whereby 3,3-dicyclopropyl-4-methoxy-4-(3-methoxyphenyl)-1,2-dioxetane (Compound [5]) was obtained in the form of a pale yellow oil in a yield of 30 mg (52%).

$^1$HNMR (400 MHz, CDCl$_3$): δ 0.03–0.10 (m, 1H), 0.21–0.35 (m, 3H), 0.37–0.43 (m, 1H), 0.57–0.70 (m, 2H), 0.80–0.91 (m, 2H), 1.77–1.84 (m, 1H), 3.15 (s, 3H), 3.84 (s, 3H), 6.89–6.92 (m, 1H), 7.01–7.03 (m, 2H), 7.30–7.34 (m, 1H) ppm.

$^{13}$CNMR (400 MHz, CDCl$_3$): δ 1.4, 1.5, 1.6, 1.7, 11.9, 12.6, 50.0, 55.4, 93.0, 112.5, 113.0, 114.3, 119.3, 129.2, 137.7, 159.5 ppm.

IR (liquid film): 3085, 3050, 2830, 1600, 1585, 1490, 1460, 1430, 1285, 1085, 1005 cm$^{-1}$.

Mass (m/z, %): 244 (M$^{30}$ –32, 1), 166 (52), 135 (78), 107 (39), 92 (18), 77 (27), 69 (100).

Reference Example 3

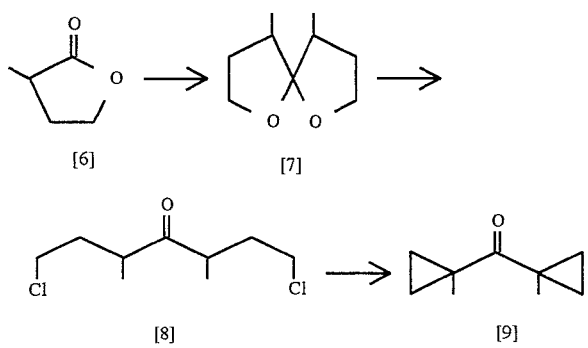

In an atmosphere of nitrogen, 15 ml (107 mmol) of diisopropylamine was added to 100 ml of hexane. To this solution, 65 ml (107 mmol) of a 1.6M hexane solution of butyl lithium was gradually added dropwise as the mixture was ice-cooled. This mixture was then stirred at room temperature for 30 minutes, whereby a hexane solution of lithium diisopropylamide was prepared.

To the thus prepared hexane solution of lithium diisopropylamide, 25.4 ml (199 mmol) of α-methyl-λ-butyrolactone (Compound [6]) was added at –78° C., and the mixture was stirred at room temperature for 14 hours.

To this reaction mixture, 200 ml of 2N sulfuric acid was added, and the solvent was distilled. The residue was refluxed for 2 hours.

The residue was extracted with 100 ml of ether, and the extract was washed with 100 ml of a 1N aqueous solution of sodium hydroxide. The organic layer was dried over anhydrous magnesium sulfate and concentrated, whereby 14 g of spiroacetal (Compound [7]) was obtained.

To the thus obtained spiroacetal, 100 ml of concentrated hydrochloric acid was added, and the mixture was refluxed for 30 minutes.

This reaction solution was extracted with 100 ml of ether. The organic layer was dried over anhydrous magnesium sulfate and concentrated, whereby 15 g of dichloroketone (Compound [8]) was obtained.

To this obtained dicloroketone, an ethanolic potassium hydroxide solution was added at 80° C., and the mixture was refluxed for 2 hours. The solvent was removed from this reaction mixture, and 100 ml of ether was added to the residue. The mixture was then washed with 100 ml of a saturated aqueous solution of sodium chloride. The organic layer was dried over anhydrous magnesium sulfate and concentrated. The residue was then distilled under reduced pressure, and a distillate at 76° C./2 torr was collected, whereby bis(1-methylcyclopropyl)ketone (Compound [9]) was obtained in the form of a colorless oil in a yield of 5.0 g (36%).

$^1$HNMR (400 MHz, CDCl$_3$): δ 0.51–0.62 (m, 4H), 1.02–1.34 (m, 4H), 1.45 (s, 6H) ppm.

IR (liquid film): 3100, 2970, 1690, 1460, 1380, 1340, 1060 cm$^{-1}$.

EXAMPLE 3

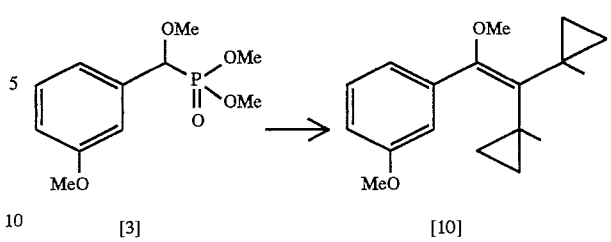

In an atmosphere of nitrogen, 6.72 ml (24.0 mmol) of diisopropylamine was added to 20 ml of anhydrous THF. To this mixture, 29.6 mol (24.0 mmol) of a 1.6M hexane solution of butyl lithium was added as the mixture was ice-cooled. This mixture was then stirred at room temperature for 30 minutes, whereby a THF solution of lithium diisopropylamide was prepared.

To the thus prepared THF solution of lithium diisopropylamide, 984 g (20.0 mmol) of dimethyl 1-methoxy-1-(3-methoxyphenyl)methylphosphonate (Compound [3]) synthesized in Reference Example 2 was added at –78° C. The reaction mixture, with the temperature thereof raised to room temperature, was stirred for 30 minutes and then cooled to –78° C. again, and 1.1 g (8.0 mmol) of bis(1-methylcyclopropyl)ketone (Compound [9]) synthesized in Reference Example 3 was added thereto.

This reaction solution, with the temperature thereof raised to room temperature, was stirred for 1 hour.

The reaction solution, with the addition of 100 ml of a saturated aqueous solution of sodium chloride thereto, was extracted with 100 ml of hexane.

The organic layer of the mixture was washed with 100 ml of a saturated aqueous solution of sodium chloride two times, dried over anhydrous magnesium sulfate and concentrated.

The residue was chromatographed on silica gel and eluted with hexane, whereby 2-methoxy-2-(3-methoxyphenyl)-1,1-bis(1-methylcyclopropyl)ethene (Compound [10]) was obtained in the form of a colorless oil in a yield of 600 mg (28%).

$^1$HNMR (400 MHz, CDCl$_3$): δ 0.10–0.13 (m, 2H), 0.16–0.19 (m, 2H), 0.51–0.53 (m, 2H), 0.84–0.87 (m, 2H), 1.22 (s, 3H), 1.28 (s, 3H), 3.34 (s, 3H), 3.82 (s, 3H), 6.84–6.85 (m, 2H), 6.89–6.91 (m, 1H), 7.23–7.27 (m, 1H) ppm.

IR (liquid film): 3080, 2950, 2830, 1600, 1575, 1450, 1280, 1225, 1085 cm$^{-1}$.

Mass (m/z, %): 272 (M$^+$, 11), 257 (16), 241 (100), 225 (87), 211 (21), 199 (15), 185 (19), 165 (93), 151 (23), 135 (77), 128 (12), 121 (34), 115 (17).

EXAMPLE 4

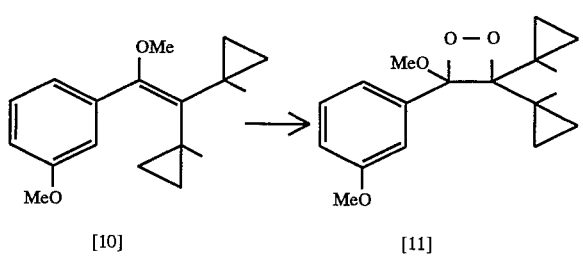

40 mg (0.14 mmol) of 2-methoxy-2-(3-methoxyphenyl)-1,1-bis(1-methylcyclopropyl)ethene (Compound [10]) synthesized in Example 3 was added to 10 ml of dichloromethane. To this solution, 5 mg (8.15 mmol) of tetraphenylporphine was added.

This solution was ice-cooled and irradiated with a sodium lamp for 1 hour, with vigorously stirring in the atmosphere of oxygen.

The reaction solution was concentrated, and the residue was chromatographed on silica gel and eluted with a mixed solvent of hexane and ethyl acetate (10:1), whereby 3-methoxy-3-(3-methoxyphenyl)-4,4-bis(1-methylcyclopropyl)-1,2-dioxetane (Compound [11]) was obtained in the form of a pale yellow oil in a yield of 40 mg (85%).

$^1$HNMR (400 MHz, CDCl$_3$): δ 0.07–0.12 (m, 1H), 0.13–0.17 (m, 1H), 0.25–0.30 (m, 1H), 0.39–0.44 (m, 1H), 0.48–0.58 (m, 2H), 0.70 (s, 3H), 1.36–1.43 (m, 2H), 1.38 (s, 3H), 3.12 (s, 3H), 3.85 (s, 3H), 6.91–6.94 (m, 1H), 7.18–7.20 (m, 2H), 7.33 (t, J=7.8 Hz, 1H) ppm.

$^{13}$CNMR (400 MHz, CDCl$_3$): δ 8.4, 9.9, 13.3, 13.5, 19.3, 19.7, 21.9, 23.9, 49.4, 55.3, 94.4, 113.2, 114.4, 114.6, 120.9, 128.9, 137.4, 159.4 ppm.

IR (liquid film): 3100, 3000, 2830, 1600, 1460, 1285, 1170, 1075 cm$^{-1}$.

Mass (m/z, %): 273 (M$^+$–31, 6), 241 (21), 166 (100), 135 (84), 123 (44).

EXAMPLE 5

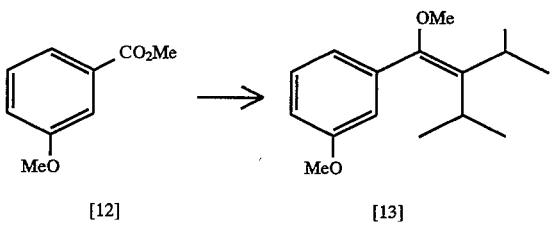

In an atmosphere of nitrogen, 9.0 g (60 mmol) of titanium trichloride was suspended in 100 ml of anhydrous THF and ice-cooled. To this ice-cooled suspension, 1.14 g (30 mmol) of lithium aluminum hydride was added.

To this reaction solution, with the temperature thereof raised to room temperature, 4.2 ml (30 mmol) of triethylamine was added, and the mixture was refluxed for 15 minutes.

To the thus refluxed mixture, a solution of 1.0 g (6.0 mmol) of methyl 3-methoxybenzoate (Compound [12]) and 3.0 ml (12.0 mmol) of diisopropyl ketone in 30 ml of anhydrous THF was added dropwise over a period of 20 minutes. This reaction solution was further refluxed for 30 minutes.

This reaction solution was then ice-cooled and water was added dropwise thereto. The reaction mixture was then extracted with 100 ml of ethyl acetate. The extracted layer was washed with 100 ml of distilled water four times, dried over anhydrous magnesium sulfate and concentrated.

The residue was chromatographed on silica gel and eluted with a mixed solvent of hexane and ethyl acetate (20:1), whereby 1,1-diisopropyl-2-methoxy-2-(3-methoxyphenyl)ethene (Compound [13]) was obtained in the form of a colorless oil in a yield of 630 mg (40%).

$^1$HNMR (400 MHz, CDCl$_3$): δ 0.89 (d, J=6.8 Hz,6H), 0.92 (d, J=6.8 Hz, 6H), 2.32 (sept, J=6.8 Hz, 1H), 2.46 (sept, J=6.8 Hz, 1H), 3.19 (s, 3H), 3.81 (s, 3H), 6.79–6.85 (m, 3H), 7.24 (t, J=7.8 Hz, 1H) ppm.

$^{13}$CNMR (400 MHz, CDCl$_3$): δ 21.0, 22.0, 26.7, 30.4, 55.2, 56.2, 113.2, 114.9, 122.3, 128.8, 132.7, 137.8, 149.8, 159.4 ppm.

IR (liquid film): 3070, 2950, 28700, 1600, 1575, 1480, 1460, 1285, 1230, 1120, 1070 cm$^{-1}$.

Mass (m/z, %): 248 (M$^+$, 43), 233 (100), 205 (93), 57 (77).

EXAMPLE 6

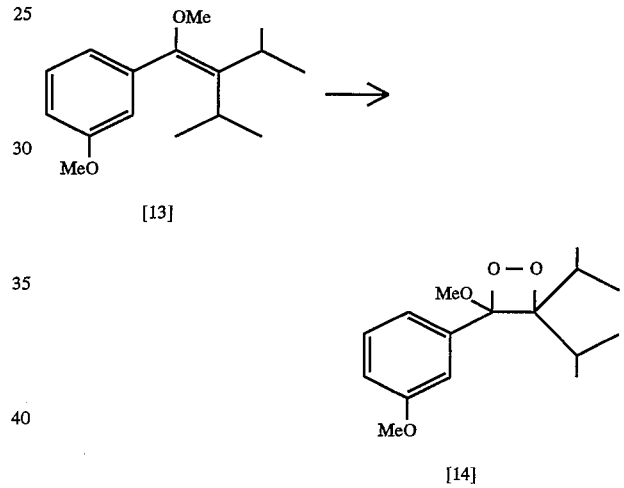

50 mg (0.19 mmol) of 1,1-diisopropyl-2-methoxy-2-(3-methoxyphenyl)ethene (Compound [13]) synthesized in Example 5 was dissolved in 10 ml of dichloromethane. To this solution, 5 mg of tetraphenylporphine was added.

This solution was cooled to –78° C. and irradiated with a sodium lamp for 1 hour, with vigorously stirring in the atmosphere of oxygen.

The reaction solution was concentrated, and the residue was chromatographed on a thin-layer chromatography plate and developed with a mixed solvent of hexane and ethyl acetate (20:1), whereby 3,3-diisopropyl-4-methoxy-4-(3-methoxyphenyl)-1,2-dioxetane (Compound [14]) was obtained in the form of a pale yellow oil in a yield of 45 mg (85%).

$^1$HNMR (400 MHz, CDCl$_3$): δ 0.46 (d, J=6.8 Hz, 3H), 0.92 (d, J=6.8 Hz, 3H), 1.18 (d, J=6.8 Hz, 3H), 1.30 (d, J=6.8 Hz, 3H), 2.46 (sept, J=6.8 Hz, 1H), 2.59 (sept, J=6.8 Hz, 1H), 3.12 (s, 3H), 3.84 (s, 3H), 6.91–7.34 (m, 4H) ppm.

$^{13}$CNMR (400 MHz, CDCl$_3$): δ 16.7, 17.2, 18.5, 19.4, 29.2, 33.5, 49.4, 55.4, 98.2, 113.4, 114.4, 114.6, 120.5, 129.3, 137.0, 159.6 ppm.

IR (liquid film): 3100, 2950, 2800, 1600, 1460, 1285, 1030 cm$^{-1}$.

Mass (m/z, %): 248 (M⁺−32, 5), 247 (25), 232 (18), 204 (19), 165 (59), 134 (100), 114 (14).

Reference Example 4

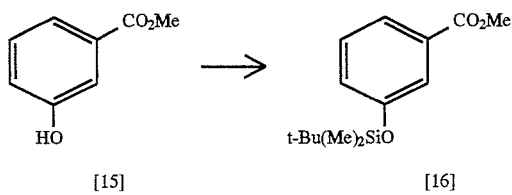

In an atmosphere of nitrogen, 3.04 g (20.0 mmol) of methyl 3-hydroxybenzoate (Compound [15]) was dissolved in 20 ml of anhydrous DMF. To this solution, 3.3 ml (24.0 mmol) of triethylamine was added.

To this solution, 3.6 g (24 mmol) of t-butyldimethyl chlorosilane was added while the solution was ice-cooled. This mixture was then stirred at room temperature overnight.

100 ml of distilled water was added to this reaction solution, and the mixture was extracted with 100 ml of ethyl acetate.

The organic layer was washed with 100 ml of a saturated aqueous solution of sodium chloride, dried over anhydrous magnesium sulfate and concentrated.

The residue was chromatographed on silica gel and eluted with a mixed solvent of hexane and ethyl acetate (5:1), whereby methyl 3-(t-butyldimethylsiloxy)benzoate (Compound [16]) was obtained in the form of a colorless oil in a yield of 5.1 g (96%).

¹HNMR (90 MHz, CDCl₃): δ 0.25 (s, 6H), 1.03 (s, 9H), 3.88 (s, 3H), 6.98–7.15 (m, 1H), 7.33 (t, J=7.8 Hz, 1H), 7.50–7.56 (m, 2H) ppm.

IR (liquid film): 2956, 2896, 2860, 1732, 1600, 1586, 1292, 1228, 1076 cm⁻¹.

Mass (m/z, %): 266 (M⁺, 25), 209 (100), 177 (30), 149 (15).

EXAMPLE 7

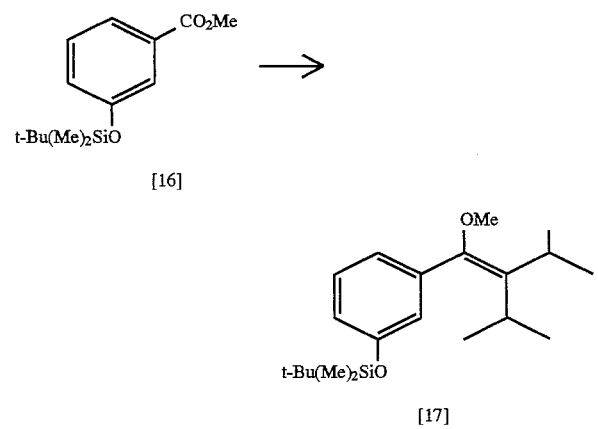

In an atmosphere of nitrogen, 4.50 g (30 mmol) of titanium trichloride was suspended in 100 ml of anhydrous THF. The mixture was stirred for 20 minutes and then ice-cooled. To this ice-cooled suspension, 0.57 g (15 mmol) of lithium aluminum hydride was added.

To this reaction solution, with the temperature thereof raised to room temperature, 2.1 ml (15 mmol) of triethylamine was added, and the mixture was refluxed for 15 minutes.

To the thus refluxed mixture, a solution of 1.33 g (5 mmol) of methyl 3-(t-butyldimethylsiloxy)benzoate (Compound [16]) synthesized in Reference Example 4 and 0.75 ml (5.3 mmol) of diisopropyl ketone in 20 ml of anhydrous THF was added dropwise over a period of 20 minutes. This reaction solution was further refluxed for 30 minutes.

This reaction solution was then ice-cooled and water was added dropwise thereto. The reaction mixture was then extracted with 100 ml of ethyl acetate. The extracted layer was washed with 100 ml of distilled water four times, dried over anhydrous magnesium sulfate and concentrated.

The residue was chromatographed on silica gel and eluted with a mixed solvent of hexane and ethyl acetate (20:1), whereby 2-[3-(t-butyldimethylsiloxy)phenyl]-1,1-diisopropyl-2-methoxyethene (Compound [17]) was obtained in the form of a colorless oil in a yield of 0.40 g (23%).

¹HNMR (90 MHz, CDCl₃): δ 0.25 (s, 6H), 0.89 (d, J=7.0 Hz, 6H), 0.98 (s, 9H), 0.92 (d, J=7.0 Hz, 6H), 2.32 (sept, J=7.0 Hz, 1H), 2.46 (sept, J=7.0 Hz, 1H), 3.19 (s, 3H), 6.79–6.91 (m, 3H), 7.11–7.30 (m, 1H) ppm.

IR (liquid film): 2960, 2932, 1598, 1578, 1482, 1286, 1070 cm⁻¹.

Mass (m/z, %): 348 (M⁺, 80), 333 (100), 305 (96), 219 (31).

EXAMPLE 8

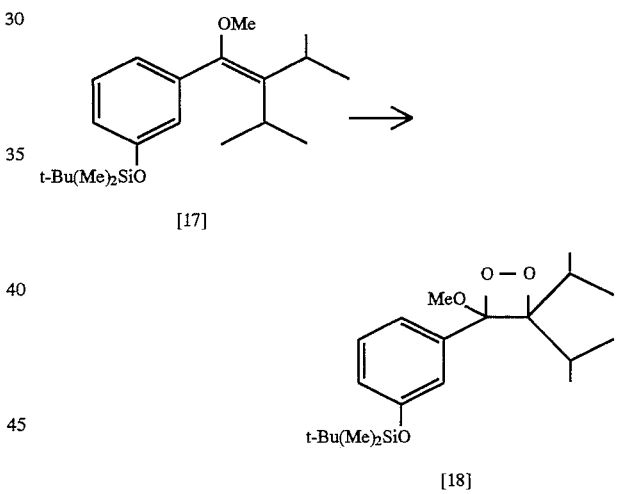

60 mg (0.18 mmol) of 2-[3-(t-butyldimethylsiloxy) phenyl]-1,1-diisopropyl-2-methoxyethene (Compound [17]) synthesized in Example 7 was dissolved in 10 ml of dichloromethane. To this solution, 5 mg of tetraphenylporphine was added.

This solution was cooled to −78° C. and irradiated with a sodium lamp for 1 hour, with vigorously stirring in the atmosphere of oxygen.

The reaction solution was concentrated, and the residue was chromatographed on silica gel and eluted with a mixed solvent of hexane and ethyl acetate (10:1), whereby 3-[3-(t-butyldimethylsiloxy)phenyl]-4,4-diisopropyl-3-methoxy-1,2-dioxetane (Compound [18]) was obtained in the form of a pale yellow oil in a yield of 50 mg (72%).

¹HNMR (90 MHz, CDCl₃): δ 0.25 (s, 6H), 0.52 (d, J=7.0 Hz, 3H), 0.98 (d, J=7.0 Hz, 3H), 1.05 (s, 9H), 1.22 (d, J=7.0 Hz, 3H), 1.35 (d, J=7.0 Hz, 3H), 2.59 (sept, J=7.0 Hz, 2H), 3.19 (s, 3H), 6.83–7.35 (m, 4H) ppm.

IR (liquid film): 2960, 2860, 1600, 1480, 1290, 1115, 1010, 840 cm$^{-1}$.

Mass (m/z, %): 349 (M$^+$−31, 39), 334 (28), 306 (35), 267 (13), 234 (25), 210 (100), 178 (46), 150 (46), 135 (37), 121 (11).

Reference Example 5

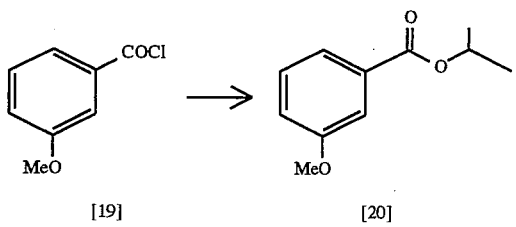

3 ml (21.5 mmol) of triethylamine was added to 8 ml (105 mml) of 2-propanol, and the mixture was ice-cooled. To this ice-cooled mixture, 2.5 ml (17.8 mmol) of m-anisoyl chloride (Compound [19]) was added dropwise.

This reaction solution, with the temperature thereof raised to room temperature, was stirred for 18 hours.

The reaction mixture was extracted with 30 ml of ethyl acetate, and the extracted layer was washed with 30 ml of a saturated aqueous solution of sodium chloride and 20 ml of a saturated aqueous solution of ammonium chloride, three times each, dried over anhydrous magnesium sulfate and concentrated, whereby 3.37 g of a crude product was obtained.

The thus obtained crude product was chromatographed on silica gel, whereby isopropyl 3-methoxybenzoate (Compound [20]) was obtained in the form of a pale yellow oil in a yield of 3.14 g (91%).

$^1$HNMR (90 MHz, CDCl$_3$): δ 1.37 (d, J=6.3 Hz, 6H), 3.85 (s, 3H), 5.25 (sept, J=6.3 Hz, 1H), 6.96−7.68 (m, 4H) ppm.

IR (liquid film): 3070, 2982, 2836, 1715, 1601, 1587, 1280 cm$^{-1}$.

Mass (m/z, %): 194 (M$^+$, 81), 152 (99), 136 (30), 135 (100), 107 (22).

EXAMPLE 9

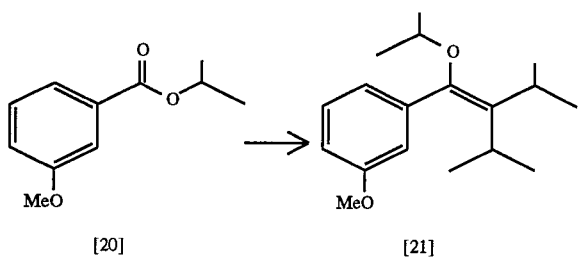

In an atmosphere of nitrogen, 4.50 g (30 mmol) of titanium trichloride was suspended in 100 ml of anhydrous THF. This suspension was stirred for 20 minutes and ice-cooled. To this ice-cooled suspension, 0.57 g (15 mmol) of lithium aluminum hydride was added.

To this reaction solution, with the temperature thereof raised to room temperature, 2.1 ml (15 mmol) of triethylamine was added, and the mixture was refluxed for 15 minutes.

To the thus refluxed mixture, a solution of 0.58 g (3 mmol) of isopropyl 3-methoxybenzoate (Compound [20]) synthesized in Reference Example 5 and 0.85 ml (6 mmol) of diisopropyl ketone in 20 ml of anhydrous THF was added dropwise over a period of 10 minutes. This reaction mixture was further refluxed for 15 minutes.

This reaction solution was then ice-cooled and water was added dropwise thereto. The reaction mixture was then extracted with 150 ml of ethyl acetate. The extracted layer was washed with 100 ml of distilled water five times, dried over anhydrous magnesium sulfate and concentrated, whereby 0.69 g of a crude product was obtained.

The thus obtained crude product was chromatographed on silica gel, whereby 2-isopropoxy-1,1-diisopropyl-2-(3-methoxyphenyl)ethene (Compound [21]) was obtained in the form of a pale yellow oil in a yield of 0.47 g (57%).

$^1$HNMR (400 MHz, CDCl$_3$): δ 0.89 (d, J=6.8 Hz, 6H), 1.09 (d, J=5.9 Hz, 6H), 1.26 (d, J=6.8 Hz, 6H), 2.41 (sept, J=6.8 Hz, 2H), 3.64 (sept, J=5.9 Hz, 1H), 3.81 (s, 3H), 6.79−7.23 (m, 4H) ppm.

$^{13}$CNMR (400 MHz, CDCl$_3$): δ 21.22, 21.26, 22.08, 22.30, 22.34, 22.37, 26.49, 30.38, 55.24, 68.13, 112.74, 115.20, 122.39, 128.70, 130.99, 138.43, 147.15, 159.22 ppm.

IR (liquid film): 3080, 2870, 2835, 1648, 1568, 1381, 1369 cm$^{-1}$.

Mass (m/z, %): 276 (M$^+$, 23), 234 (24), 219 (71), 199 (18), 191 (100), 156 (37), 135 (39).

EXAMPLE 10

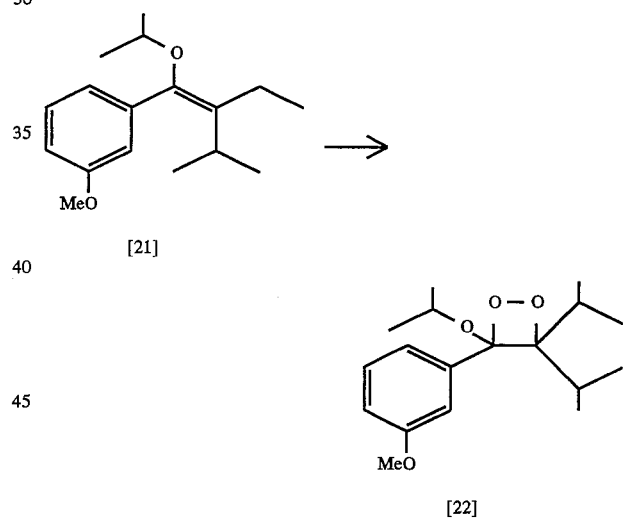

55.5 mg (0.20 mmol) of 2-isopropoxy-1,1-diisopropyl-2-(3-methoxyphenyl)ethene (Compound [21]) synthesized in Example 9 was dissolved in 10 ml of dichloromethane. To this solution, 7.4 mg of tetraphenylporphine was added.

This reaction solution, with vigorously stirring in the atmosphere of oxygen, was irradiated with a sodium lamp for 1 hour and 30 minutes.

The reaction solution was concentrated, and the residue was chromatographed on a thin-chromatography plate and developed with a mixed solvent of hexane and ethyl acetate (20:1), whereby 3-isopropoxy-4,4-diisopropyl-3-(3-methoxyphenyl)-1,2-dioxetane (Compound [22]) was obtained in the form of a pale yellow oil in a yield of 33 mg (53.6%).

$^1$HNMR (400 MHz, CDCl$_3$): δ 0.47 (d, J=7.3 Hz, 3H), 0.87 (d, J=6.8 Hz, 3H), 1.10 (d, J=5.9 Hz, 3H), 1.22 (d, J=6.8

Hz, 3H), 1.26 (d, J=5.9 Hz, 3H), 1.36 (d, J=7.3 Hz, 3H), 2.34–2.51 (m, 2H), 3.58 (sept, J=5.9 Hz, 1H), 3.84 (s, 3H), 6.90–7.32 (m, 4H) ppm.

$^{13}$CNMR (400 MHz, CDCl$_3$): δ 16.32, 17.33, 18.75, 19.39, 23.64, 24.72, 29.10, 33.38, 55.29, 67.71, 98.51, 112.95, 114.49, 119.96, 121.53, 128.88, 138.61, 159.33 ppm.

IR (liquid film): 3090, 2971, 2936, 2879, 2836, 1602, 1585, 1385, 1364, cm$^{-1}$, Mass (m/z, %): 276 (M$^+$–32, 14), 234 (9), 219 (9), 194 (60), 179 (6), 152 (77), 135 (100), 114 (22), 107 (34).

Reference Example 6

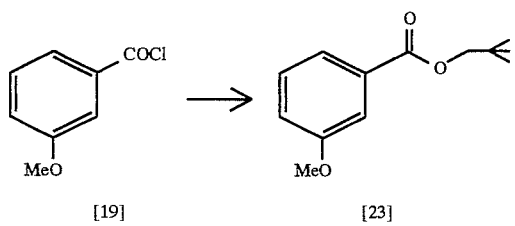

2.5 ml (17.8 mmol) of m-anisoyl chloride (Compound [19]) was added dropwise to an ice-cooled solution of 7.73 g (87.7 mmol) of 2,2-dimethyl-1-propanol in 3 ml (21.5 mmol) of triethylamine and the reaction solution was stirred at room temperature for 22 hours.

The reaction solution was then extracted with 30 ml of ethyl acetate, and the extracted layer was successively washed with 20 ml of a saturated aqueous solution of sodium chloride two times and with 20 m of a saturated aqueous solution of ammonium chloride four times, dried over anhydrous magnesium sulfate, and concentrated, whereby 3.47 g of a crude product was obtained.

The thus obtained crude product was chromatographed on silica gel, whereby neopentyl 3-methoxybenzoate (Compound [23]) was obtained in the form of a pale yellow oil in a yield of 3.23 g (82%).

$^1$HNMR (90 MHz, CDCl$_3$): δ 1.04 (s, 9H), 3.86 (s, 3H), 4.02 (s, 2H), 7.02–7.73 (m, 4H), ppm.

IR (liquid film): 3090, 2960, 2871, 2837, 1724, 1602, 1587, 1401, 1370 cm$^{-1}$.

EXAMPLE 11

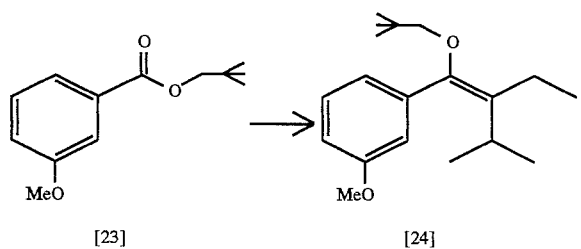

In an atmosphere of nitrogen, 4.50 g (30 mmol) of titanium trichloride was suspended in 100 ml of anhydrous THF. This suspension was stirred for 15 minutes and ice-cooled. To this ice-cooled suspension, 0.57 g (15 mmol) of lithium aluminum hydride was added.

To this reaction solution, with the temperature thereof raised to room temperature, 2.1 ml (15 mmol) of triethylamine was added, and the mixture was refluxed for 15 minutes.

To the thus refluxed mixture, a solution of 0.66 g (3 mmol) of neopentyl 3-methoxybenzoate (Compound [23]) synthesized in Reference Example 6 and 0.85 ml (6 mmol) of diisopropyl ketone in 20 ml of anhydrous THF was added dropwise over a period of 60 minutes. This reaction solution was further refluxed for 15 minutes.

This reaction solution was then ice-cooled and water was added dropwise thereto. The reaction mixture was then extracted with 120 ml of ethyl acetate. The extracted layer was washed with 100 ml of distilled water four times, dried over anhydrous magnesium sulfate and concentrated, whereby 0.78 g of a crude product was obtained.

The thus obtained crude product was chromatographed on silica gel, whereby 1,1-diisopropyl-2-(3-methoxyphenyl)-2-neopentyloxyethene (Compound [24]) was obtained in the form of a colorless oil in a yield of 0.41 g (45%).

$^1$HNMR (400 MHz, CDCl$_3$): δ 0.90 (s, 9H), 0.91 (d, J=6.8 Hz, 6H), 1.26 (d, J=6.8 Hz, 6H), 2.33 (sept, J=6.8 Hz, 1H), 2.45 (sept, J=6.8 Hz, 1H), 2.94 (s, 2H), 3.81 (s, 3H), 6.78–7.25 (m, 4H) ppm.

$^{13}$CNMR (400 MHz, CDCl$_3$): δ 21.02, 21.95, 26.76, 27.02, 30.53, 31.94, 55.16, 77.84, 113.06, 114.87, 122.37, 128.65, 131.99, 138.56, 148.95, 159.22 ppm.

IR (liquid film): 3649, 3068, 3027, 2957, 2869, 2836, 1652, 1606, 1577, 1485, 1464, 1380, 1362 cm$^{-1}$.

Mass (m/z, %): 304 (M$^+$, 37), 289 (8), 261 (4), 234 (40), 219 (64), 201 (3), 191 (100), 175 (10), 156 (5), 135 (29), 107 (11).

EXAMPLE 12

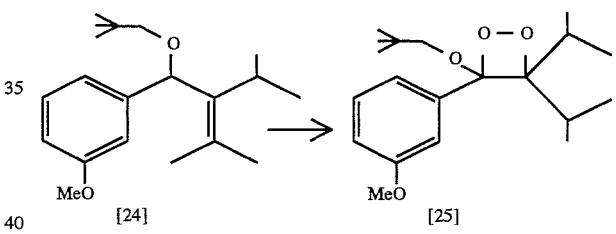

5.1 mg of tetraphenylporphine was added to a solution of 52.1 mg (0.17 mmol) of 1,1-diisopropyl-2-(3-methoxyphenyl)-2-neopentyloxyethene (Compound [24]) synthesized in Example 11 in 10 ml of dichloromethane.

This reaction solution, with vigorously stirring in the atmosphere of oxygen, was irradiated with a sodium lamp for 1 hour.

The reaction solution was concentrated, whereby 56.7 mg of a crude product was obtained. The thus obtained crude product was subjected to preparative TLC and developed with a mixed solvent of hexane and ethyl acetate (20:1), whereby 3,3-diisopropyl-4-(3-methoxyphenyl)-4-neopentyloxy-1,2-dioxetane (Compound [25]) was obtained in the form of a pale yellow oil in a yield of 44.1 mg (76.7%).

$^1$HNMR (400 MHz, CDCl$_3$): δ 0.48 (d, J=6.8 Hz, 3H), 0.91 (d, J=6.8 Hz, 3H), 0.99 (s, 9H), 1.22 (d, J=6.8 Hz, 3H), 1.35 (d, J=6.8 Hz, 3H), 2.54 (sept, J=6.8 Hz, 2H), 2.74 and 3.19 (ABq, J=8.8 Hz, 2H), 3.83 (s, 3H), 6.92–7.33 (m, 4H) ppm.

$^{13}$CNMR (400 MHz, CDCl$_3$): δ 16.52, 17.22, 18.63, 19.32, 27.07, 27.11, 29.56, 31.74, 33.51, 55.33, 72.19, 98.29, 113.85, 129.10, 137.84, 159.53 ppm.

IR (liquid film): 3080, 2959, 2875, 2837, 1727, 1601, 1585, 1478, 1470, 1387, 1365 cm$^{-1}$.

Mass (m/z, %): 304 (M⁺-32, 9), 222 (55), 166 (18), 152 (11), 135 (100), 114 (7), 107 (23).

Reference Example 7

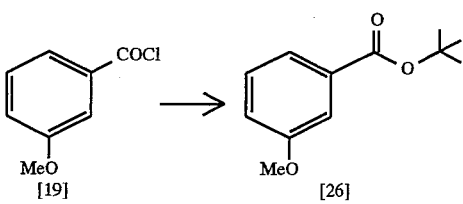

In an atmosphere of argon, a solution of 1.6 ml (11.4 mmol) of m-anisoyl chloride (Compound [19]) in 15 ml of anhydrous THF was added dropwise to an ice-cooled solution of 1.86 g (16.6 mmol) of potassium t-butoxide in 15 ml of anhydrous THF, and the reaction solution was stirred at room temperature for 6 hours.

This reaction solution was then poured into 1N hydrochloric acid. The mixture was extracted with ethyl acetate. The extracted layer was successively washed with water and with a saturated aqueous solution of sodium chloride, dried over anhydrous magnesium sulfate, and concentrated.

The residue was chromatographed on silica gel and eluted with a mixed solvent of hexane and ethyl acetate (10:1), whereby t-butyl 3-methoxybenzoate (Compound [26]) was obtained in the form of a pale yellow oil in a yield of 1.99 g (83.8%).

¹HNMR (90 MHz, CDCl₃): δ 1.52 (s, 9H), 3.77 (s, 3H), 6.92–7.58 (m, 4H) ppm.

IR (liquid film): 3405, 3090, 3005, 2978, 2936, 2837, 1714, 1602, 1587, 1488, 1450, 1393, 1368 cm⁻¹.

Mass (m/z, %): 208 (M⁺, 29), 152 (100), 135 (55).

EXAMPLE 13

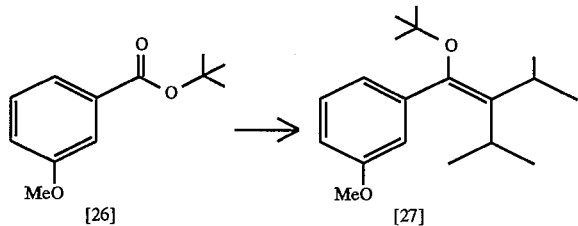

In an atmosphere of nitrogen, 4.50 g (30 mmol) of titanium trichloride was suspended in 100 ml of anhydrous THF. This suspension was stirred for 15 minutes and ice-cooled. To this ice-cooled suspension, 0.57 g (15 mmol) of lithium aluminum hydride was added.

To this reaction solution, with the temperature thereof raised to room temperature, 2.1 ml (15 mmol) of triethylamine was added, and the mixture was refluxed for 15 minutes.

To the thus refluxed mixture, a solution of 0.62 g (3 mmol) of t-butyl 3-methoxybenzoate (Compound [26]) synthesized in Reference Example 7 and 0.85 ml (6 mmol) of diisopropyl ketone in 20 of anhydrous THF was added dropwise over a period of 25 minutes. This reaction solution was further refluxed for 15 minutes.

This reaction solution was then ice-cooled and water was added dropwise thereto. The reaction mixture was then extracted with 120 ml of ethyl acetate. The extracted layer was washed with 100 ml of distilled water four times, dried over anhydrous magnesium sulfate and concentrated, whereby 0.49 g of a crude product was obtained.

The thus obtained crude product was chromatographed on silica gel, whereby 2-t-butoxy-1,1-diisopropyl-2-(3-methoxyphenyl)ethene (methoxyphenyl)ethene (Compound [27]) was obtained in the form of a colorless oil in a yield of 0.41 g (47.4%).

¹HNMR (400 MHz, CDCl₃): δ 0.88 (d, J=6.8 Hz, 6H), 1.08 (s, 9H), 1.24 (d, J=6.8 Hz, 6H), 2.40 (sept, J=6.8 Hz, 1H), 2.64 (sept, J=6.8 Hz, 1H), 3.80 (s, 3H), 6.79–7.21 (m, 4H), ppm.

¹³CNMR (400 MHz, CDCl₃): δ 21.57, 21.97, 27.04, 29.58, 29.84, 55.27, 112.83, 115.94, 123.14, 128.33, 134.83, 141.81, 145.95, 158.89 ppm.

IR (liquid film): 3080, 2958, 2870, 2835, 1731, 1620, 1596, 1577, 1485, 1464, 1389, 1364 cm⁻¹.

Mass (m/z, %), 290 (M⁺,4), 234 (47), 219 (43), 191 (100), 175 (7), 161 (3), 149 (3), 135 (40), 107 (18).

EXAMPLE 14

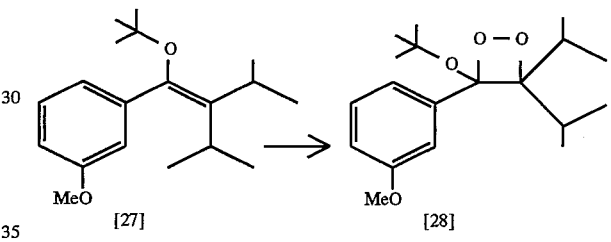

5.9 mg of tetraphenylporphine was added to a solution of 39.21 mg (0.135 mmol) of 2-t-butoxy-1,1-diisopropyl-2-(3-methoxyphenyl)ethene (Compound [27]) synthesized in Example 13 in 10 ml of dichloromethane.

This reaction solution, with vigorously stirring in the atmosphere of oxygen, was irradiated with a sodium lamp for 1 hour.

The reaction solution was concentrated, whereby 44.5 mg of a crude product was obtained. The thus obtained crude product was subjected to TLC and developed with a mixed solvent of hexane and ethyl acetate (20:1), whereby 3-t-butoxy-4,4-diisopropyl-3-(3-methoxyphenyl)-1,2-dioxetane (Compound [28]) was obtained in the form of a pale yellow oil in a yield of 30.8 mg (70.7%).

¹HNMR (400 MHz, CDCl₃): δ 0.39 (d, J=6.8 Hz, 3H), 0.88 (d, J=6.8 Hz, 3H), 1.18–1.22 (m, 12H), 1.33 (d, J=6.8 Hz, 3H), 2.44 (sept, J=6.8 Hz, 1H), 2.55 (sept, J=6.8 Hz, 1H), 3.80 (s, 1.5H), 3.85 (s, 1.5H), 6.85–7.38 (m, 4H) ppm.

¹³CNMR (400 MHz, CDCl₃): δ 16.49, 17.22, 18.73, 19.43, 29.49, 30.95, 30.99, 33.15, 33.22, 55.26, 78.34, 99.07, 113.70, 113.89, 114.18, 120.56, 128.39, 128.90, 142.53, 158.91, 159.33 ppm.

IR (liquid film): 3080, 2973, 2879, 2836, 1602, 1585, 1465, 1434, 1391, 1366 cm⁻¹.

Mass (m/z, %) 290 (M⁺-32, 1), 234 (4), 208 (30), 191 (3), 166 (2.4), 152 (100), 135 (51), 122 (3), 114 (12), 107 (17).

EXAMPLE 15

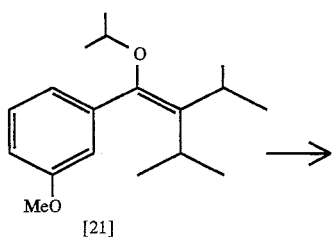

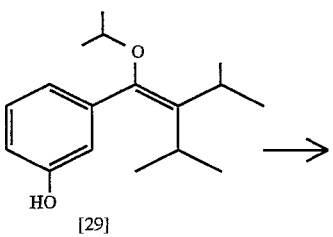

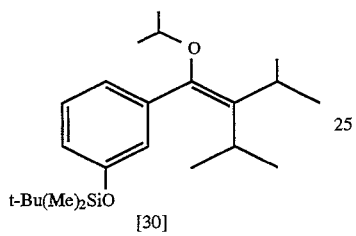

In an atmosphere of nitrogen, 0.15 ml (2.03 mmol) of ethanethiol was added to an ice-cooled suspension of 0.80 mg (2.0 mmol) of sodium hydride (60% suspension) suspended in 5 ml of anhydrous DMF, whereby a sodium salt of ethanethiol was prepared.

To the thus prepared sodium salt of ethanethiol, there was added a solution of 100 mg (0.36 mmol) of 2-isopropoxy-1,1-diisopropyl-2-(3-methoxyphenyl)ethene (Compound [21]) synthesized in Example 9 in 1 ml of anhydrous DMF.

This reaction solution was refluxed for 3 hours and was then poured into a saturated aqueous solution of ammonium chloride. This mixture was then extracted with 50 ml of ethyl acetate to obtain a first extract. The aqueous layer was again extracted with 50 ml of ethyl acetate to obtain a second extract. The first extract and the second extract were combined, and the combined extract was washed with 100 ml of a saturated aqueous solution of sodium chloride, dried over anhydrous magnesium sulfate, and concentrated.

The residue was chromatographed on silica gel and eluted with a mixed solvent of hexane and ethyl acetate (5:1), whereby 2-(3-hydroxyphenyl)-2-isopropoxy-1,1-diisopropylethene (Compound [29]) was obtained in the form of colorless crystals in a yield of 90 mg (95%).

In an atmosphere of nitrogen, the thus obtained 2-(3-hydroxyphenyl)-2-isopropoxy-1,1-diisopropylethene (Compound [29]) was dissolved in 5 ml of anhydrous DMF. To this solution, 0.3 g (2.2 mmol) of potassium carbonate and 0.3 g (2.0 mmol) of t-butyldimethylchlorosilane were added, and the mixture was stirred at room temperature overnight.

This reaction solution was poured into water and extracted with ethyl acetate. The organic layer was washed with 50 ml of a saturated aqueous solution of sodium chloride, dried over anhydrous magnesium sulfate, and concentrated.

The residue was chromatographed on silica gel and eluted with a mixed solvent to hexane and ethyl acetate (10:1), whereby 2-[3-(t-butyldimethylsiloxy)phenyl]-2-isopropoxy-1,1-diisopropylethene (Compound [30]) was obtained in the form of a colorless oil in a yield of 110 mg (85%).

$^1$HNMR (90 MHz, CDCl$_3$): δ 0.17 (s, 6H), 0.87 (d, J=7.0 Hz, 6H), 0.97 (s, 9H), 1.07 (d, J=7.0 Hz, 6H), 1.24 (d, J=7.0 Hz, 6H), 2.39 (sept, J=7.0 Hz, 2H), 3.62 (sept, J=7.0 Hz, 1H), 6.68–6.87 (m, 3H), 7.07–7.17 (m, 1H) ppm.

EXAMPLE 16

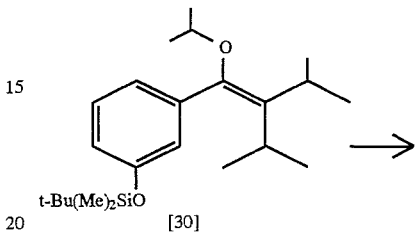

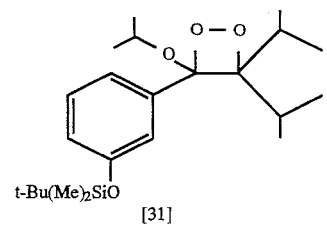

110 mg (0.29 mmol) of 2-[3-(t-butyldimethylsiloxy)-phenyl]-2-isopropoxy-1,1-diisopropylethene (Compound [30]) synthesized in Example 15 was dissolved in 10 ml of dichloromethane. To this solution, 5 mg of tetraphenylporphine was added.

This reaction solution was cooled to –78° C. and irradiated with a sodium lamp for 1 hour, with vigorously stirring in the atmosphere of oxygen.

The reaction solution was concentrated, and the residue was chromatographed on silica gel and eluted with a mixed solvent of hexane and ethyl acetate (10:1), whereby 3-[3-(t-butyldimethylsiloxy)phenyl]-3-isopropoxy-4,4-diisopropyl-1,2-dioxetane (Compound [31]) was obtained in the form of a pale yellow oil in a yield of 105 mg (88%).

$^1$HNMR (90 MHz, CDCl$_3$): δ 0.24 (s, 6H), 0.52 (d, J=7.0 Hz, 3H), 0.98 (d, J=7.0 Hz, 3H), 1.05 (s, 9H), 1.22 (d, J=7.0 Hz, 3H), 1.35 (d, J=7.0 Hz, 3H), 2.52 (sept, J=7.0 Hz, 2H), 3.64 (sept, J=7.0 Hz, 1H), 6.83–7.40 (m, 4H) ppm.

IR (liquid film): 2960, 2930, 2860, 1600, 1585, 1465, 1270, 1100, 990, 910, 810 cm$^{-1}$.

Mass (m/z, %): 376 (M$^+$-32, 68), 319 (22), 291 (35), 235 (29), 195 (100), 167 (22), 150 (31), 135 (52), 121 (26).

EXAMPLE 17

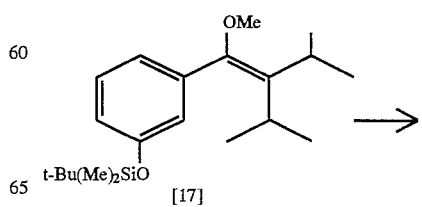

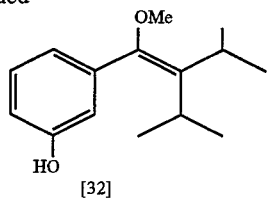

In an atmosphere of argon, 532 mg (1.53 mmol) of 2-[3-(t-butyldimethylsiloxy)phenyl]-1,1-diisopropyl-2-methoxyethene (Compound [17]) synthesized in Example 7 was dissolved in 5 ml of anhydrous THF, and this solution was ice-cooled.

To this ice-cooled solution, 1.4 ml (1.54 mmol) of a 1.1M THF solution of tetra-n-butylammonium fluoride was added, and the mixture was stirred for 2 hours.

This reaction solution was poured into a saturated aqueous solution of sodium chloride, and the mixture was extracted with ethyl acetate. The extracted layer was dried over anhydrous magnesium sulfate and concentrated.

The residue was chromatographed on silica gel and eluted with a mixed solvent of hexane and ethyl acetate (9:1), whereby 2-(3-hydroxyphenyl)-1,1-diisopropyl-2-methoxyethene (Compound [32]) was obtained in the form of colorless needles in a yield of 326 mg (91.1%).

Melting point: 76.5°–77.0° C. (recrystallized from hexane).

$^1$HNMR (300 MHz, CDCl$_3$): δ 0.92 (d, J=6.9 Hz, 6H), 1.24 (d, J=7.0 Hz, 6H), 2.31 (sept, J=7.0 Hz, 1H), 2.45 (sept, J=6.9 Hz, 1H), 3.18 (s, 3H), 4.69 (s, 1H), 6.71–6.85 (m, 3H), 7.21 (t, J=J7.8 Hz, 1H), ppm.

IR (KBr): 3332, 2960, 1596, 1444, 1222, 1058 cm$^{-1}$.

Mass (m/z, %): 234 (M$^+$, 62), 219 (80), 191 (100).

EXAMPLE 18

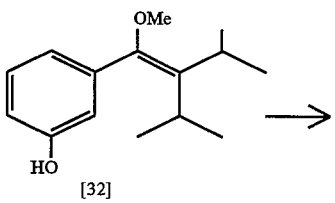

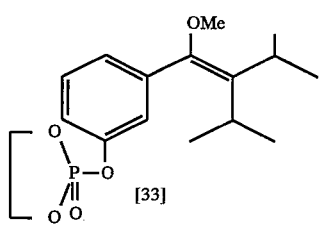

In an atmosphere of argon, to a solution of 241 mg (1.03 mmol) of 2-(3-hydroxyphenyl)-1,1-diisopropyl-2-methoxyethene (Compound [32]) synthesized in Example 17 in 3 ml of anhydrous toluene, 0.17 ml (1.22 mmol) of triethylamine and 0.093 ml (1 mmol) of 2-chloro-2-oxo-1,3,2-dioxaphosphorane were successively added at 0° C.

This reaction mixture was stirred at 0° C. for 30 minutes and then at room temperature for 3 hours, and then concentrated.

to the concentrated reaction mixture, anhydrous THF was added, and triethylamine hydrochloride was removed by filtration, and the filtrate was concentrated, whereby 3-(2,2-diisopropyl-1-methoxyethen-1-yl)phenylethylenephosphate (Compound [33]) was obtained in the form of a colorless oil.

$^1$HNMR (300 MHz, CDCl$_3$): δ 0.93 (d, J=6.8 Hz, 6H), 1.24 (d, J=7.0 Hz, 6H), 2.33 (sept, J=7.0 Hz, 1H), 2.41 (sept, J=6.8 Hz, 1H), 3.18 (s, 3H), 4.22–4.34 (m, 2H), 4.45–4.56 (m, 2H), 7.09–7.20 (m, 3H), 7.34 (t-J=7.9 Hz, 1H) ppm.

EXAMPLE 19

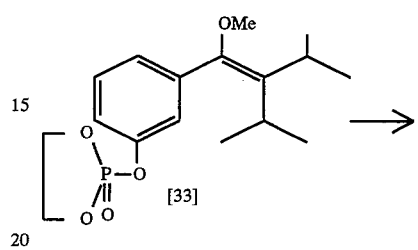

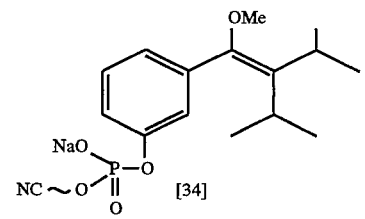

To a solution of 366 mg (1.03 mmol) of 3-(2,2-diisopropyl-1-methoxyethen-1-yl)phenylethylenephosphate (Compound [33]) synthesized in Example 18 in 4 ml of anhydrous DMF, 51 mg (1 mmol) of sodium cyanide (95%) was added in an atmosphere of argon.

This reaction mixture was stirred at room temperature for 21 hours. The reaction solvent was then removed from the reaction mixture in vacuum at 60° C., and 5 ml of anhydrous xylene was added to the reaction mixture tow times, and the solvent was removed in vacuum.

To the residue, water was added, and the mixture was extracted with hexane. The aqueous layer was subjected to freeze-drying, whereby sodium 3-(2,2-diisopropyl-1-methoxyethen-1-yl)phenyl-2-cyanoethylphosphate (Compound [34]) was obtained in the form of a pale yellow amorphous solid in a yield of 338 mg.

$^1$HNMR (300 MHz, CD$_3$OD): δ 0.97 (d, J=6.8 Hz, 6H), 1.29 (d, J=7.0 Hz, 6H), 2.36 (sept, J=7.0 Hz, 1H), 2.52 (sept, J=6.8 Hz, 1H), 2.80 (t, J=6.2 Hz, 2H, 3.23 (s, 3H), 4.15 (dt, J=7.8 and 6.2 Hz, 2H), 6.98 (d, J=7.4 Hz, 1H), 7.15 (s with fine coupling, 1H), 7.23–7.29 (m, 1H), 7.33 (t, J=7.4 Hz, 1H) ppm.

EXAMPLE 20

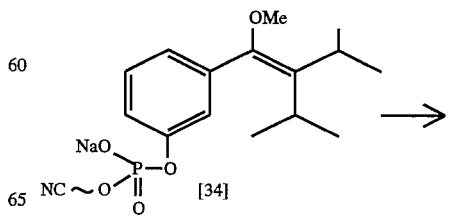

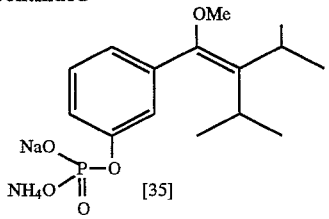

To an aqueous solution of 338 mg (0.87 mmol) of sodium 3-(2,2-diisopropyl-1-methoxyethen-1-yl)phenyl-2'-cyanoethylphosphate (Compound [34]) synthesized in Example 19 in 2 ml of water, 4 ml of 28% ammonia water was added in an atmosphere of argon.

This reaction mixture was stirred at room temperature for 24 hours, and then extracted with the addition of hexane thereto. The aqueous layer was subjected to freeze-drying, whereby ammonium sodium 3-(2,2-diisopropyl-1-methoxyethen-1-yl)phenylphosphate (Compound [35]) was obtained in the form of a colorless amorphous solid in a yield of 285 mg.

$^1$HNMR (300 MHz, CD$_3$OD): δ 0.96 (d, J=6.8 Hz, 6H), 1.28 (d, J=7.0 Hz, 6H), 2.35 (sept, J=7.0 Hz, 1H), 2.54 (sept, J=6.8 Hz, 1H), 3.22 (s, 3H), 6.91 (d with fine coupling, J=6.8 Hz, 1H), 7.14 (s, 1H), 7.25–7.36 (m, 2H) ppm.

IR (KBr): 2960, 2828, 1601, 1427, 1280, 1118 cm$^{-1}$.

Mass (FAB-pos, m/z, %): 381 ([M-NH$_4$+2Na]$^+$, 30), 359 (100), 337 (63), 125 (60), 115 (52).

EXAMPLE 21

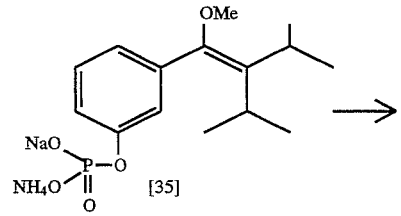

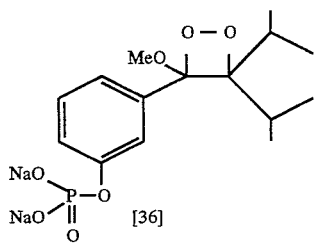

100 mg (0.28 mmol) of ammonium sodium 3-(2,2-diisopropyl-1-methoxyethen-1-yl)phenylphosphate (Compound [35]) synthesized in Example 20 and 5 mg of tetraphenylporphine were dissolved in a mixed solvent of 20 ml of dichloromethane and 5 ml of methanol.

This solution was ice-cooled and, with stirring in the atmosphere of oxygen, irradiated with a sodium lamp (180 W) for 4 hours.

The reaction mixture was concentrated, and methanol was added thereto. Insoluble components were removed from the mixture by filtration, and the filtrate was again concentrated.

The residue was dissolved in a mixed solvent composed of 1 ml of methanol and 1 ml of a 0.1% aqueous solution of sodium hydrogencarbonate, and filtered through a 0.45 μ polytetrafluoroethylene filter.

The filtrate was subjected to HPLC using an octadecyl group introduced polymeric reversed phase column, and a fraction which was eluted with a gradient elution by using a 0.1% aqueous solution of sodium hydrogencarbonate and acetonitrile was subjected to freeze-drying, whereby a freeze-dried product was obtained.

The thus obtained freeze-dried product was dissolved in water, and subjected to HPLC using an octadecyl group introduced polymeric reversed phase column, and a fraction which was desalted by a gradient elution by using water and acetonitrile was subjected to freeze-drying, whereby 3,3-diisopropyl-4-methoxy-4-[(3'-phosphoryloxy)phenyl]-1,2-dioxetane disodium salt (Compound [36]) was obtained in the form of an amorphous solid in a yield of 48 mg.

$^1$HNMR (300 MHz, CD$_3$OD): δ 0.51 (d, J=7.1 Hz, 3H), 0.92 (d, J=6.9 Hz, 3H), 1.22 (d, J=6.9 Hz, 3H), 1.32 (d, J=7.1 Hz, 3H), 2.43 (sept, J=7.1 Hz, 1H), 2.67 (sept, J=6.9 Hz, 1H), 3.14 (s, 3H), 7.00–7.30 (m, 2H), 7.33 (t, J=7.8 Hz, 1H), 7.60–7.70 (m, 1H), ppm.

IR (KBr): 2972, 1280, 1138, 1116 cm$^{-1}$.

Mass (FAB-pos, m/z, %): 391 ([M+H]$^+$,23), 299 (19), 277 (24), 115 (100).

EXAMPLE 22

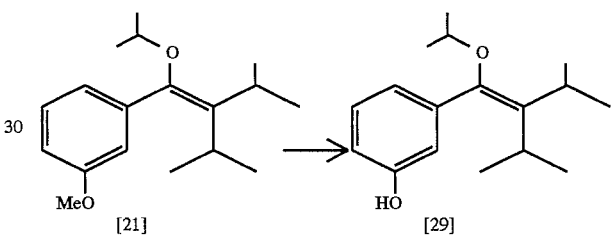

In an atmosphere of argon, 0.38 ml (5.14 mmol) of ethanethiol was added to an ice-cooled suspension of 195 mg (4.89 mmol) of sodium hydride (60% suspension) suspended in 6 ml of anhydrous DMF.

To the above mixture, with the temperature thereof raised to room temperature, there was added dropwise a solution of 710 mg (2.57 mmol) of 2-isopropoxy-1,1-diisopropyl-2-(3-methoxyphenyl)ethene (Compound [21]) synthesized in Example 9 in 3 ml of anhydrous DMF.

This reaction mixture was refluxed for 3 hours and 45 minutes and was then poured into a saturated aqueous solution of ammonium chloride. This mixture was then extracted with ethyl acetate. The extracted layer was washed with a saturated aqueous solution of sodium chloride, dried over anhydrous magnesium sulfate, and concentrated.

The residue was chromatographed on silica gel and eluted with a mixed solvent of hexane and ethyl acetate (9:1), whereby 2-(3-hydroxyphenyl)-2-isopropoxy-1,1-diisopropylethene (Compound [29]) was obtained in the form of colorless needles in a yield of 571 mg (84.8%).

Melting point: 83.0°–84.0° C. (recrystallized from hexane).

$^1$HNMR (300 MHz, CDCl$_3$): δ 0.89 (d, J=7.0 Hz, 6H), 1.08 (d, J=6.2 Hz, 6H), 1.25 (d, J=7.0 Hz, 6H), 2.41 (sept, J=7.0 Hz, 2H), 3.64 (sept, J=6.2 Hz, 1H), 4.69 (s, 1H), 6.72 (s with fine coupling, 1H), 6.75 (d with fine coupling, J=7.8 Hz, 1H), 6.82 (d, J=7.8 Hz, 1H), 7.20 (t, J=7.8 Hz, 1H) ppm.

IR (KBr): 3328, 2964, 2928, 1616, 1580, 1488, 1284, 1188 cm$^{-1}$.

Mass (m/z, %): 262 (M$^+$,38), 220 (11), 205 (44), 177 (100).

EXAMPLE 23

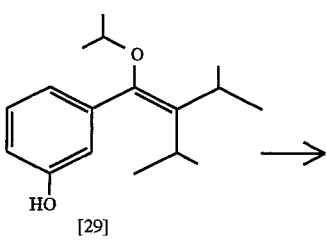

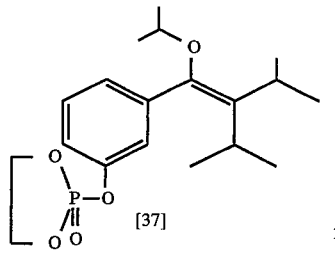

In an atmosphere of argon, to a solution of 291 mg (1.11 mmol) of 2-(3-hydroxyphenyl)-2-isopropoxy-1,1-diisopropylethene (Compound [29]) synthesized in Example 22 in 3 ml of anhydrous toluene, 0.19 ml (1.36 mmol) of triethylamine and 0.1 ml (1.08 mmol) of 2-chloro-2-oxo-1,3,2-dioxaphosphorane were successively added at 0° C.

This reaction mixture was stirred at 0° C. for 30 minutes and then at room temperature for 2 hours, and then concentrated.

To the concentrated reaction mixture, anhydrous THF was added, and triethylamine hydrochloride was removed by filtration, and the filtrate was concentrated, whereby 3-(1-isopropoxy-2,2-diisopropylethen-1-yl) phenylethylenephosphate (Compound [37]) was obtained in the form of a colorless amorphous solid.

$^1$HNMR (300 MHz, CD$_3$OD): δ 0.90 (d, J=6.9 Hz, 6H), 1.25 (d, J=7.0 Hz, 6H), 1.49 (d, J=6.1 Hz, 6H), 2.35–2.50 (m, 2H), 3.59 (sept, J=6.1 Hz, 1H), 4.22–4.32 (m, 2H), 4.45–4.57 (m, 2H), 7.07–7.20 (m, 3H), 7.29 (m, 1H) ppm.

EXAMPLE 24

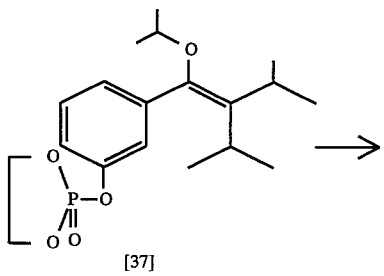

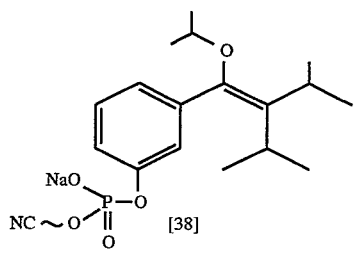

To a solution of 412 mg (1.11 mmol) of 3-(1-isopropoxy-2,2-diisopropylethen-1-yl)phenylethylenephosphate (Compound [37]) synthesized in Example 23 in 4 ml of anhydrous DMF, 57 mg (1.1 mmol) of sodium cyanide (95%) was added in an atmosphere of argon.

This reaction mixture was stirred at room temperature for 15 hours. The reaction solvent was then removed from the reaction mixture in vacuum at 60° C., and 5 ml of anhydrous xylene was added to the reaction mixture two times, and the solvent was removed in vacuum.

To the residue, water was added, and the mixture was extracted with hexane. The aqueous layer was subjected to freeze-drying, whereby sodium 3-(1-isopropoxy-2,2-diisopropylethen-1-yl)phenyl-2'-cyanoethylphosphate (Compound [38]) was obtained in the form of a pale yellow amorphous solid in a yield of 383 mg.

$^1$HNMR (300 MHz, CD$_3$OD): δ 0.94 (d, J=6.9 Hz, 6H), 1.12 (d, J=6.2 Hz, 6H), 1.31 (d, J=7.1 Hz, 6H), 2.37–2.56 (m, 2H), 2.79 (t, J=6.2 Hz, 2H), 3.72 (sept, J=6.2 Hz, 1H), 4.14 (dt, J=7.8 and 6.2 Hz, 2H), 6.98 (d, J=7.1 Hz, 1H), 7.13 (s, 1H), 7.22–7.36 (m, 2H) ppm.

IR (KBr: 2962, 2930, 2262, 1600, 1575, 1482, 1259, 1121, 1107 cm$^{-1}$.

Mass (FAB-pos, m/z, %): 440 ([M+Na]$^+$,100), 418 ([M+H]$^+$, 35), 382 (72), 360 (29).

EXAMPLE 25

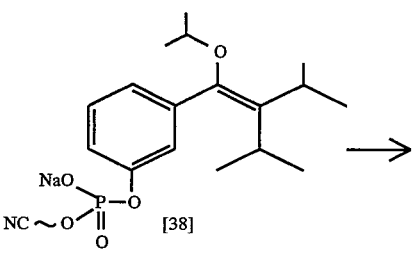

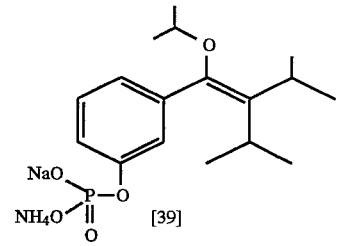

To an aqueous solution of 340 mg (0.82 mmol) of sodium 3-(1-isopropoxy-2,2-diisopropylethen-1-yl)phenyl-2'-cyanoethylphosphate (Compound [38]) synthesized in Example 24 in 2 ml of water, 4 ml of 38% ammonia water was added in an atmosphere of argon.

This reaction mixture was stirred at room temperature for 24 hours, and then extracted with the addition of hexane thereto. The aqueous layer was subjected to freeze-drying, whereby ammonium sodium 3-(1-isopropoxy-2,2-diisopropylethen-1-yl)phenylphosphate (Compound [39]) was obtained in the form of a colorless amorphous solid in a yield of 327 mg.

$^1$HNMR (300 MHz, CD$_3$OD): δ 0.93 (d, J=6.9 Hz, 6H), 1.12 (d, J=6.1 Hz, 6H), 1.31 (d, J=7.0 Hz, 6H), 2.43 (sept, J=7.0 Hz, 1H).. 2.50 (sept, J=6.9 Hz, 1H), 3.74 (sept, J=6.1 Hz, 1H), 6.91 (d, J=6.8 Hz, 1H), 7.10 (s, 1H), 7.24–7.40 (m, 2H), ppm.

IR (KBr): 2962, 2928, 1599, 1577, 1481, 1426, 1279, 1139, 1122, 1108 cm$^{-1}$.

EXAMPLE 26

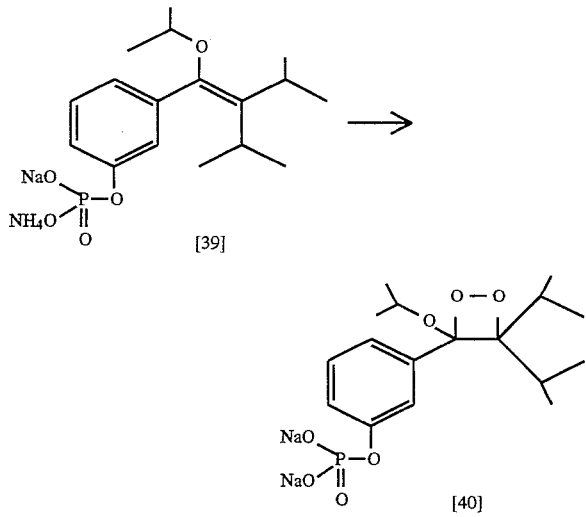

164 mg (0.43 mmol) of ammonium sodium 3-(1-isopropoxy-2,2-diisopropylethen-1-yl)phenylphosphate (Compound [39]) synthesized in Example 25 and 5 mg of tetraphenylporphine were dissolved in a mixed solvent of 25 ml of dichloromethane and 5 ml of methanol.

This solution was ice-cooled and, with stirring in the atmosphere of oxygen, inrradiated with a sodium lamp (180 W) for 4 hours.

The reaction mixture was concentrated and methanol was added thereto. Insoluble components were removed from the mixture by filtration, and the filtrate was again concentrated.

The residue was dissolved in a mixed solvent composed of 1 ml of methanol and 1 ml of a 0.1% aqueous solution of sodium hydrogencarbonate, and filtered through a 0.45 μ polytetrafluoroethylene filter.

The filtrate was subjected to HPLC using an octadecyl group introduced polymeric reversed phase column, and a fraction which was eluted with a gradient elution by using a 0.1% aqueous solution of sodium hydrogencarbonate and acetonitrile was subjected to freeze-drying, whereby a freeze-dried product was obtained.

The thus obtained freeze-dried product was dissolved in water, and subjected to HPLC suing an octadecyl group introduced polymeric reversed phase column, and a fraction which was desalted by a gradient elution by using water and acetonitrile was subjected to freeze-drying, whereby 3-isopropoxy-4,4-diisopropyl-3-(3'-phosphoryloxy)phenyl-1,2-dioxetane disodium salt (Compound [40]) was obtained in the form of an amorphous solid in a yield of 77 mg.

$^1$HNMR (300 MHz, $CD_3OD$): δ 0.43–0.60 (m, 3H), 0.88 (d, J=6.8 Hz, 3H), 1.06–1.20 (m, 3H), 1.26 (d, J=7.1 Hz, 3H)), 1.29 (d, J=6.8 Hz, 3H), 1.38 (d, J=7.1 Hz, 3H), 2.40 (sept, J=7.1 Hz, 1H), 2.46–2.64 (m, 1H), 3.56–3.70 (m, 1H), 6.80–7.70 (m, 4H), ppm.

IR (KBr): 2976, 1586, 1484, 1278, 1142, 1104 $cm^{-1}$.

Mass (FAB-pos, m/z, %): 441 ([M+Na]$^+$, 25), 419 ([M+H]$^+$, 38), 327 (26), 305 (44), 115 (100).

Mass (FAB-pos, m/z, %): 387 ([M+H=$NH_4$+Na]$^+$, 100), 329 (59), 125 (53), 115 (43).

Reference Example 8

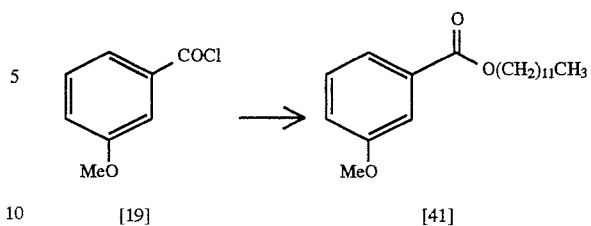

In an atmosphere of argon, a solution of 1.4 ml (10 mmol) of m-anisoyl chloride (Compound [19]) in 5 ml of dichloroethane was added dropwise to a solution of 6.8 ml (30 mmol) of 1-dodecanol and 0.81 ml (10 mmol) of pyridine in 5 ml of dichloroethane, and this reaction mixture was refluxed for 3 hours and 45 minutes.

The reaction mixture was then poured into 1N hydrochloric acid. The mixture was extracted with ethyl acetate. The extracted organic layer was successively washed with a saturated aqueous solution of sodium hydrogencarbonate and with a saturated aqueous solution of sodium chloride, dried over anhydrous magnesium sulfate, and concentrated.

The residue was chromatographed on silica gel and eluted with a mixed solvent of hexane and ethyl acetate (10:1), whereby dodecyl 3-methoxybenzoate (Compound [419 ) was obtained in the form of a colorless oil quantitatively.

$^1$HNMR (300 MHz, $CDCl_3$): δ 0.88 (t, J=6.7 Hz), 1.20–1.50 (m, 18H), 1.76 (quint, J=6.7 Hz, 2H), 3.86 (s, 3H), 4.31 (t, J=6.7 Hz, 2H), 7.10 (ddd, J=3H), 4.31 (t, J=6.7 Hz, 2H), 7.34 (t, J=8.0 Hz, 1H), 7.56 (s with fine coupling, 1H), 7.64 (d with fine coupling, J=8.0 Hz, 1H) ppm.

IR (liquid film): 2928, 2856, 1724, 1602, 1588, 1280, 1230 $cm^{-1}$. Mass (m/z, %): 320 ($M^+$, 29), 153 (26), 152 (100), 135 (28).

EXAMPLE 27

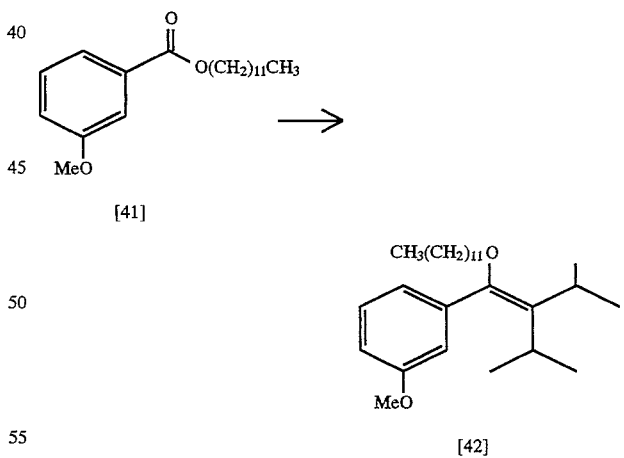

In an atmosphere of argon, 5 g (32 mmol) of titanium trichloride was suspended in 100 ml of anhydrous THF. This suspension was stirred for 15 minutes and ice-cooled. To this ice-cooled suspension, 608 mg (16 mmol) of lithium aluminum hydride was added, and this mixture was stirred for 20 minutes.

To this reaction mixture, with the temperature thereof raised to room temperature, 2.3 ml (16 mmol) of triethylamine was added, and the mixture was refluxed for 20 minutes.

To the thus refluxed mixture, a solution of 1.024 g (3.2 mmol) of dodecyl 3-methoxybenzoate (Compound [41]) synthesized in Reference Example 8 and 0.95 ml (6.7 mmol) of diisopropyl ketone in 20 ml of anhydrous THF was added dropwise over a period of 30 minutes. This reaction mixture was further refluxed for 30 minutes.

This reaction mixture was then ice-cooled and water was added dropwise thereto. The reaction mixture was then extracted with ethyl acetate. The extracted layer was successively washed with water, a saturated aqueous solution of sodium hydrogencarbonate and a saturated aqueous solution of sodium chloride, dried over anhydrous magnesium sulfate and concentrated.

The residue was chromatographed on silica gel and eluted with a mixed solvent of hexane and dichloromethane (6:1), whereby 2-dodecanoxy-1,1-diisopropyl-2-(3-methoxyphenyl)ethene (Compound [42]) was obtained in the form of a colorless oil in a yield of 654 mg (50.8%).
$^1$HNMR (300 MHz, CDCl$_3$): δ 0.88 (T, J=7.0 Hz, 3H), 0.91 (d, J=6.9 Hz, 6H), 1.16–1.26 (m, 24 H), 1.49–1.61 (m, 2H), 2.33 (sept, J=6.9 Hz, 1H), 2.44 (sept, J=6.8 Hz, 1H), 3.24 (t, J=6.7 Hz, 2H), 3.81 (s, 3H), 6.79 (s with fine coupling, 2H), 6.82 (d, J=7.8 Hz, 1H), 6.83 (d, J=7.8 Hz, 1H), 7.24 (t, J=7.8 Hz, 1H) ppm.

IR (liquid film): 2960, 2928, 1598, 1578, 1466, 1286 cm$^{-1}$.

Mass (m/z, %): 402 (M$^+$, 100), 387 (39), 359 (20), 219 (75), 191 (62), 135 (36).

EXAMPLE 28

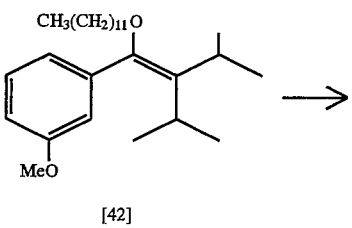

[42]

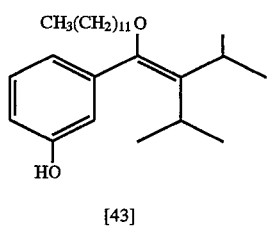

[43]

In an atmosphere of argon, 0.43 ml (5.8 mmol) of ethanethiol was added to an ice-cooled suspension of 220 mg (5.51 mmol) of sodium hydride (60% suspension) suspended in 10 ml of anhydrous DMF, and this mixture was stirred for 10 minutes.

To the above mixture, with the temperature thereof raised to room temperature, there was added dropwise a solution of 1.185 g (2.9 mmol) of 2-dodecanoxy-1,1-diisopropyl-2-(3-methoxyphenyl)ethene (Compound [42]) synthesized in Example 27 in 5 ml of anhydrous DMF.

This reaction mixture was refluxed for 3 hours and 40 minutes and was then poured into a saturated aqueous solution of ammonium chloride. This mixture was then extracted with ethyl acetate. The extracted layer was washed with a saturated aqueous solution of sodium chloride, dried over anhydrous magnesium sulfate, and concentrated.

The residue was chromatographed on silica gel and eluted with a mixed solvent of hexane and ethyl acetate (10:1), whereby 2-dodecanoxy-2-(3-hydroxyphenyl)-1,1-diisopropylethene (Compound [43]) was obtained in the form of a colorless oil in a yield of 1.002 g (89.1%).

$^1$HNMR (300 MHz, CDCl$_3$): δ 0.88 (d, J=7.0 Hz, 3H), 0.91 (d, J=6.8 Hz, 6H), 1.20–1.38 (m, 22H), 1.49–1.61 (m, 4H), 2.32 (sept, J=7.0 Hz, 1H), 2.44 (sept, J=6.8 Hz, 1H), 3.23 (t, J=6.7 Hz, 2H), 4.67 (s, 1H), 6.72 (s with fine coupling, 1H), 6.76 (d with fine coupling, J=7.8 Hz, 1H), 6.82 (d with fine coupling, J=7.8 Hz, 1H), 7.20 (t, J=7.8 Hz, 1H), ppm.

IR (liquid film): 3384, 2928, 2856, 1582, 1446, 1284, 1226 cm$^{-1}$.

Mass (m/z, %): 388 (M$^+$, 100), 373 (37), 345 (24), 205 (79), 177 (83), 121 (36).

EXAMPLE 29

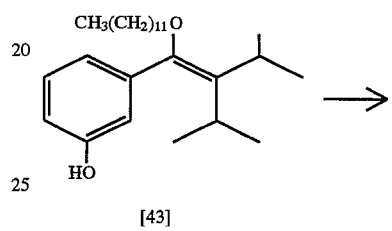

[43]

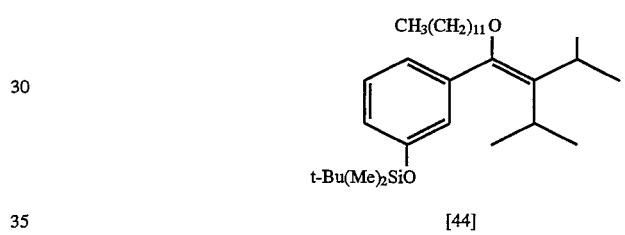

[44]

In an atmosphere of argon, 349 mg (0.9 mmol) of 2-dodecanoxy-2-(3-hydroxyphenyl)-1,1-diisopropylethen (Compound [43]) synthesized in Example 28 was dissolved in 3 ml of anhydrous DMF.

To this solution, 73 mg (1.08 mmol) of imidazole and 168 mg (1.11 mmol) of t-butyldimethylchlorosilane were successively added, and the solution was stirred at room temperature for 4 hours.

This reaction solution was poured into a saturated aqueous solution of sodium chloride and extracted with ethyl acetate. The extracted layer was dried over anhydrous magnesium sulfate and concentrated.

The residue was chromatographed on silica gel and eluted with a mixed solvent of hexane and dichloromethane (10:1), whereby 2-[3-(t-butyldimethylsiloxy)phenyl]-2-dodecanoxy-1,1-diisopropylethene (Compound [44]) was obtained in the form of a colorless oil in a yield of 277 mg (61.3%).

$^1$HNMR (300 MHz, CDCl$_3$): δ 0.18 (s, 6H), 0.87 (t, J=7.0 Hz, 3H), 0.96 (d, J=6.9 Hz, 6H), 0.98 (s, 9H), 1.13–1.35 (m, 24H), 1.48–1.60 (m, 2H), 2.31 (sept, J=7.0 Hz, 1H), 2.43 (sept, J=6.9 Hz, 1H), 3.22 (t, J=6.8 Hz, 2H), 6.72 (s with fine coupling, 1H), 6.75 . 6.79 (m, 1H), 6.79–6.86 (m, 1H), 7.17 (t, J=7.8 Hz, 1H), ppm.

IR (liquid film): 2928, 2860, 1596, 1578, 1484, 1286 cm$^{-1}$.

Mass (m/z, %): 502 (M$^+$, 100), 487 (25), 319 (39), 291 (26), 235 (15).

EXAMPLE 30

[Structure of Compound [44]: CH₃(CH₂)₁₁O and t-Bu(Me)₂SiO substituted benzene with diisopropyl alkene]

[44] → [45]

[Structure of Compound [45]: dioxetane with CH₃(CH₂)₁₁O, t-Bu(Me)₂SiO-phenyl, and diisopropyl groups]

100 mg (0.2 mmol) of 2-[3-(t-butyldimethylsiloxy)-phenyl]-2-dodecanoxy-1,1-diisopropylethene (Compound [44]) synthesized in Example 29 was dissolved in 20 ml of dichloromethane. To this solution, 6 mg of tetraphenylporphine was added.

This mixture was ice-cooled and irradiated with a sodium lamp (180 W) in an atmosphere of oxygen for 2 hours.

The reaction mixture was concentrated, and the residue was chromatographed on silica gel and eluted with a mixed solvent of hexane and ether (20:1), whereby a crude product was obtained.

This crude product was then subjected to preparative TLC, developed with a mixed solvent of hexane and ether (20:1), and eluted with dichloromethane, whereby 3-[3-(t-butyldimethylsiloxy)phenyl]-3-dodecanoxy-4,4-diisopropyl-1,2-dioxetane (Compound [45]) was obtained in the form of a colorless oil in a yield of 51 mg (47.8%).

¹HNMR (300 MHz, CDCl₃): δ 0.20 (s, 6H), 0.45 (d, J=7.2 Hz, 3H), 0.89 (t, J=6.9 Hz, 3H), 0.91 (d, J=6.8 Hz, 3H), 0.99 (s, 9H), 1.21 (d, J=6.8 Hz, 3H), 1.24–1.31 (m, 18H), 1.33 (d, J=7.2 Hz, 3H), 1.58–1.70 (m, 2H), 2.41 (sept, J=7.2 Hz, 1H), 2.58 (sept, J=6.8 Hz, 1H), 3.02 (dt, J=9.1 and 6.7 Hz, 1H), 3.49 (dt, J=9.1 and 6.4 Hz, 1H), 6.70–7.40 (m, 4H), ppm.

IR (liquid film): 2932, 2860, 1600, 1584, 1474, 1290, 1256 cm⁻¹.

Mass (m/z, %): 503 (M⁻-31, 2), 420 (39), 363 (100).

Reference Example 9

[Structure: m-anisoyl chloride [19] → ester compound [46]]

In an atmosphere of argon, a solution of 1.4 ml (10 mmol) of m-anisoyl chloride (Compound [199]) in 5 ml of dichloroethane was added dropwise to a solution of 5.7 ml (29.8 mmol) of 2-decanol and 0.81 ml (10 mmol) of pyridine in 5 ml of dichloroethane, and this reaction mixture was refluxed for 2 hours and 20 minutes.

The reaction mixture was then poured into 1N hydrochloric acid. The mixture was extracted with ethyl acetate. The extracted organic layer was successively washed with a saturated aqueous solution of sodium hydrogencarbonate and with a saturated aqueous solution of sodium chloride, dried over anhydrous magnesium sulfate and concentrated.

The residue was chromatographed on silica gel and eluted with a mixed solvent of hexane and ethyl acetate (9:1), whereby (2-decyl) 3-methoxybenzoate (Compound [46]) was obtained in the form of a colorless oil quantitatively.

¹HNMR (300 MHz, CDCl₃): δ 0.87 (t, J=6.7 Hz, 3H), 1.17–1.46 (m, 12H), 1.33 (d, J=6.3 Hz, 3H), 1.50–1.66 (m, 1H), 1.66–1.81 (m, 1H), 3.86 (s, 3H), 5.08–5.21 (m, 1H), 7.09 (dd with fine coupling, J=8.0 and 2.4 Hz, 1H), 7.34 (t, J=8.0 Hz, 1H), 7.56 (s with fine coupling, 1H), 7.64 (d with fine coupling, J=8.0 Hz, 1H) ppm.

IR (liquid film): 2932, 2860, 1720, 1602, 1588, 1468, 1280, 1232 cm⁻¹.

Mass (m/z, %): 292 (M⁺, 21), 153 (30), 152 (100), 135 (73).

EXAMPLE 31

[Structure of Compound [46]: 3-methoxybenzoate ester with 2-decyl group]

[46] → [47]

[Structure of Compound [47]: alkene with H₃C(CH₂)₇, HC—O, MeO-phenyl, and diisopropyl groups]

In an atmosphere of argon, 10 g (64 mmol) of titanium trichloride was suspended in 200 ml of anhydrous THF. This suspension was stirred for 10 minutes and ice-cooled. To this ice-cooled suspension, 1.26 g (33.2 mmol) of lithium aluminum hydride was added.

To this reaction mixture, with the temperature thereof raised to room temperature, 4.6 ml (32 mmol) of triethylamine was added, and the mixture was refluxed for 15 minutes.

To the thus refluxed mixture, a solution of 1.87 g (6.4 mmol) of (2-decyl) 3-methoxybenzoate (Compound [46]) synthesized in Reference Example 9 and 1.9 ml (13.4 mmol) of diisopropyl ketone in 40 ml of anhydrous THF was added dropwise over a period of 30 minutes. This reaction mixture was further refluxed for 30 minutes.

This reaction solution was then ice-cooled and water was added dropwise thereto. The reaction mixture was then extracted with ethyl acetate. The extracted layer was successively washed with water, a saturated aqueous solution of sodium hydrogencarbonate and a saturated aqueous solution of sodium chloride, dried over anhydrous magnesium sulfate and concentrated.

The residue was chromatographed on silica gel and eluted with a mixed solvent of hexane and dichloromethane (6:1), whereby 2-(2-decanoxy)-1,1-diisopropyl-2-(3-methoxyphenyl)ethene (Compound [47]) was obtained in the form of a colorless oil in a yield of 1.071 g (44.7%).

¹HNMR (300 MHz, CDCl₃): δ 0.85 (d, J=6.9 Hz, 6H), 0.88 (t, J=6.7 Hz, 3H), 0.93 (d, J=6.9 Hz, 6H), 1.01 (d, J=6.2 Hz, 3H), 1.14–1.41 (m, 12H), 1.50–1.65 (m, 1H), 3.81 (s, 3H), 6.74–6.78 (m, 1H), 6.78–6.86 (m, 2H), 7.23 (t, J=7.7 Hz, 1H) ppm.

IR (liquid film): 2960, 2928, 1596, 1578, 1430, 1286, 1230 cm⁻¹.

Mass (m/z, %): 374 (M⁺, 21), 234 (61), 219 (36), 191 (100), 135 (35).

EXAMPLE 32

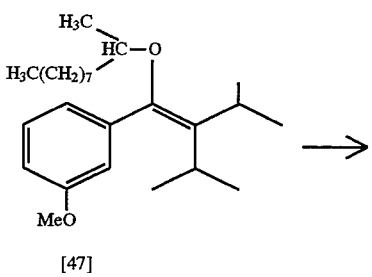

[47]

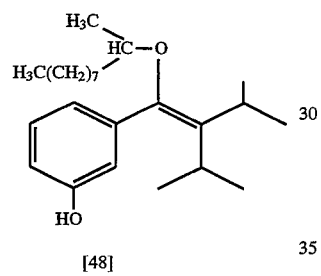

[48]

In an atmosphere of argon, 0.365 ml (4.94 mmol) of ethanethiol was added to an ice-cooled suspension of 187 mg (4.69 mmol) of sodium hydride (60% suspension) suspended in 6 ml of anhydrous DMF, and the mixture was stirred for 10 minutes.

To the above mixture, with the temperature thereof raised to room temperature, there was added dropwise a solution of 972 mg (2.6 mmol) of 2-(2-decanoxy)-1,1-diisopropyl-2-(3-methoxyphenyl)ethene (Compound [47]) synthesized in Example 31 in 4 ml of anhydrous DMF.

This reaction solution was refluxed for 4 hours and was then poured into a saturated aqueous solution of ammonium chloride. This mixture was then extracted with ethyl acetate. The extracted layer was washed with a saturated aqueous solution of sodium chloride, dried over anhydrous magnesium sulfate, and concentrated.

The residue was chromatographed on silica gel and eluted with a mixed solvent of hexane and ethyl acetate (10:1), whereby 2-(2-decanoxy)-2-(3-hydroxyphenyl)-1,1-diisopropylethene (Compound [48]) was obtained in the form of a colorless oil in a yield of 907 mg (96.9%).

¹HNMR (300 Hz, CDCl₃): δ 0.85 (d, J=6.8 Hz, 6H), 0.88 (t, J=6.6 Hz, 3H), 0.92 (d, J=7.0 Hz, 3H), 1.01 (d, J=6.1 Hz, 3H), 1.13–1.41 (m, 15H), 1.49–1.65 (m, 2H), 2.38 (sept, J=7.0 Hz, 1H), 2.39 (sept, J=6.8 Hz, 1H), 3.38–3.50 (m, 1H), 3.70 (s, 1H), 6.69 (s, 1H), 6.71–6.83 (m, 2H), 7.19 (t, J=7.8 Hz, 1H) ppm.

IR (liquid film): 3392, 2960, 2928, 1582, 1448, 1284, 1120 cm⁻¹.

Mass (m/z, %): 360 (M⁺, 16), 220 (42), 205 (28), 177 (100).

EXAMPLE 33

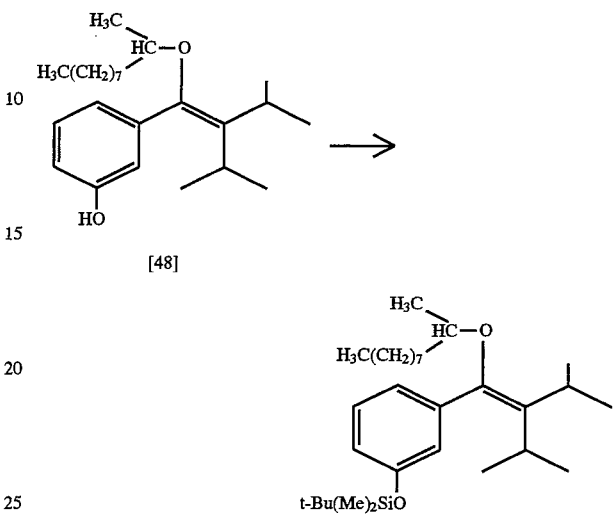

[48]

[49]

In an atmosphere of argon, 257 mg (0.714 mmol) of 2-(2-decanoxy)-2-(3-hydroxyphenyl)-1,1-diisopropylethene (Compound [48]) synthesized in Example 32 was dissolved in 3 ml of anhydrous DMF.

To this solution, 57 mg (0.85 mmol) of imidazole and 130 mg (0.85 mmol) of t-butyldimethylchlorosilane were successively added, and the mixture was stirred at room temperature for 4 hours and 30 minutes.

This reaction mixture was poured into a saturated aqueous solution of sodium chloride and extracted with ethyl acetate. The extracted layer was dried over anhydrous magnesium sulfate and concentrated.

The residue was chromatographed on silica gel and eluted with a mixed solvent of hexane and dichloromethane (10:1), whereby 2-[-(t-butyldimethylsiloxy)phenyl]-2-(2-decanoxy)-1,2-diisopropylethene (Compound [49]) was obtained in the form of a colorless oil in a yield of 266 mg (78.6%).

¹HNMR (300 MHz, CDCl₃): δ 0.20 (s, 6H), 0.86 (t, J=7.2 Hz, 3H), 0.92 (d, J=6.9 Hz, 6H), 0.99 (s, 9H), 1.02 (d, J=6.2 Hz, 3H), 1.12–1.40 (m, 18H), 1.48–1.62 (m, 2), 2.39 (sept, J=6.9 Hz, 2H), 3.38–3.50 (m, 1H), 6.70 (s with fine coupling, 1H), 6.74–6.82 (m, 2H), 7.18 (t, J=7.8 Hz, 1H) ppm.

IR (liquid film): 2960, 2932, 2860, 1596, 1578, 1482, 1424, 1286 cm⁻¹.

Mass (m/z, %): 474 (M⁺, 42), 334 (100), 291 (88), 235 (23).

EXAMPLE 34

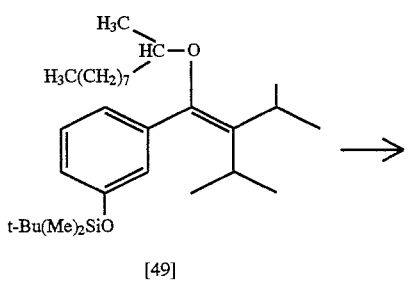

[49]

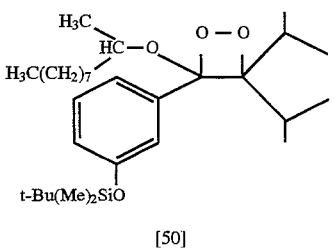

[50]

115 mg (0.24 mmol) of 2-]3-(t-butyldimethylsiloxy)-phenyl]-2-(2-decanoxy)-1,1-diisopropylethene (Compound [49]) synthesized in Example 33 was dissolved in 20 ml of dichloromethane. To this solution, 6 mg of tetraphenylporphine was added.

This mixture was ice-cooled and irradiated with a sodium lamp (180 W) in an atmosphere of oxygen for 2 hours.

The reaction mixture was concentrated, and the residue was chromatographed on silica gel and eluted with a mixed solvent of hexane and ether (20:1), whereby a crude product was obtained.

This crude product was then subjected to preparative TLC, developed with a mixed solvent of hexane and ether (50:1), and eluted with dichloromethane, whereby 3-[3-(t-butyldimethylsiloxy)phenyl]-3-(2-decanoxy)-4,4-diisopropyl-1,2-dioxetane (Compound [50]) was obtained in the form of a colorless oil in a yield of 49 mg (40.4%).

$^1$HNMR (300 MHz, CDCl$_3$): δ 0.20 (s, 6H), 0.51 (d, J=7.0 Hz, 3H), 0.87 (d, J=7.2 Hz, 3H), 0.84–0.94 (m, 3H), 0.99 (s, 9H), 1.36 (d, J=7.2 Hz, 3H), 1.16–1.58 (m, 20H), 2.35–2.55 (m, 2H), 3.40–3.56 (m, 1H), 6.76–7.00 (m, 2H), 7.16–7.42 (m, 2H) ppm.

IR (liquid film): 2960, 2932, 2860, 1600, 1584, 1482, 1290, 1256, 1108 cm$^{-1}$.

Mass (m/z, %): 475 (M$^+$-31, trace), 392 (19), 235 (8), 196 (18), 195 (100).

EXAMPLE 35

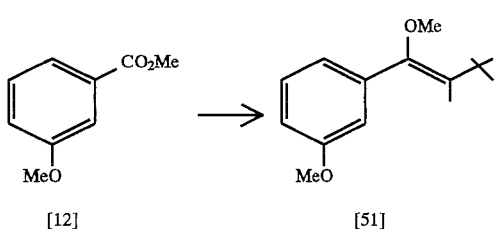

[12]   [51]

In an atmosphere of argon, 5 g (32 mmol) of titanium trichloride was suspended in 100 ml of anhydrous THF. This mixture was stirred for 15 minutes and then ice-cooled.

To this ice-cooled suspension, 608 (16 mmol) of lithium aluminum hydride was added, and this mixture was stirred for 1 hour.

To this reaction mixture, with the temperature thereof raised to room temperature, 2.3 ml (16 mmol) of triethylamine was added, and the solution was refluxed for 30 minutes.

To the thus refluxed solution, a solution of 531 mg (3.2 mmol) of methyl 3-methoxybenzoate (Compound [12]) and 0.79 ml (6.4 mmol) of pinacolin in 20 ml of anhydrous THF was added dropwise. This reaction solution was further refluxed for 60 minutes.

This reaction solution was then ice-cooled and water was added dropwise thereto. The reaction mixture was then extracted with ethyl acetate. The extracted layer was successively washed with water, a saturated aqueous solution of sodium hydrogencarbonate and a saturated aqueous solution of sodium chloride, dried over anhydrous magnesium sulfate and concentrated.

The residue was chromatographed on silica gel and eluted with a mixed solvent of hexane and dichloromethane (6:1), whereby 2-t-butyl-1-methoxy-1-(3-methoxyphenyl)-1-propene (Compound [51]) was obtained in the form of a colorless oil in a yield of 473 mg (63.2%).

$^1$HNMR (300 MHz, CDCl$_3$): δ 1.23 (s, 9H), 1.53 (s, 3H), 3.18 (s, 3H), 3.82 (s, 3H), 6.79–6.88 (m, 3H), 7.21–7.28 (m, 1H) ppm.

IR (liquid film): 2952, 1642, 1595, 1580, 1484, 1290, 1222 cm$^{-1}$.

Mass (m/z, %): 234 (M$^+$, 43), 219 (100), 187 (37), 172 (22).

EXAMPLE 36

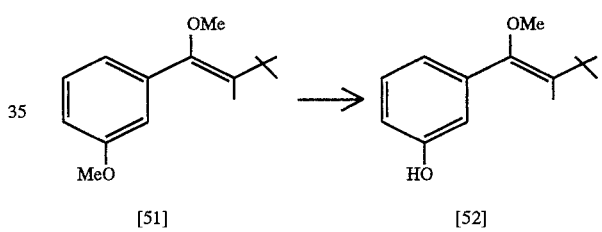

[51]   [52]

In an atmosphere of argon, 0.25 ml (3.34 mmol) of ethanethiol was added to an ice-cooled suspension of 127 mg (3.17 mmol) of sodium hydride (60% suspension) suspended in 5 ml of anhydrous DMF, and this mixture was stirred for 10 minutes.

To the above mixture, with the temperature thereof raised to room temperature, there was added dropwise a solution of 390 mg (1.67 mmol) of 2-t-butyl-1-methoxy-1-(3-methoxyphenyl)-1-propene (Compound [51]) synthesized in Example 35 in 3 ml of anhydrous DMF.

This reaction solution was refluxed for 3 hours and was then poured into a saturated aqueous solution of ammonium chloride. This mixture was then extracted with ethyl acetate. The extracted layer was washed with a saturated aqueous solution of sodium chloride, dried over anhydrous magnesium sulfate, and concentrated.

The residue was chromatographed on silica gel and eluted with a mixed solvent of hexane and ethyl acetate (10:1), whereby 2-t-butyl-1-(3-hydroxyphenyl)-1-methoxy-1-propene (Compound [52]) was obtained in a yield of 357 mg (97.2%).

$^1$HNMR (300 MHz, CDCl$_3$): δ 1.22 (s, 9H), 1.53 (s, 3H), 3.18 (s, 3H), 4.70–4.75 (m, 1H), 6.66–6.79 (m, 2H), 6.81–6.87 (m, 1H), 7.18–7.24 (m, 1H) ppm.

IR (liquid film: 3304, 2968, 1596, 1448, 1298, 1220, 1102 cm$^{-1}$.

Mass (m/z, %): 220, (M⁺, 15), 205 (33), 173 (14), 150 (45), 121 (100).

EXAMPLE 37

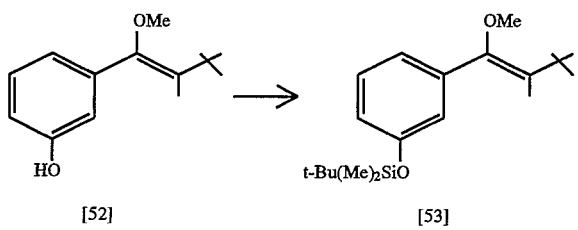

In an atmosphere of argon, 303 mg (1.38 mmol) of 2-t-butyl-1-(3-hydroxyphenyl)-1-methoxy-1-propene (Compound [52]) synthesized in Example 36 was dissolved in 5 ml of anhydrous DMF.

To this solution, 113 mg (1.66 mmol) of imidazole and 250 mg (1.66 mmol) of t-butyldimethylchlorosilane were successively added, and the mixture was stirred at room temperature for 6 hours.

This reaction solution was poured into a saturated aqueous solution of sodium chloride and extracted with ethyl acetate. The extracted layer was dried over anhydrous magnesium sulfate and concentrated.

the residue was chromatographed on silica gel and eluted with a mixed solvent of hexane and dichloromethane (10:1), whereby 2-t-butyl-1-[3-(t-butyldimethylsiloxy)-phenyl]-1-methoxy-1-propene (Compound [53]) was obtained in the form of a colorless oil in a yield of 403 mg (87.4%).

¹HNMR (300 MHz, CDCl₃): δ 0.19 (s, 6H), 0.99 (s, 9H), 1.23 (s, 9H), 1.52 (s, 3H), 3.18 (s, 3H), 6.72–6.79 (m, 1H), 6.82–6.79 (m, 1H), 6.82–6.89 (m, 1H), 7.15–7.23 (m, 1H) ppm.

IR (liquid film): 2956, 2864, 1644, 1598, 1578, 1482, 1296, 1222 cm⁻¹.

Mass (m/z, %): 334 (M⁺, 44), 319 (100), 287 (18), 220 (10), 205 (22).

EXAMPLE 38

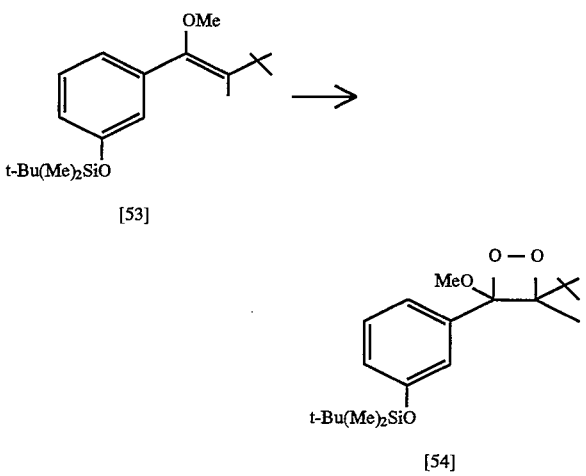

155 mg (0.46 mmol) of 2-t-butyl-1-[3-(t-butyldimethylsiloxy)phenyl]-1-methoxy-1-propene (Compound [53]) synthesized in Example 37 was dissolved in 20 ml of dichloromethane. To this solution, 5 mg of tetraphenylporphine was added.

This solution was ice-cooled and irradiated with a sodium lamp (180 W) in the atmosphere of oxygen for 3 hours.

The reaction mixture was concentrated, and the residue was chromatographed on silica gel and eluted with a mixed solvent of hexane and ether (20:1), whereby a crude product was obtained.

This crude product was then subjected to preparative TLC, developed with a mixed solvent of hexane and ether (50:1), and eluted with dichloromethane, whereby 3-t-butyl-4-[(3-t-butyldimethylsiloxy)phenyl]-4-methoxy -3-methyl-1,2-dioxetane (Compound [54]) was obtained in the form of a pale yellow oil in a yield of 30 mg (17.7%).

¹HNMR (300 MHz, CDCl₃): δ 0.19 (s, 6H), 0.98 (s, 9H), 1.10 (s, 3H), 1.20 (s, 9H), 3.01 (s, 3H), 6.86 (dd, J=9.0 and 2.4 Hz, 1H), 6.82–7.28 (m, 2H), 7.24–7.32 (m, 1H) ppm.

IR (liquid film): 2960, 2936, 1602, 1586, 1484, 1442, 1290 cm⁻¹.

Mass (m/z, %): 334 (M⁺-32, trace), 266 (28), 210 (22), 209 (100).

EXAMPLE 39

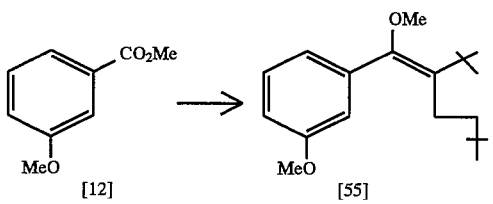

In an atmosphere of argon, 5 g (32 mmol) of titanium trichloride was suspended in 100 ml of anhydrous THF. This mixture was stirred for 25 minutes and then ice-cooled.

To this ice-cooled suspension, 608 mg (16 mmol) of lithium aluminum hydride was added, and the solution was stirred for 30 minutes.

To this reaction solution, with the temperature thereof raised to room temperature, 2.3 ml (16 mmol) of triethylamine was added, and the solution was refluxed for 30 minutes.

To the thus refluxed solution, a solution of 531 mg (3.2 mmol) of methyl 3methoxybenzoate (Compound [12]) and 1.026 g (6.04 mmol) of 2,2,6,6-tetramethylheptan-3-one in 20 ml of anhydrous THF was added dropwise. This reaction solution was further refluxed for 75 minutes.

This reaction solution was then ice-cooled and water was added dropwise thereto. The reaction mixture was then extracted with ethyl acetate. The extracted layer was successively washed with water, a saturated aqueous solution of sodium hydrogencarbonate and a saturated aqueous solution of sodium chloride, dried over anhydrous magnesium sulfate and concentrated.

The residue was chromatographed on silica gel and eluted with a mixed solvent of hexane and dichloromethane (6:1), whereby 2-t-butyl-1-methoxy-1-(3-methoxyphenyl)-5,5-dimethyl-1-hexene (Compound [55]) was obtained in the form of a colorless oil in a yield of 454 mg (46.7%).

¹HNMR (300 MHz, CDCl₃): δ 0.62 (s, 9H), 1.15 (dt, J=8.7 and 4.4 Hz, 2H), 1.25 (s, 9H), 1.81 (dt, J=8.7 and 4.4 Hz, 2), 3.17 (s, 3H), 3.81 (s, 3H), 6.78–6.86 (m, 3H), 7.24 (t, J=7.8 Hz, 1H) ppm.

IR (liquid film): 2956, 1598, 1578, 1484, 1298, 1222, 1130 cm⁻¹.

Mass (m/z, %): 304 (M⁺, 73), 289 (100), 233 (85), 219 (39), 201 (22), 177 (32).

EXAMPLE 40

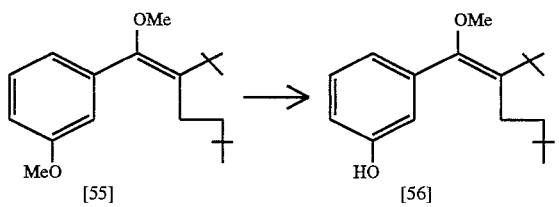

In an atmosphere of argon, 0.20 ml (2.7 mmol) of ethanethiol was added to an ice-cooled suspension of 103 mg (2.57 mmol) of sodium hydride (60% suspension) suspended in 5 ml of anhydrous DMF, and this mixture was stirred for 10 minutes.

To the above mixture, with the temperature thereof raised to room temperature, there was added dropwise a solution of 395 mg (1.30 mmol) of 2-t-butyl-1-methoxy-1-(3-methoxyphenyl) -5,5-dimethyl-1-hexene (Compound [55]) synthesized in Example 39 in 3 ml of anhydrous DMF.

This reaction solution was refluxed for 3 hours and was then poured into a saturated aqueous solution of ammonium chloride. This mixture was then extracted with ethyl acetate. The extracted layer was washed with a saturated aqueous solution of sodium chloride, dried over anhydrous magnesium sulfate, and concentrated.

The residue was chromatographed on silica gel and eluted with a mixed solvent of hexane and ethyl acetate (10:1), whereby 2-t-butyl-1-(3-hydroxyphenyl)-1-methoxy-5,5-dimethyl-1-hexene (Compound [56]) was obtained in a yield of 337 mg (89.4%).

$^1$HNMR (300 MHz, CDCl$_3$): δ 0.63 (s, 9H), 1.15 (dt, J=8.7 and 4.4 Hz, 2H), 1.24 (s, 9H), 1.82 (dt, J=8.7 and 4.4 Hz, 2H), 3.17 (s, 3H), 4.75 (s, 1H), 6.72–6.79 (m, 2H), 6.80–6.86 (m, 1H), 7.19 (t, J=7.7 Hz, 1H) ppm.

IR (liquid film): 3408, 2956, 1584, 1470, 1294, 1206, 1130 cm$^{-1}$.

Mass (m/z, %): 290 (M$^+$, 77), 275 (100), 219 (87), 205 (57), 121 (82).

EXAMPLE 41

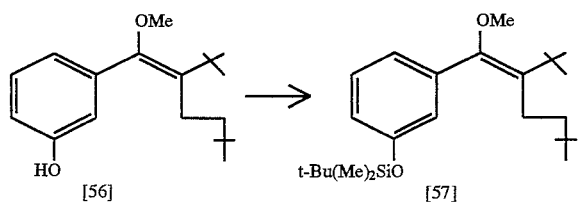

In an atmosphere of argon, 304 mg (1.05 mmol) of 2-t-butyl-1-(3-hydroxyphenyl)-1-methoxy-5,5-dimethyl-1-hexene (Compound [56]) synthesized in Example 40 was dissolved in 3 ml of anhydrous DMF.

To this solution, 89 mg (1.31 mmol) of imidazole and 180 mg (1.19 mmol) of t-butyldimethylchlorosilane were successively added, and the solution was stirred at room temperature for 2 hours.

This reaction solution was poured into a saturated aqueous solution of sodium chloride and extracted with ethyl acetate. The extracted layer was dried over anhydrous magnesium sulfate and concentrated.

The residue was chromatographed on silica gel and eluted with a mixed solvent of hexane and dichloromethane (10:1), whereby 2-t-butyl-1-[3-(t-butyldimethylsiloxy)-phenyl]-1-methoxy-5,5-dimethyl-1-hexene (Compound [57]) was obtained in the form of a colorless oil in a yield of 332 mg (78.4%).

$^1$HNMR (300 MHz, CDCl$_3$): 0.20 (s, 6H), 0.63 (s, 9H), 1.00 (s, 9H), 1.08–1.18 (m, 2H), 1.25 (s, 9H), 1.80–1.88 (m, 2H), 3.16 (s, 3H), 6.72–6.80 (m, 2H), 6.82–6.88 (m, 1H), 7.19 (s, J=7.7 Hz, 1H) ppm.

IR (liquid film): 2956, 1638, 1596, 1578, 1482, 1296, 1130 cm$^{-1}$.

Mass (m/z, %): 404 (M$^+$, 98), 389 (100), 334 (28), 333 (97), 319 (34).

EXAMPLE 42

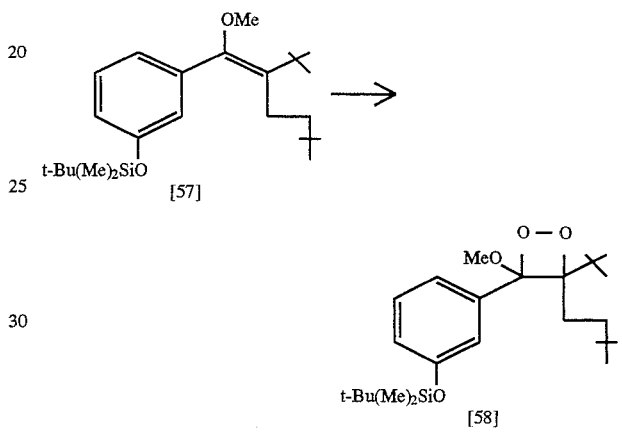

139 mg (0.35 mmol) of 2-t-butyl-1-[3-(t-butyl dimethylsiloxy)phenyl]-1-methoxy-5,5-dimethyl-1-hexene (Compound [57]) synthesized in Example 41 was dissolved in 20 ml of dichloromethane. To this solution, 6 mg of tetraphenylporphine was added.

This solution was ice-cooled and irradiated with a sodium lamp (180 W) in the atmosphere of oxygen for 2 hours.

The reaction solution was concentrated, and the residue was chromatographed on silica gel and eluted with a mixed solvent of hexane and ether (50:1), whereby a crude product was obtained.

This crude product was then subjected to preparative TLC, developed with a mixed solvent of hexane and ether (100:1), and eluted with dichloromethane, whereby 3-t-butyl-4-[3-(t-butyldimethylsiloxy)phenyl]-4-methoxy-3-(3, 3-dimethylbutyl)-1,2-dioxetane (Compound [58]) was obtained in the form of a pale yellow oil in a yield of 66 mg (44.0%).

$^1$HNMR (300 MHz, CDCl$_3$): δ 0.15–0.28 (m, 6H), 0.54 (s, 9H), 0.70–0.88 (m, 1H), 0.98 (s, 9H), 1.04–1.22 (m, 1H), 1.23 (s, 9H), 1.47 (td, J=13.7 and 4.7 Hz, 1H), 1.66–1.89 (m, 1H), 2.92–3.07 (m, 3H), 6.66–6.92 (m, 2H), 7.17–7.52 (m, 2H) ppm.

IR (liquid film): 2960, 2904, 1600, 1584, 1484, 1290, 1262 cm$^{-1}$.

Mass (m/z, %): 404 (M$^+$−32, 9), 266 (26), 209 (100).

EXAMPLE 43

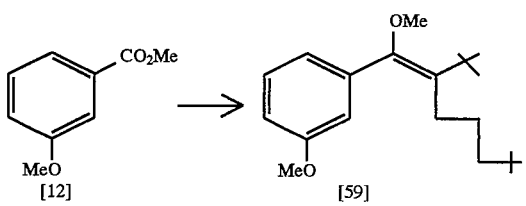

In an atmosphere of argon, 5 g (32 mmol) of titanium trichloride was suspended in 100 ml of anhydrous THF. This mixture was stirred for 25 minutes and then ice-cooled.

To this ice-cooled suspension, 608 mg (16 mmol) of lithium aluminum hydride was added, and this solution was stirred for 30 minutes.

To this reaction solution, with the temperature thereof raised to room temperature, 2.3 ml (16 mmol) of triethylamine was added, and the solution was refluxed for 30 minutes.

To the thus refluxed solution, a solution of 531 mg (3.2 mmol) of methyl 3-methoxybenzoate (Compound [12]) and 1.176 g (6.36 mmol) of 2,2,7,7-tetramethyloctan-3-one in 20 ml of anhydrous THF was added dropwise. This reaction solution was further refluxed for 60 minutes.

This reaction solution was then ice-cooled and water was added dropwise thereto. The reaction mixture was then extracted with ethyl acetate. The extracted layer was successively washed with water, a saturated aqueous solution of sodium hydrogencarbonate and a saturated aqueous solution of sodium chloride, dried over anhydrous magnesium sulfate and concentrated.

The residue was chromatographed on silica gel and eluted with a mixed solvent of hexane and dichloromethane (10:1), whereby 2-t-butyl-1-methoxy-1-(3-methoxyphenyl)-6,6-dimethyl-1-heptene (Compound [59]) was obtained in the form of a pale yellow oil in a yield of 500 mg (49.1%).

$^1$HNMR (300 MHz, CDCl$_3$): δ 0.78 (s, 9H), 0.85–0.95 (m, 2H), 1.25 (s, 9H), 1.17–1.32 (m, 2H), 1.77 (t, J=8.0 Hz, 2H), 3.17 (s, 3H), 3.81 (s, 3H), 6.78–6.87 (m, 3H), 7.24 (t, J=7.6 Hz, 1H), ppm.

IR (liquid film): 2956, 2904, 1596, 1580, 1484, 1288, 1222 cm$^{-1}$.

Mass (m/z, %): 318 (M$^+$, 56), 303 (70), 233 (100), 219 (29), 177 (32).

EXAMPLE 44

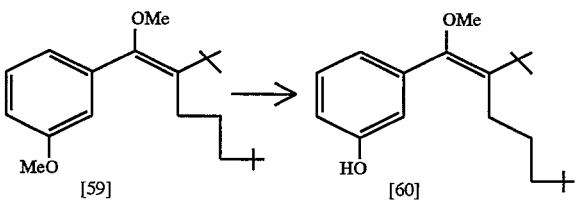

In an atmosphere of argon, 0.19 ml (2.57 mmol) of ethanethiol was added to an ice-cooled suspension of 96 mg (2.39 mmol) of sodium hydride (60% suspension) suspended in 5 ml of anhydrous DMF, and this solution was stirred for 20 minutes.

To the above solution, with the temperature thereof raised to room temperature, there was added dropwise a solution of 400 mg (1.26 mmol) of 2-t-butyl-1-methoxy-1-(3-methoxyphenyl)-6,6-dimethyl-1-heptene (Compound [59]) synthesized in Example 43 in 3ml of anhydrous DMF.

This reaction solution was refluxed for 2 hours and 40 minutes and was then poured into a saturated aqueous solution of ammonium chloride. This mixture was then extracted with ethyl acetate. The extracted layer was washed with a saturated aqueous solution of sodium chloride, dried over anhydrous magnesium sulfate, and concentrated.

The residue was chromatographed on silica gel and eluted with a mixed solvent of hexane and ethyl acetate (10:1), whereby 2-t-butyl-1-(3-hydroxyphenyl)-1-methoxy-6,6-dimethyl-1heptene (Compound [60]) was obtained in a yield of 340 mg (88.8%).

$^1$HNMR (300 MHz, CDCl$_3$): δ 0.78 (s, 9H), 0.86–0.94 (m, 2H), 1.24 (s, 9H), 1.16–1.30 (m, 2H), 1.72–1.81 (m, 2H), 3.17 (s, 3H), 4.68 (s, 1H), 6.72–6.85 m, 3H), 7.20 (t, J=7.7 Hz, 1H) ppm.

IR (liquid film): 3384, 2956, 1582, 1478, 1446, 1292, 1206 cm$^{-1}$.

Mass (m/z, %): 304 (M$^+$, 69), 289 (83), 219 (100), 205 (34), 163 (34).

EXAMPLE 45

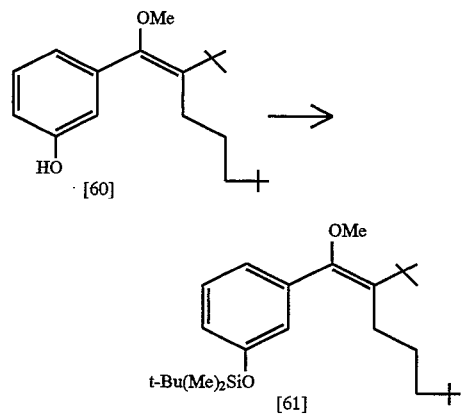

In an atmosphere of argon, 320 mg (1.05 mmol) of 2-t-butyl- 1-(3-hydroxyphenyl)-1-methoxy-6,6-dimethyl-1-heptene (Compound [60]) synthesized in Example 44 was dissolved in 3 ml of anhydrous DMF.

To this solution, 85 mg (1.26 mmol) of imidazole and 190 mg (1.26 mmol) of t-butyldimethylchlorosilane were successively added, and the solution was stirred at room temperature for 4 hours.

This reaction solution was poured into a saturated aqueous solution of sodium chloride and extracted with ethyl acetate. The extracted layer was dried over anhydrous magnesium sulfate and concentrated.

The residue was chromatographed on silica gel and eluted with a mixed solvent of hexane and dichloromethane (10:1), whereby 2-t-butyl-1-[3-(t-butyldimethylsiloxy)phenyl]-1-methoxy-6,6-dimethyl-1heptene (Compound [61]) was obtained in the form of a colorless oil in a yield of 393 mg (89.5%).

$^1$HNMR (300 MHz, CDCl$_3$): δ 0.19 (s, 6H), 0.77 (s, 9H), 0.84–0.93 (m, 2H), 0.98 (s, 9H), 1.25 (s, 9H), 1.16–1.30 (m, 2H), 1.74–1.83 (m, 2H), 3.15 (s, 3H), 6.71–6.80 (m, 2H), 6.81–6.87 (m, 1H), 7.18 (t, J=7.7 Hz, 1H) ppm.

IR (liquid film): 2956, 1596, 1578, 1480, 1292 cm$^{-1}$.

Mass (m/z, %): 418 (M$^+$, 79), 403 (69), 333 (100), 319 (17).

EXAMPLE 46

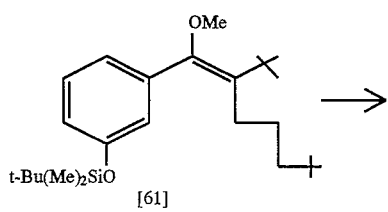

93 mg (0.22 mmol) of 2-t-butyl-1-[3-(t-butyl dimethylsiloxy)phenyl]-1-methoxy-6,6-dimethyl-1-heptene (Compound [61]) synthesized in Example 45 was dissolved in 20 ml of dichloromethane. To this solution, 5 mg of tetraphenylporphine was added.

This solution was ice-cooled and irradiated with a sodium lamp (180 W) in an atmosphere of oxygen for 2 hours and 15 minutes.

The reaction solution was concentrated, and the residue was chromatographed on silica gel and eluted with a mixed solvent of hexane and ether (50:1), whereby a crude product was obtained.

This crude product was then subjected to preparative TLC, developed with a mixed solvent of hexane and dichloromethane (10:1), and eluted with dichloromethane, whereby 3-t-butyl-4-[(3-(t-butyldimethylsiloxy)phenyl]-4-methoxy-3-(4,4-dimethylpentyl)-1,2-dioxetane (Compound [62]) was obtained in the form of a pale yellow oil in a yield of 37 mg (37.4%).

$^1$HNMR (300 MHz, CDCl$_3$): δ 0.17–0.26 (m, 6H), 0.67 (s, 9H), 0.58–0.98 (m, 2H), 0.99 (s, 9H), 1.05–1.22 (m, 1H), 1.23 (s, 9H), 1.37–1.60 (m, 1H), 1.68–1.82 (m, 2H), 3.01 (s, 3H), 6.66–6.94 (m, 2H), 7.18–7.55 (m, 2H), ppm.

IR (liquid film): 2960, 1602, 1586, 1484, 1288, 1292 cm$^{-1}$.

Mass (m/z, %): 418 (M$^+$–32, 12), 266 (46), 235 (18), 210 (41), 209 (100), 177 (37).

Reference Example 10

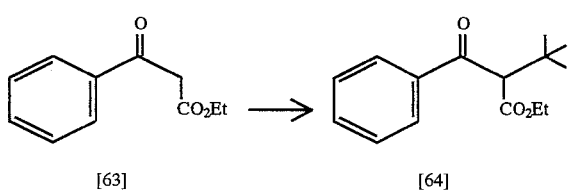

In an atmosphere of nitrogen, 4.99 g (37 mmol) of dried zinc chloride and 14.6 g (76 mmol) of ethyl benzoylacetate (Compound [63]) and 16.5 ml (152 mmol) of t-butyl chloride were added to 30 ml of anhydrous dichloromethane at room temperature, and this reaction mixture was refluxed overnight.

The reaction mixture was poured into a saturated aqueous solution of sodium chloride and then extracted with dichloromethane. The extracted layer was dried over anhydrous magnesium sulfate and concentrated.

The residue was distilled under reduced pressure, whereby ethyl 2-benzoyl-2-t-butylacetate (Compound [64]) was obtained in a yield of 8.76 g (46.5%).

Melting point: 45°–47° C., Boiling point: 89°–90° C. (0.4 mmHg)

$^1$HNMR (400 MHz, CDCl$_3$): δ 1.16 (s, 9H), 1.17 (t, J=7.2 Hz, 3H), 4.13 (q, J=7.2 Hz, 2H), 4.31 (s, 1H), 7.26–7.96 (m, 5H), ppm.

IR (KBr): 3368, 3173, 3067, 1662, 1624, 1404, 686 cm$^{-1}$.

Mass (m/z, %): 248 (M$^+$, 1), 192 (100), 146 (10), 105 (58), 77 (2).

EXAMPLE 47

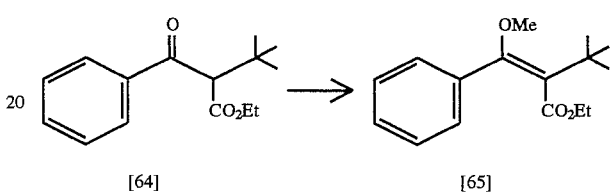

6.23 g (25 mmol) of ethyl 2-benzoyl-2-t-butylacetate (Compound [64]) synthesized in Reference Example 10 was added to 50 ml of anhydrous DMSO, and the solution was stirred at room temperature in an atmosphere of nitrogen.

To this solution, 5.61 g (50 mmol) of potassium t-butoxide was added, and the solution was stirred for 30 minutes.

This solution was then cooled to 0° C., and 4.75 ml (50 mmol) of dimethyl sulfate was added thereto. This reaction mixture was stirred at room temperature for 1 hour.

The reaction mixture was then poured into a saturated aqueous solution of sodium chloride and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of dichloromethane and hexane (1:2), whereby ethyl 2-t-butyl-3-methoxy-3-phenyl-2-propenoate (Compound [65]) was obtained in a yield of 3.46 g (52.6%).

$^1$HNMR (400 MHz, CDCl$_3$): δ 0.86 (t, J=6.8 Hz, 3H), 1.30 (s, 9H), 3.30 (s, 3H), 3.81 (q, J=6.8 Hz, 2H), 7.26–7.34 (m, 5H) ppm.

IR (liquid film): 2959, 1717, 1296, 1072 cm$^{-1}$.

Mass (m/z, %): 262 (M$^+$, 43), 247 (100), 187 (30), 105 (30), 87 (17), 77 (15).

EXAMPLE 48

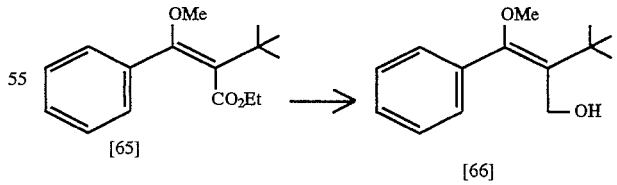

5.24 g (20 mmol) of ethyl 2-t-butyl-3-methoxy-3-phenyl-2-propenoate (Compound [65]) synthesized in Example 47 was added to 10 ml of anhydrous toluene, and the mixture was stirred in an atmosphere of nitrogen at –78° C.

To this solution, 29.2 ml (44 mmol) of diisobutylaluminum hydride (1.5M toluene solution) was added, and the mixture was stirred for 1 hour.

The reaction mixture was then poured into a saturated aqueous solution of sodium chloride and extracted with ethyl acetate. The extracted layer was washed with a saturated aqueous solution of sodium chloride, dried over anhydrous magnesium sulfate and concentrated, whereby 2-t-butyl-3-methoxy-3-phenyl-2-propen-1-ol (Compound [66]) was obtained in the form of a colorless amorphous solid in a yield of 3.99 g (90.7%).

$^1$HNMR (400 MHz, C$_6$D$_6$): δ 1.48 (s, 9H), 3.01 (s, 3H), 3.86 (d, J=4.8 Hz, 2H), 7.06–7.31 (m, 5H) ppm.

IR (KBr): 3285, 2957, 1633, 1292, 1113, 1010, 696 cm$^{-1}$.

Mass (m/z, %): 220 (M$^+$, 35), 205 (30), 187 (65), 163 (56), 105 (63), 77 (100).

EXAMPLE 49

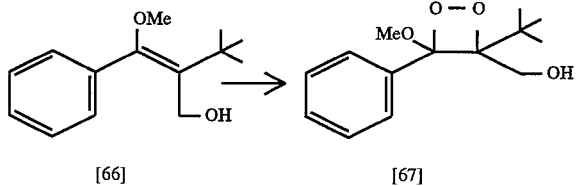

[66]                [67]

210 mg (0.95 mmol) of 2-t-butyl-3-methoxy-3-phenyl-2-propen-1-ol (Compound [65]) synthesized in Example 48 and 5 mg of TPP were dissolved in 10 ml of dichloromethane. This solution was stirred in an atmosphere of oxygen at 0° to 5° C., and irradiated with a sodium lamp (940 W) for 1 hour.

This reaction mixture was concentrated, and the residue was subjected to preparative TLC, and developed with a mixed solvent of hexane and diethyl ether (10:1), whereby 3-t-butyl-3-hydroxymethyl-4-methoxy-4-phenyl-1,2-dioxetane (Compound [67]) was obtained in the form of a yellow oil in a yield of 86 mg (35.8%).

$^1$HNMR (400 MHz, C$_6$D$_6$): δ 0.59 (t, J=7.3 Hz, 1H), 1.43 (s, 9H), 2.80 (s, 3H), 3.83 (q$_{AB}$, J=7.3 Hz, 2H), 7.00–7.48 (m, 5H) ppm.

IR (liquid film): 3584, 2966, 1450, 1249, 1107, 1041, 706 cm$^{-1}$.

Mass (m/z, %): 253 (M$^+$+1, 1), 220 (22), 205 (8), 187 (11), 163 (11), 136 (19), 117(8), 105 (67), 85 (16), 77 (44), 55 (100).

EXAMPLE 50

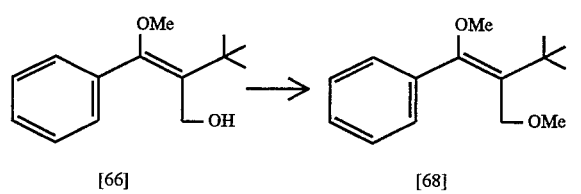

[66]                [68]

In an atmosphere of nitrogen, 0.24 g (6 mmol) of sodium hydride, 1.16 g (5 mmol) of 2-t-butyl-3-methoxy-3-phenyl-2-propen-1-ol (Compound [66]) synthesized in Example 48, and 0.38 ml (6 mmol) of methyl iodide were successively added to 10 ml of anhydrous THF at 0° C.

This reaction mixture was then refluxed for 3 hours, poured into a saturated aqueous solution of ammonium chloride, and extracted with ethyl acetate. The extracted layer was washed with a saturated aqueous solution of sodium chloride, dried over anhydrous magnesium sulfate and concentrated, whereby 2-t-butyl-1,3-dimethoxy-1-phenyl-1-propene (Compound [68]) was obtained in the form of a yellow oil in a yield of 1.15 g (93.2%).

$^1$HNMR (400 MHz, C$_6$D$_6$): δ1.07 (s, 9H), 2.98 (s, 3H), 3.05 (s, 3H), 3.65 (s, 2H), 7.07–7.39 (m, 5H) ppm.

IR (liquid film): 2955, 1086, 704 cm$^{-1}$.

Mass (m/z, %): 234 (M$^+$, 17), 219 (14), 203 (27), 187 (32), 177 (35), 163 (31), 147 (32), 121 (76), 105 (95), 77 (100), 55 (71).

EXAMPLE 51

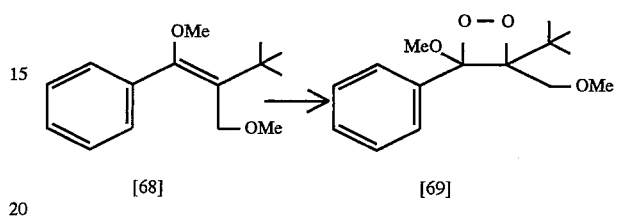

[68]                [69]

100 mg (0.43 mmol) of 2-t-butyl-1,3-dimethoxy-1-phenyl-1-propene (Compound [68]) synthesized in Example 50 and 5 mg of TPP were dissolved in 10 ml of dichloromethane. This solution was stirred in a atmosphere of oxygen at 0° to 5° C. and irradiated with a sodium lamp (940 W) for 1 hour.

This reaction mixture was concentrated, and the residue was subjected to preparative TLC and developed with a mixed solvent of hexane and diethyl ether (10:1), whereby 3-t-butyl-4-methoxy-3-methoxymethyl-4-phenyl-1,2-dioxetane (Compound [69]) was obtained in the form of a yellow oil in a yield of 77 mg (67.7%).

$^1$HNMR (400 MHz, C$_6$D$_6$): δ 1.50 (s, 9H), 2.35 (s, 3H), 2.85 (s, 3H), 3.58 (q$_{AB}$, J=6.0 Hz, 2H), 7.05–7.59 (m, 5H), ppm.

IR (liquid film): 2932, 1450, 1255, 1099, 975, 704 cm$^{-1}$.

Mass (m/z, %): 234 (M$^+$–32, 3), 187 (2), 177 (4), 136 (25), 130 (10), 105 (72), 85 (14), 77 (46), 55 (100).

Reference Example 11

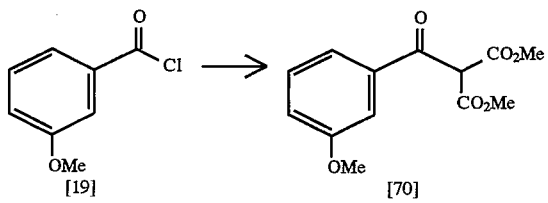

[19]                [70]

In an atmosphere of nitrogen, 7.9 g (92 mmol) of dimethoxy magnesium was added to 50 ml of diethyl ether at room temperature, with stirring. To this solution, a solution of 11.0 g (83 mmol) of dimethyl malonate in 30 ml of diethyl ether was added dropwise over a period of 20 minutes, and the mixture was stirred for 30 minutes.

This reaction solution was ice-cooled, and a solution of 14.0 g (82 mmol) of 3-anisoyl chloride (Compound [19]) in 20 ml of diethyl ether was added dropwise over a period of 20 minutes. The mixture was stirred for 30 minutes.

This reaction mixture was then refluxed for 2 hours, poured into a saturated aqueous solution of ammonium chloride and extracted with ethyl acetate. The extracted layer was washed with a saturated aqueous solution of sodium chloride, dried over anhydrous magnesium sulfate and concentrated.

Diethyl ether was added to the residue, and insoluble components were filtered out.

The filtrate was concentrated, whereby dimethyl 3-anisolylmalonate (Compound [70]) was obtained in the form of a yellow oil in a yield of 17.1 g (78.3%).

$^1$HNMR (90 MHz, CDCl$_3$): δ 3.81 (s, 6H), 3.86 (s, 3H), 7.12–7.49 (m, 4H) ppm.

IR (liquid film): 3480, 3009, 2950, 1678, 1637, 1440, 1396, 1281, 1238, 1095 cm$^{-1}$.

Mass (m/z, %): 266 (M$^+$, 18), 234 (11), 135 (100), 107 (27).

EXAMPLE 52

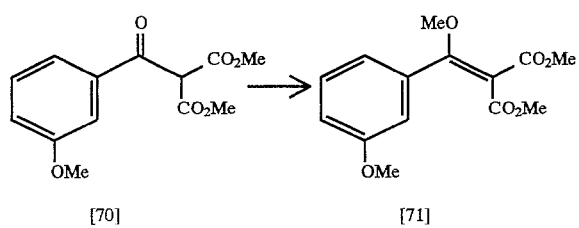

17.0 g (64 mmol) of dimethyl 3-anisolylmalonate (Compound [70]) synthesized in Reference Example 11 was added to 80 ml of DMF, and the solution was stirred and ice-cooled. To this ice-cooled solution, 13.3 g (96 mmol) of potassium carbonate was added, and the solution was stirred for 1 hour.

To this solution, 12.9 g (102 mmol) of dimethyl sulfate was added, and the mixture was refluxed for 2 hours.

This reaction mixture was poured into water and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and dichloromethane (1:4), whereby dimethyl (3-methoxyphenyl) methoxymethylidenemalonate (Compound [71]) was obtained in the form of a pale yellow oil in a yield of 8.1 g (45.3%).

$^1$HNMR (90 MHz, CDCl$_3$): δ 3.53 (s, 6H), 3.82 (s, 3H), 3.84 (s, 3H) 6.87–7.37 (m, 4 H) ppm.

IR (liquid film): 2957, 1756, 1739, 1693, 1593, 1533, 1435, 1217, 1150, 1035 cm$^{-1}$.

Mass (m/z, %): 280 (M$^+$, 62), 249 (100), 221 (86), 205 (28), 191 (33), 181 (72), 135 (37).

EXAMPLE 53

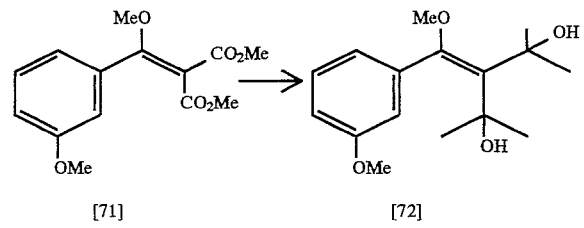

7.0 g (25 mmol) of dimethyl (3-methoxyphenyl) methoxymethylidenemalonate (Compound [71]) synthesized in Example 52 was added to 50 ml of THF. This solution was ice-cooled, and 42 ml (126 mmol) of methylmagnesium bromide (3M THF solution) was added dropwise thereto, with stirring. This reaction mixture was then stirred for 1 hour.

The reaction mixture was then refluxed for 2 hours, poured into a saturated aqueous solution of ammonium chloride and extracted with ethyl acetate. The extracted layer was successively washed with a saturated aqueous solution of sodium chloride, a saturated aqueous solution of of ammonium chloride and a saturated aqueous solution of sodium chloride, dried over anhydrous magnesium sulfate and concentrated.

The residue was washed with hexane, whereby 1,1-bis(2-hydroxypropan-2-yl)-2-methoxy-2-(3-methoxyphenyl) ethene (Compound [72]) was obtained in the form of a colorless amorphous solid in a yield of 2.6 g (37.1%).

$^1$HNMR (90 MHz, CDCl$_3$): δ 1.21 (s, 6H), 1.67 (s, 6H), 3.07 (s, 3H), 3.81 (broad s, 5H), 6.76–7.35 (m, 4H) ppm.

IR (KBr): 3230, 2979, 1595, 1485, 1321, 1234, 1182, 1094, 1072, 944, 859, 772 cm$^{-1}$.

Mass (m/z, %): 262 (M$^+$–18, 5), 247 (5), 230 (60), 215 (31), 199 (29), 187 (30), 173 (11), 159 (8), 146 (7), 135 (100), 107 (55).

EXAMPLE 54

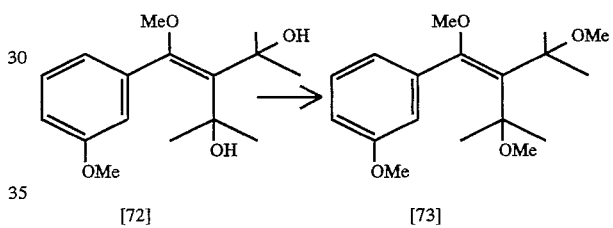

1.00 g (3.6 mmol) of 1,1-bis(2-hydroxypropan-2-yl)-2-methoxy-2-(3-methoxyphenyl)ethene (Compound [72]) synthesized in Example 53 was added to 20 ml of THF, and the solution was cooled to 0° C.

To the thus cooled solution, 0.43 g (10.8 mmol) of sodium hydride was gradually added, with stirring, in an atmosphere of nitrogen, and the mixture was stirred for 30 minutes.

To this solution, 0.9 ml (14.4 mmol) of methyl iodide was added, and the mixture was refluxed for 1 hour.

The reaction mixture was then poured into water, and extracted with ethyl acetate. The extracted layer was washed with a saturated aqueous solution of sodium chloride, dried over anhydrous magnesium sulfate and concentrated, whereby a crude 1-methoxy-1-(3-methoxyphenyl)-2,2-bis (2-methoxypropan-2-yl)ethene (Compound [73]) was obtained in the form of a pale yellow oil in a yield of 1.24 g.

$^1$HNMR (90 MHz, CDCl$_3$): δ 1.42 (s, 6H), 1.57 (s, 6H), 2.72 (s, 3H), 3.06 (s, 3H), 3.22 (s, 3H), 3.80 (s, 3H), 6.76–7.50 (m, 4H) ppm.

IR (liquid film): 2957, 1756, 1739, 1698, 1593, 1533, 1435, 1217, 1150, 1035 cm$^{-1}$.

Mass (m/z, %): 308 (M$^+$, 6), 293 (2), 277 (4), 261 (4), 245 (4), 229 (3), 189 (3), 181 (8), 173 (2), 135 (3), 107 (3), 89 (17), 73 (100).

EXAMPLE 55

[Structure: Compound [72] → Compound [74]]

1.00 g (3.6 mmol) of 1,1-bis(2-hydroxypropan-2-yl)-2-methoxy-2-(3-methoxyphenyl)ethene (Compound [72]) synthesized in Example 53 was added to 20 ml of THF, and the solution was cooled to 0° C.

To the thus cooled solution, 0.17 g (4.3 mmol) of sodium hydride was gradually added, with stirring, in an atmosphere of nitrogen, and the mixture was stirred for 30 minutes.

To this solution, 0.34 ml (5.4 mmol) of methyl iodide was added, and the mixture was stirred at room temperature for 1 hour.

The reaction mixture was then poured into water and extracted with ethyl acetate. The extracted layer was washed with a saturated aqueous solution of sodium chloride, dried over anhydrous magnesium sulfate and concentrated, whereby a crude 1-(2-hydroxypropan-2-yl)-2-methoxy-2-(3-methoxyphenyl)-1-(2-methoxypropan-2-yl)ethene (Compound [74]) was obtained in the form of a pale yellow oil in a yield of 1.10 g.

$^1$HNMR (90 MHz, CDCl$_3$): δ 1.21 (s, 6H), 1.61 (s, 6H), 3.08 (s, 3H), 3.24 (s, 3H), 3.82 (s, 3H), 5.89 (s, 1H), 6.72–7.35 (m, 4H) ppm.

IR (liquid film): 3426, 2967, 2934, 1693, 1482, 1383, 1288, 1213, 1170, 1098, 1052, 949, 762 cm$^{-1}$.

Mass (m/z, %): 294 (M$^+$, 5), 262 (15), 247 (78), 231 (27), 203 (10), 189 (31), 173 (36), 149 (13), 135 (45), 107 (22), 96 (53), 73 (100).

EXAMPLE 56

[Structure: Compound [72] → Compound [75]]

50 mg (0.18 mmol) of 1,1-bis(2-hydroxypropan-2-yl)-2-methoxy-2-(3-methoxyphenyl)ethene (Compound [72]) synthesized in Example 53 and 50 mg of methylene blue on silica gel were added to 15 ml of carbon tetrachloride, and the mixture was stirred in an atmosphere of oxygen at 0° C.

This solution was then irradiated with a sodium lamp (940 W) for 30 minutes.

The reaction mixture was concentrated and subjected to preparative TLC and developed with a mixed solvent of hexane and ethyl acetate (3:1), whereby 3,3-bis(2-hydroxypropan-2-yl)-4-methoxy-4-(3-methoxyphenyl)-1,2-dioxetane (Compound [75]) was obtained in the form of a colorless oil in a yield of 8 mg (14.4%).

$^1$HNMR (90 MHz, CDCl$_3$): δ 1.47 (s, 3H), 1.61, (s, 3H), 1.68 (s, 3H), 1.70 (s, 3H), 3.46 (s, 3H), 3.82 (s, 3H), 6.84–7.65 (m, 4H) ppm.

EXAMPLE 57

[Structure: Compound [73] → Compound [76]]

100 mg (0.32 mmol) of 1-methoxy-1-(3-methoxyphenyl)-2,2-bis(2-methoxypropan-2-yl)ethene (Compound [73]) synthesized in Example 54 and 100 mg of methylene blue on silica gel were added to 15 ml of carbon tetrachloride, and the mixture was stirred in an atmosphere of oxygen at 0° C.

This solution was irradiated with a sodium lamp (940 W) for 1 hour and 30 minutes.

The reaction mixture was concentrated. The residue was subjected to preparative TLC, and developed with a mixed solvent of hexane and dichloromethane (1:4), whereby 3-methoxy-3-(3-methoxyphenyl)-4,4-bis(2-methoxypropan-2-yl)-1,2-dioxetane (Compound [76]) was obtained in the form of a yellow oil in a yield of 40 mg (36.2%).

$^1$HNMR (40 MHz, CDCl$_3$): δ 1.28 (s, 3H), 1.31 (broad s, 3H), 1.50 (s, 3H), 1.56 (s, 3H), 2.06 (s, 3H), 3.27 (s, 3H), 3.86 (m, 3H), 6.99–7.55 (m, 4H) ppm.

IR (liquid film): 2979, 2937, 1729, 1664, 1595, 1484, 1278, 1256, 1072, 1041, 782 cm$^{-1}$.

Mass (m/z, %): 308 (M$^+$–32, 4), 280 (14), 262 (5), 247 (9), 235 (22), 208 (54), 175 (100), 135 (31), 73 (100).

Reference Example 12

[Structure: Compound [12] → Compound [77]]

In an atmosphere of argon, 13.0 ml (92.8 mmol) of diisopropylamine was added to 75 ml of anhydrous THF, and the solution was stirred at room temperature.

To this solution, 55.0 ml (89.1 mmol) of butyl lithium (1.62M hexane solution) was added, and the mixture was stirred for 30 minutes.

This solution was then cooled to −78° C., and 15.0 ml (89.5 mmol) of ethyl t-butylacetate was added, and the mixture was stirred for 20 minutes. To this mixture, 10.05 g (60.5 mmol) of methyl 3-methoxybenzoate (Compound [12]) was added, and the solution was stirred at −78° C. for 2 hours and 40 minutes, and then at 0° C. for 1 hour and 30 minutes.

This reaction mixture was poured into 1N hydrochloric acid and extracted with ethyl acetate. The extracted layer was washed with a saturated aqueous solution of sodium chloride, dried over anhydrous magnesium sulfate and concentrated.

The residue was chromatographed on silica gel and eluted with dichloromethane, whereby ethyl 2-t-butyl-2-(3- methoxybenzoyl)acetate (Compound [77]) was obtained in the form of a colorless oil in a yield of 12.24 g (72.7%).

$^1$HNMR (300 MHz, CDCl$_3$): δ 1.15 (s, 9H), 1.18 (t, J=7.2 Hz, 3H), 3.86 (s, 3H), 4.13 (q, J=7.2 Hz, 2H), 4.28 (s, 1H), 7.11 (d with fine coupling, J=8.3 Hz, 1H), 7.37 (dd, J=8.3 and 7.6 Hz, 1H), 7.48 (s with fine coupling, 1H), 7.54 (d, J=7.6 Hz, 1H) ppm.

IR (liquid film): 2964, 2912, 1736, 1696, 1598, 1582 cm$^{-1}$.

Mass (m/z, %): 278 (M$^+$, 10), 222 (26), 176 (18), 135 (100).

EXAMPLE 58

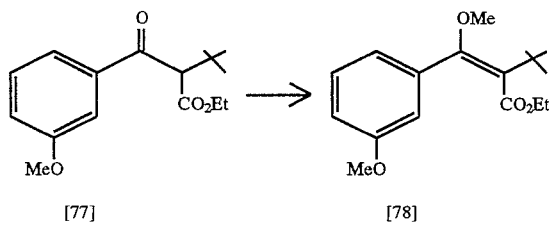

1.30 (4.68 mmol) of ethyl 2-t-butyl-2-(3-methoxybenzoyl)acetate (Compound [77])synthesized in Reference Example 12 was added to 10 ml of anhydrous DMSO, and the solution was stirred at room temperature in an atmosphere of nitrogen.

To this solution, 1.02 g (9.09 mmol) of potassium t-butoxide was added, and the mixture was stirred for 15 minutes. This solution was then cooled to 0° C., and 0.80 ml (8.44 mmol) of dimethyl sulfate was added dropwise thereto. The mixture was stirred for 50 minutes.

This reaction mixture was poured into water and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (15:2), whereby ethyl 2-t-butyl-3-methoxy-3-(3-methoxyphenyl)-2-propenoate (Compound [78]) was obtained in the form of a colorless oil in a yield of 1.15 g (84.2%).

$^1$HNMR (300 MHz, CDCl$_3$): δ 0.91 (t, J=7.1 Hz, 3H), 1.29 (s, 9H), 3.33 (s, 3H), 3.80 (s, 3H), 3.86 (q, J=7.1 Hz, 2H), 6.81–6.96 (m, 3H), 7.22 (t, J=7.8 Hz, 1H) ppm.

IR (liquid film): 2960, 1720, 1634, 1598, 1580 cm$^{-1}$.

Mass (m/z, %): 292 (M$^+$, 60), 278 (31), 277 (100), 247 (21), 231 (21), 135 (35).

EXAMPLE 59

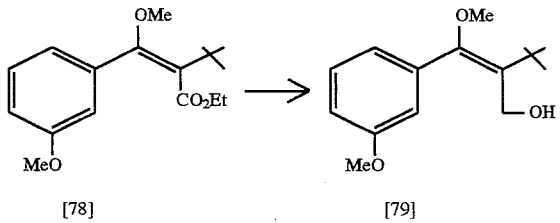

2.49 g (8.53 mmol) of ethyl 2-t-butyl-3-methoxy-3-(3-methoxyphenyl)-2-propenoate (Compound [78]) synthesized in Example 58 was added to 30 ml of anhydrous toluene, and the mixture was stirred in an atmosphere of argon at −78° C.

To this solution, 10.0 ml (17.6 mmol) of diisobutylaluminum hydride (25% toluene solution) was added, and the mixture was stirred for 1 hour and 20 minutes.

To this reaction mixture, methanol was added until no bubbles were formed therein any more, and the mixture was poured into a mixed solution of water and ethyl acetate.

This mixture was filtered through Celite and the organic layer was separated. The thus separated organic layer was washed with a saturated aqueous solution of sodium chloride, dried over anhydrous magnesium sulfate and concentrated, whereby 2-t-butyl-3-methoxy-3-(3-methoxyphenyl)-2-propen-1-ol (Compound [79]) was obtained in the form of a colorless oil in a yield of 2.08 g (97.6 %).

$^1$HNMR (300 MHz, CDCl$_3$): δ 1.32 (s, 9H), 3.24 (s, 3H), 3.82 (s, 3H), 3.94 (d, J=5.5 Hz, 2H), 6.84–6.95 (m, 3H), 7.24–7.32 (m, 1H) ppm.

IR (liquid film): 3464, 2956, 1636, 1598, 1580 cm$^{-1}$.

Mass (m/z, %): 250 (M$^+$, 67), 235 (89), 219 (35), 217 (73), 193 (100), 187 (21), 135 (28), 133 (27).

EXAMPLE 60

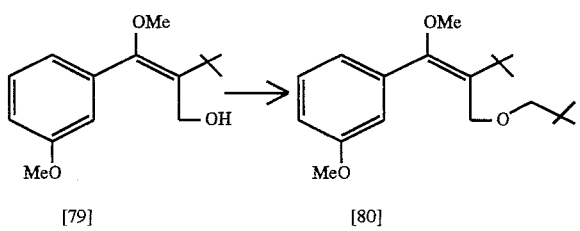

2.50 g (10.0 mmol) of 2-t-butyl-3-methoxy-3-(3-methoxyphenyl)-2-propen-1-ol (Compound [79]) synthesized in Example 59 was added to 15 ml of anhydrous DMF, and the solution was stirred in an atmosphere of argon at room temperature.

To this solution, 420 mg (10.5 mmol) of sodium hydride (60%) was added, and the mixture was stirred at 110° C. for 10 minutes. To this solution, 1.50 ml (11.9 mmol) of neopentyl bromide was added, and the mixture was stirred at 110° C. for 2 hours.

The reaction mixture was then poured into water and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (10:1), whereby 2-t-butyl-1-methoxy-1-(3-methoxyphenyl)-3-neopentyloxy-1-propene (Compound [80]) was obtained in the form of a colorless oil in a yield of 2.18 g (68.1%).

$^1$HNMR (300 MHz, CDCl$_3$): δ 0.91 (s, 9H), 1.27 (s, 9H), 2.83 (s, 2H), 3.25 (s, 3H), 3.61 (s, 2H), 3.81 (s, 3H), 6.86 (ddd, J=8.2, 2.6 and 1.0 Hz, 1H), 6.92 (s with fine coupling, 1H), 7.00 (d with fine coupling, J=7.5 Hz, 1H), 7.23 (dd, J=8.2 and 7.5 Hz, 1H) ppm.

IR (liquid film): 2956, 2868, 1636, 1598, 1580 cm$^{-1}$.

Mass (m/z, %): 320 (M$^+$, 31), 263 (73), 249 (19), 234 (19), 233 (43), 219 (42), 217 (41), 203 (21), 193 (100), 187 (21), 177 (29), 121 (29), 111 (25), 97 (33), 83 (28), 71 (37), 57 (55).

EXAMPLE 61

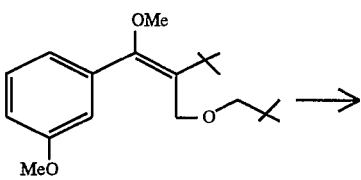

[80]

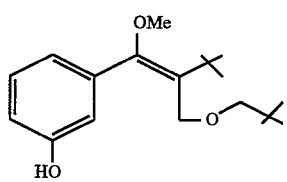

[81]

In an atmosphere of argon, 1.0 ml (13.5 mmol) of ethanethiol was added to a suspension of 530 mg (13.3 mmol) of sodium hydride (60%) suspended in 20 ml of anhydrous DMF at 0° C.

This solution was stirred at room temperature for 30 minutes, and a solution of 2.16 g (6.75 mmol) of 2-t-butyl-1-methoxy-1-(3-methoxyphenyl)-3-neopentyloxy-1-propene (Compound [80]) synthesized in Example 60 in 15 ml of anhydrous DMF was added. The mixture was refluxed for 3 hours.

This reaction mixture was then poured into a saturated aqueous solution of ammonium chloride and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (5:1), whereby 2-t-butyl-1-(3-hydroxyphenyl)-1-methoxy-3-neopentyloxy-1-propene (Compound [81]) was obtained in the form of a colorless oil in a yield of 1.23 g (59.5%).

$^1$HNMR (300 MHz, CDCl$_3$): δ 0.92 (s, 9H), 1.26 (s, 9H), 2.83 (s, 2H), 3.25 (s, 3H), 3.58 (s, 2H), 6.80 (ddd, J=8.1, 2.6 and 1.0 Hz, 1H), 6.90 (dd, J=2.6 and 1.5 Hz, 1H), 6.98 (d with fine coupling, J=7.6 Hz, 1H), 7.20 (dd, J=8.1 and 7.6 Hz, 1H) ppm.

IR (liquid film): 3400, 2960, 2908, 2872, 1652, 1596, 1482 cm$^{-1}$.

Mass (m/z, %): 306 (M$^+$, 25), 249 (56), 219 (60), 205 (39), 204 (62), 203 (34), 189 (36), 179 (47), 161 (29), 153 (29), 121 (100).

EXAMPLE 62

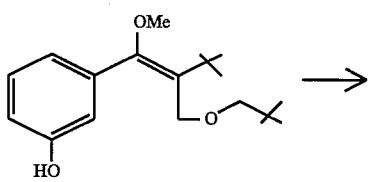

[81]

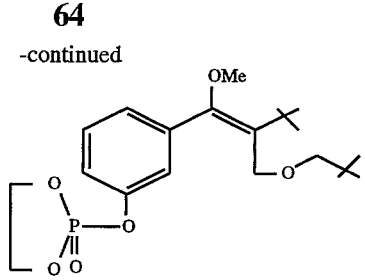

[82]

411 mg (1.34 mmol) of 2-t-butyl-1-(3-hydroxyphenyl-1-methoxy-3neopentyloxy-1propene (Compound [81]) synthesized in Example 61 was added to 5 ml of anhydrous toluene, and the solution was stirred in an atmosphere of argon at 0° C.

To this solution, 0.22 ml (1.58 mmol) of triethylamine and 0.125 ml (1.35 mmol) of 2-chloro-1,3,2,-dioxaphosphoran-2-oxide were successively added, and the mixture was stirred at 0° C. for 30 minutes and at room temperature for 2 hours.

This reaction mixture was concentrated and ether was added thereto. Insoluble components were filtered out from the mixture and the filtrate was concentrated, whereby a crude 3-(2-t-butyl-1-methoxy-3-neopentyloxy-1-propen-1-yl)phenylethylenephosphate (Compound [82]) was obtained in the form of a colorless oil in a yield of 570 mg.

$^1$HNMR (300 MHz, CDCl$_3$): δ 0.93 (s, 9H), 1.26 (s, 9H, 2.84 (s, 2H), 3.25 (s, 3H), 3.56 (s, 2H), 4.27–4.41 (m, 2H), 4.43–4.57 (m, 2H), 7.15–7.35 (m, 4H), ppm.

EXAMPLE 63

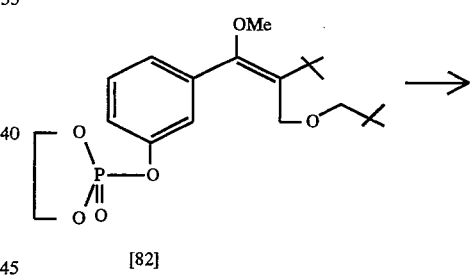

[82]

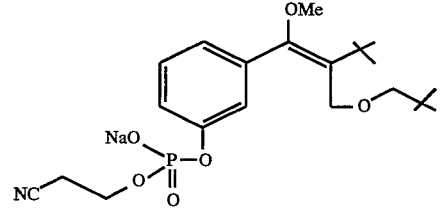

[83]

570 mg (1.38 mmol) of the crude 3-(2-t-butyl-1-methoxy-3-neopentyloxy-1-propen-1-yl)phenylethylene phosphate (Compound [82]) synthesized in Example 62 was added to 5 ml of anhydrous DMF, and the solution was stirred in an atmosphere of argon at room temperature.

To this solution, 69 mg (1.34 mmol) of sodium cyanide (95%) was added, and the mixture was stirred overnight.

This reaction mixture was concentrated. The residue was then dissolved in hexane and extracted with water. The extracted layer was subjected to freeze-drying, whereby a crude sodium 3-(2-t-butyl-1-methoxy-3-neopentyloxy-1-propen-1-yl)phenyl-2'-cyanoethylphosphate (Compound [83]) was obtained in the form of an amorphous solid in a yield of 589 mg.

¹HNMR (300 MHz, CD₃OD): δ 0.95 (s, 9H), 1.31 (s, 9H), 2.81 (t, J=6.3 Hz, 2H), 2.86 (s, 2H), 3.29 (s, 3H), 3.68 (s, 2H), 4.15 (dt, J=7.7 and 6.3 Hz, 2H), 7.10–7.35 (m, 4H), ppm.

IR (KBr): 2958, 2868, 2260, 1601, 1579, 1482, 1262, 1104 cm⁻¹.

Mass (FAB-pos, m/z, %): 485 ([M+H+Na]⁺, 26), 484 ([M+Na]⁺, 100), 382 (24), 125 (55).

EXAMPLE 64

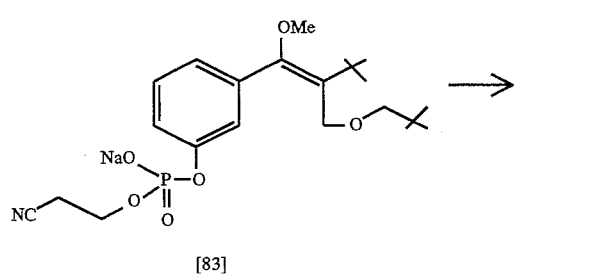

[83]

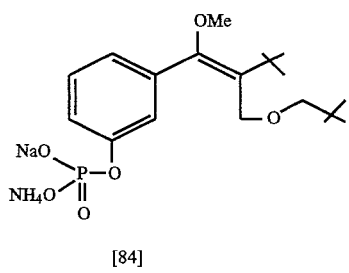

[84]

485 mg (1.05 mmol) of the crude sodium 3-(2-t-butyl-1-methoxy-3-neopentyloxy-1-propen-1-yl)phenyl-2'-cyanoethylphosphate (Compound [83]) synthesized in Example 63 was added to 2 ml of THF, and the solution was stirred in an atmosphere of argon at room temperature.

To this solution, 3.0 ml of 28% ammonia water and 1.0 ml of water were added, and the mixture was stirred for 3 days.

This reaction mixture was concentrated. The residue was dissolved in hexane and extracted with water. The extracted layer was subjected to freeze-drying, whereby a crude ammonium sodium 3-(2-t-butyl-1-methoxy-3-neopentyloxy-1-propen-1-yl)phenylphosphate (Compound [84]) was obtained in the form of an amorphous solid in a yield of 460 mg.

¹HNMR (300 MHz, CD₃OD): δ 0.94 (s, 9H), 1.31 (s, 9H), 2.85 (s, 2H), 3.29 (s, 3H), 3.69 (s, 2H), 7.08 (d, J=7.4 Hz, 1H), 7.20 (s, 1H), 7.25 (dd, J=8.0 and 7.4 Hz, 1H), 7.35 (broad d, J=8.0 Hz, 1H) ppm.

IR (KBr): 2958, 2866, 1598, 1579, 1481, 1217, 1084 cm⁻¹.

Mass (FAB-pos, m/z, %): 431 ([M+H–NH₄+Na]⁺, 48), 343 (30), 329 (35), 125 (100).

EXAMPLE 65

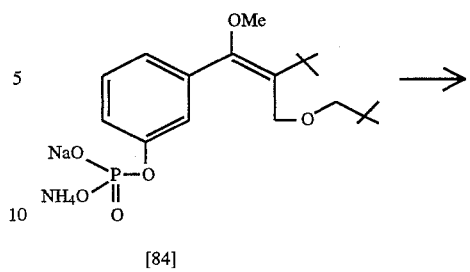

[84]

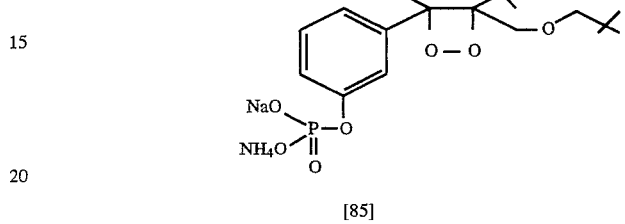

[85]

69 mg (0.162 mmol) of ammonium sodium 3-(2-t-butyl-1-methoxy-3-neopentyloxy-1-propen-1-yl)phenylphosphate (Compound [84]) synthesized in Example 64 and 2 mg of TPP were dissolved in 15 mmol of dichloromethane, and this solution was stirred in an atmosphere of oxygen at 0° C.

This solution was then irradiated with a sodium lamp (10 W) for 2 hours.

The reaction mixture was concentrated, and the residue was chromatographed on silica gel and successively eluted with dichloromethane and a mixed solvent of dichloromethane and methanol (4:1 to 2:1), whereby 3-t-butyl-4-methoxy-3-neopentyloxymethyl-4-(3'-phosphoryloxy)phenyl-1,2-dioxetane ammonium sodium salt (Compound [85]) was obtained in the form of an amorphous solid in a yield of 23 mg.

¹HNMR (300 MHz, CD₃OD): δ 0.73 (s, 9H), 1.33 (s, 9H), 2.25 (d, J=8.2 Hz, 1H), 2.64 (d, J=8.2 Hz, 1H), 3.07 (s, 3H), 3.47 (d, J=10.2 Hz, 1H), 3.84 (d, J=10.2 Hz, 1H), 7.13–7.55 (m, 4H), ppm.

EXAMPLE 66

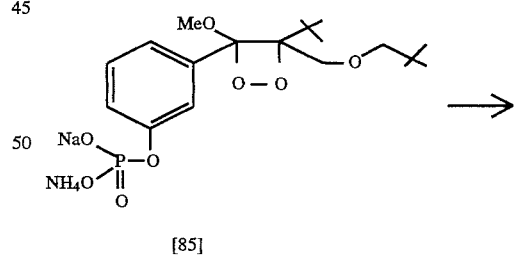

[85]

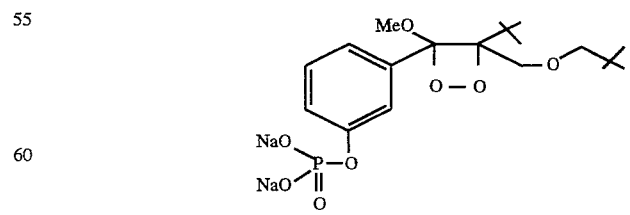

[86]

13 mg (0.028 mmol) of 3-t-butyl-4-methoxy-3-neopentyloxymethyl-4-(3'-phosphoryloxy)phenyl-1,2- dioxetane ammonium sodium salt (Compound [85]) synthesized in Example 65 was dissolved in 2.8 ml (0.028 mmol) of 0.01N aqueous solution of sodium hydrogencarbonate, and this solution was subjected to freeze-drying, whereby 3-t-butyl-4-methoxy-3-neopentyloxymethyl-4-(3'-phosphoryloxy)phenyl-1,2-dioxetane disodium salt (Compound [86]) was obtained in the form of an amorphous solid in a yield of 13 mg.

$^1$HNMR (300 MHz, CD$_3$OD): δ 0.74 (s, 9H), 1.33 (s, 9H), 2.28 (d, J=8.2 Hz, 1H), 2.63 (d, J=8.2 Hz, 1H), 3.06 (s, 3H), 3.44 (d, J=10.2 Hz, 1H), 3.84 (d, J=10.2 Hz, 1H), 7.00–7.60 (m, 4H), ppm.

IR (KBr): 2960, 2872, 1590, 1484, 1296, 1272, 1108, 992 cm$^{-1}$.

Mass (FAB-pos, m/z, %): 485 ([M+Na]$^+$, 21), 463 ([M+H]$^+$, 38), 401 (26), 379 (14), 299 (52), 277 (73), 125 (43), 115 (100).

EXAMPLE 67

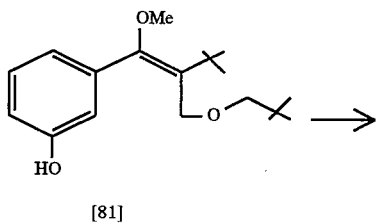

[81]

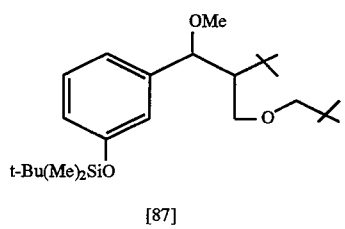

[87]

168 mg (0.549 mmol) of 2-t-butyl-1-(3-hydroxyphenyl)-1-methoxy-3-neopentyloxy-1-propene (Compound [81]) synthesized in Example 61 was dissolved in 2 ml of DMF, and the solution was stirred in an atmosphere of argon at room temperature.

To this solution, 66 mg (0.969 mmol) of imidazole and 100 mg (0.663 mmol) of t-butyldimethylchlorosilane were added, and the mixture was stirred for 2 hours.

This reaction mixture was poured into water and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (20:1), whereby 2-t-butyl-1-[3-(t-butyldimethylsiloxy)phenyl]-1-methoxy-3-neopentyloxy-1-propene (Compound [87]) was obtained in the form of a colorless oil in a yield of 158 mg (68.5%).

$^1$HNMR (90 MHz, CDCl$_3$): δ 0.19 (s, 6H), 0.90 (s, 9H), 0.98 (s, 9H), 1.26 (s, 9H), 2.81 (s, 2H), 2.33 (s, 3H), 3.62 (s, 2H), 6.73–6.87 (m, 2H), 6.97–7.03 (m, 1H), 7.14–7.19 (m, 1H) ppm.

EXAMPLE 68

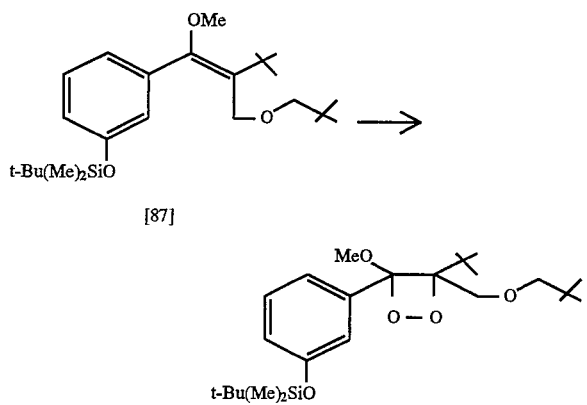

[87]

[88]

50 mg (0.119 mmol) of 2-t-butyl-1-[3-(t-butyldimethylsiloxy)phenyl]-1-methoxy-3-neopentyloxy-1-propene (Compound [87]) synthesized in Example 67 and 5 mg of TPP were dissolved in 10 ml of dichloromethane.

This solution was stirred in an atmosphere of oxygen at –78° C., and was then irradiated with a sodium lamp (940 W) for 2 hours.

The reaction mixture was concentrated, and the residue was chromatographed on silica gel and eluted with a mixed solvent of hexane and ethyl acetate (20:1), whereby 3-t-butyl-4-[3-(t-butyldimethylsiloxy)phenyl]-4-methoxy-3-neopentyloxymethyl-1,2-dioxetane (Compound [88]) was obtained in the form of a colorless oil in a yield of 35 mg (65%).

$^1$HNMR (90 MHz, CDCl$_3$): δ 0.20 (s, 6H), 0.68 (s, 9H), 0.99 (s, 9H), 1.29 (s, 9H), 2.38 ($q_{AB}$, J=8.4 Hz, 2H), 3.04 (s, 3H), 3.63 ($q_{AB}$, J=10.0 Hz, 2H), 6.78–6.89 (m, 1H), 7.00–7.24 (m, 3H) ppm.

IR (liquid film): 2960, 1600, 1480, 1280, 1100, 920, 840 cm$^{-1}$.

EXAMPLE 69

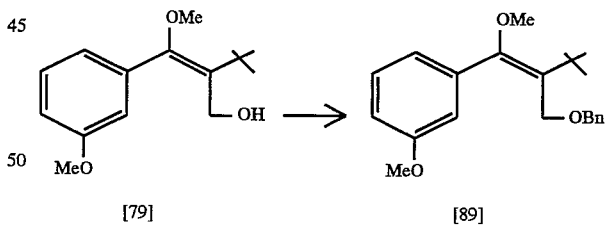

[79]                    [89]

1.164 g (4.66 mmol) of 2-t-butyl-3-methoxy-3-(3-methoxyphenyl)- 2-propen-1-ol (Compound [79]) synthesized in Example 59 was added to 12 ml of anhydrous DMF, and this solution was stirred in an atmosphere of argon at room temperature.

To this solution, 340 mg (8.50 mmol) of sodium hydride (60%) and 0.83 ml (6.98 mmol) of benzyl bromide were added, and the mixture was stirred at room temperature for 1 hour and 30 minutes.

This reaction mixture was poured into water and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (20:1), whereby 3-benzyloxy-2-t-butyl-1-methoxy-1(3-methoxyphenyl)-1-propene (Compound [89]) was obtained in the form of a colorless oil in a yield of 1.099 g (69.4%).

$^1$HNMR (300 MHz, CDCl$_3$): δ 1.30 (s, 9H), 3.25 (s, 3H), 3.76 (s, 2H), 3.78 (s, 3H), 4.31 (s, 2H), 6.87 (ddd, J=8.2 2.6 and 1.1 Hz, 1H), 6.93–7.00 (m, 2H), 7.19–7.39 (m, 6H) ppm.

IR (liquid film): 2956, 1634, 1596, 1580 cm$^{-1}$.

Mass (m/z, %): 340 (M$^+$, 36), 283 (30), 234 (75), 233 (29), 219 (32), 217 (46), 203 (23), 193 (100), 187 (24), 177 (67), 91 (88).

EXAMPLE 70

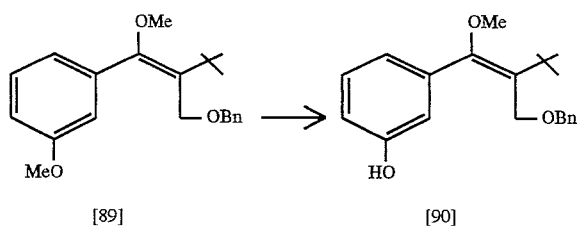

[89] → [90]

487 mg (1.43 mmol) of 3-benzyloxy-2-t-butyl-1-methoxy-1-(3-methoxyphenyl)-1-propene (Compound [89]) synthesized in Example 69 and 150 mg (3.75 mmol) of sodium hydride (60%) were added to 6 ml of DMF.

This reaction mixture was stirred in an atmosphere of argon at 0° C.

To this solution, 0.23 ml (3.11 mmol) of ethanethiol was added, and the solution was stirred for 10 minutes and then heated, with stirring, to 120° C. for 2 hours.

This reaction solution was poured into a saturated aqueous solution of sodium chloride and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (5:1), whereby 3-benzyloxy-2-t-butyl-1-(3-hydroxyphenyl)-1-methoxy-1-propene (Compound [90]) was obtained in a yield of 218 mg (46.7%).

Melting point: 93.0°–94.0° C. (colorless particle-shaped crystals, recrystallized from hexane)

$^1$HNMR (300 MHz, CDCl$_3$): δ 1.29 (s, 9H), 3.24 (s, 3H), 3.76 (s, 2H), 4.32 (s, 2H), 4.72 (s, 1H), 6.79 (ddd, J=8.1, 2.5 and 0.7 Hz, 1H), 6.85 (broad s, 1H), 6.94 (d with fine coupling, J=7.7 Hz, 1H), 7.19 (dd, J=8.1 and 7.7 Hz, 1H), 7.20–7.35 (m, 5H). ppm.

IR (KBr): 3272, 2956, 2908, 1638, 1594 cm$^{-1}$.

Mass (m/z, %): 326 (M$^+$, 36), 269 (32), 220 (76), 219 (27), 205 (33), 203 (60), 179 (82), 163 (68), 161 (36), 91 (100).

EXAMPLE 71

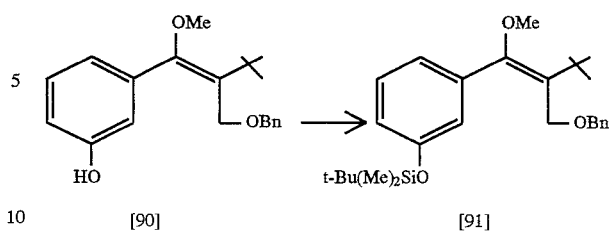

[90] → [91]

127 mg (0.390 mmol) of 3-benzyloxy-2-t-butyl-1-(3-hydroxyphenyl)-1-methoxy-1-propene (Compound [90]) synthesized in Example 70 was dissolved in 2 ml of anhydrous DMF, and the solution was stirred in an atmosphere of argon at room temperature.

To this solution, 55 mg (0.808 mmol) of imidazole and 85 mg (0.564 mmol) of t-butyldimethylchlorosilane were added, and the mixture was stirred overnight.

This reaction solution was then poured into water and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (100:1), whereby 3-benzyloxy-2-t-butyl-1-[3-(t-butyldimethylsiloxy)phenyl]-1-methoxy-1-propene (Compound [91]) was obtained in the form of a colorless oil in a yield of 144 mg (84.0%).

$^1$HNMR (300 MHz, CDCl$_3$): δ 0.17 (s, 6H), 0.97 (s, 9H), 1.29 (s, 9H), 3.23 (s, 3H), 3.77 (s, 2H), 4.29 (s, 2H), 6.80 (ddd, J=8.0, 2.5 and 1.0 Hz, 1H), 6.85 (s with fine coupling, 1H), 6.97 (d with fine coupling, J=7.6 Hz, 1H), 7.18 (dd, J=8.0 and 7.6 Hz, 1H), 7.17–7.35 (m, 5H). ppm.

IR (liquid film): 2956, 2936, 1634, 1598, 1580, 1262 cm$^{-1}$.

Mass (m/z, %): 440 (M$^+$, 22), 383 (19), 335 (28), 334 (100), 333 (29), 293 (52), 277 (42), 235 (13), 91 (65).

EXAMPLE 72

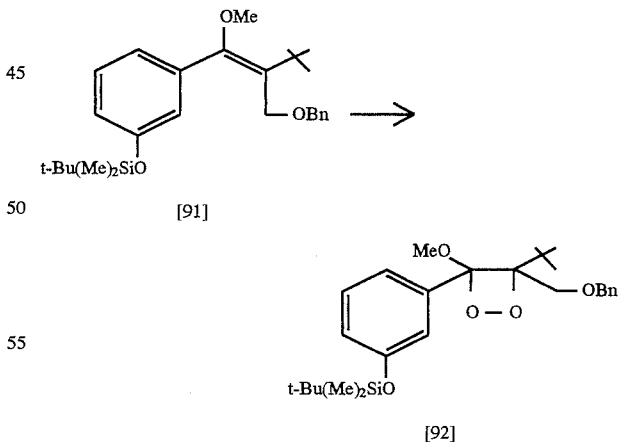

[91] → [92]

49 mg (0.111 mmol) of 3-benzyloxy-2-t-butyl-1-[3-(t-butyldimethylsiloxy)phenyl]-1-methoxy-1-propene (Compound [91]) synthesized in Example 71 and 4 mg of TPP were added to 20 ml of dichloromethane, and this solution was stirred in an atmosphere of oxygen at 0° C.

This solution was then irradiated with a sodium lamp (180 W) for 4 hours.

The reaction mixture was concentrated, and the residue was chromatographed on silica gel and eluted with a mixed solvent of hexane and ethyl acetate (200:1), whereby 3-benzyloxymethyl-3-t-butyl-4-[3-(t-butyldimethylsiloxy)phenyl]-4-methoxy-1,2-dioxetane (Compound [92]) was obtained in the form of a colorless oil in a yield of 42 mg (79.9%).

$^1$HNMR (300 MHz, CDCl$_3$): δ 0.17 (broad s, 6H), 0.98 (s, 9H), 1.29 (s, 9H), 3.05 (s, 3H), 3.57 (d, J=10.2 Hz, 1H), 3.71 (d, J=11.5 Hz, 1H), 3.84 (d, J=10.2 Hz, 1H), 3.84 (d, J=11.5 Hz, 1H), 6.83–6.90 (m, 1H), 6.94–7.30 (m, 8H), ppm.

IR (liquid film): 2960, 2936, 1602, 1586, 1256, 1096 cm$^{-1}$.

Mass (m/z, %): 472 (M$^+$, trace), 440 (2), 266 (26), 210 (22), 209 (100), 177 (20), 149 (11), 91 (41).

EXAMPLE 73

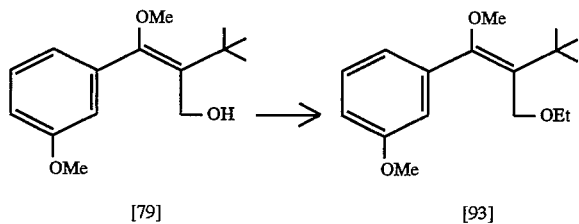

[79]   [93]

960 mg (3.84 mmol) of 2-t-butyl-3-methoxy-3(3-methoxyphenyl)-2-propen-1-ol (Compound [79]) synthesized in Example 59 was dissolved in 10 ml of anhydrous DMF, and the solution was stirred in an atmosphere of argon at room temperature.

To this solution, 330 mg (8.25 mmol) of sodium hydride (60%) and 0.6 ml (7.50 mmol) of ethyl iodide were successively added, and the mixture was stirred at room temperature for 5 hours and 30 minutes.

This solution mixture was poured into water and extracted with ethyl acetate. The extracted layer was washed with a saturated aqueous solution of sodium chloride, dried over anhydrous magnesium sulfate and concentrated.

The residue was chromatographed on silica gel and eluted with a mixed solvent of hexane and ethyl acetate (20:1), whereby 2-t-butyl-3-ethoxy-1-methoxy-1-(3-methoxyphenyl)-1-propene (Compound [93]) was obtained in the form of a colorless oil in a yield of 1.00 g (93.7%).

$^1$HNMR (300 MHz, CDCl$_3$): δ 1.13 (t, J=7.0 Hz, 3H), 1.29 (s, 9H), 3.25 (s, 3H), 3.29 (q, J=7.0 Hz, 2H), 3.69 (s, 2H), 3.82 (s, 3H), 6.84–6.90 (m, 1H), 6.94–6.99 (m, 2H), 7.22–7.29 (m, 1H), ppm.

IR (liquid film): 2956, 2868, 1636, 1598, 1580 cm$^{-1}$.

Mass (m/z, %): 278 (M$^+$, 31), 263 (8), 233 (22), 221 (100), 217 (42).

EXAMPLE 74

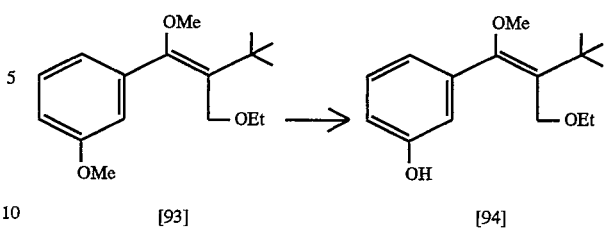

[93]   [94]

1.00 g (3.60 mmol) of 2-t-butyl-3-ethoxy-1-methoxy-1-(3-methoxyphenyl)-1propene (Compound [93]) synthesized in Example 73 and 305 mg (7.63 mmol) of sodium hydride (60%) were added to 10 ml of anhydrous DMF.

This reaction mixture was stirred in an atmosphere of argon at 0° C.

To this solution, 0.53 ml (7.16 mmol) of ethanethiol was added, and the solution was stirred for 10 minutes and then heated, with stirring, to 120° C. for 3 hours.

This reaction mixture was poured into a saturated aqueous solution of sodium chloride and extracted with ethyl acetate. The extracted layer was washed with a saturated aqueous solution of sodium chloride and water, dried over anhydrous magnesium sulfate and concentrated.

The residue was chromatographed on silica gel and eluted with a mixed solvent of hexane and ethyl acetate (7:1), whereby 2-t-butyl-3-ethoxy-1-(3-hydroxyphenyl)-1-methoxy-1-propene (Compound [94]) was obtained in the form of a colorless oil in a yield of 492 mg (51.8%).

HNMR (300 MHz, CDCl$_3$): δ 1.13 (t, J=7.0 Hz, 3H), 1.28 (s, 9H), 3.24 (s, 3H), 3.29 (q, J=7.0 Hz, 2H), 3.69 (s, 2H), 4.78–4.83 (m, 1H), 6.81 (ddd, J=8.0, 2.6 and 0.9 Hz, 1H), 6.87 (s, with fine coupling, 1H), 6.94 (d with fine coupling J=7.6 Hz, 1H), 7.22 (dd, J=8.0 and 7.6 Hz, 1H) ppm.

IR (liquid film): 3320, 2956, 2872, 1634, 1596, 1582 cm$^{-1}$.

Mass (m/z, %): 264 (M$^+$, 30), 249 (6), 219 (13), 207 (100), 203 (64), 161 (51).

EXAMPLE 75

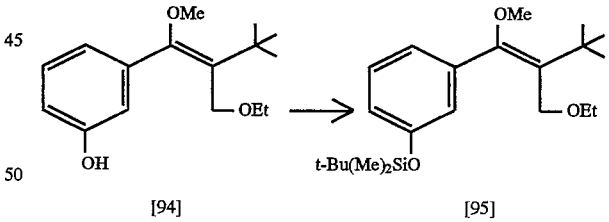

[94]   [95]

124 mg (0.470 mmol) of 2-t-butyl-3-ethoxy-1-(3-hydroxyphenyl)-1-methoxy-1-propene (Compound [94]) synthesized in Example 74 was dissolved in 1.5 ml of anhydrous DMF, and the solution was stirred in an atmosphere of argon at room temperature.

To this solution, 69 mg (1.01 mmol) of imidazole and 137 mg (0.909 mmol) of t-butyldimethylchlorosilane were added, and the mixture was stirred for 8 hours and 40 minutes.

This reaction solution was then poured into water and extracted with ethyl acetate. The extracted layer was washed with a saturated aqueous solution of sodium chloride and water, dried over anhydrous magnesium sulfate and concentrated.

The residue was chromatographed on silica gel and eluted with a mixed solvent of hexane and dichloromethane (1:1), whereby 2-t-butyl-1-[3-(t-butyldimethylsiloxy)phenyl]-3-ethoxy-1-methoxy-1-propene (Compound [95]) was obtained in the form of a colorless oil in a yield of 152 mg (85.6%).

$^1$HNMR (300 MHz, CDCl$_3$): δ 0.20 (s, 6H), 0.99 (s, 9H), 1.12 (t, J=7.0 Hz, 3H), 1.28 (s, 9H), 3.23 (s, 3H), 3.26 (q, J=7.0 Hz, 2H), 3.70 (s, 2H), 6.80 (ddd, J=8.1, 2.5 and 1.0 Hz, 1H), 6.86 (s with fine coupling, 1H), 6.95 (d with fine coupling, J=7.6 Hz, 1H), 7.19 (dd, J=8.1 and 7.6 Hz, 1H) ppm.

IR (liquid film): 2956, 2936, 2864, 1634, 1598, 1578, 1260, 1086 cm$^{-1}$.

Mass (m/z, %): 378 (M$^+$, 31), 333 (13), 322 (25), 321 (100), 319 (15), 317 (31).

EXAMPLE 76

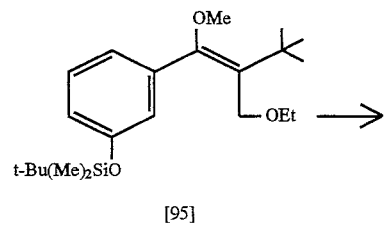

[95]

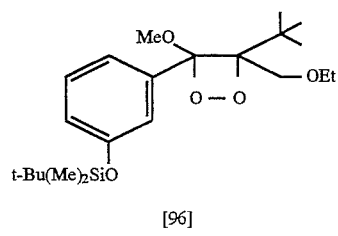

[96]

105 mg (0.278 mmol) of 2-t-butyl-1-[3-(t-butyldimethylsiloxy)phenyl]-3-ethoxy-1-methoxy-1-propene (Compound [95]) synthesized in Example 75 and 4 mg of TPP were added to 30 ml of dichloromethane, and this solution was stirred in an atmosphere of oxygen at 0° C.

This solution was then irradiated with a sodium lamp (180 W) for 7 hours.

The reaction mixture was concentrated, and the residue was chromatographed on silica gel and eluted with a mixed solvent of hexane and dichloromethane (2:1), whereby 3-t-butyl-4-[3-(t-butyldimethylsiloxy)phenyl]-3-ethoxymethyl-4-methoxy-1,2-dioxetane (Compound [96]) was obtained in the form of a pale yellow oil in a yield of 88 mg (77.3%).

$^1$HNMR (300 MHz, CDCl$_3$): δ 0.20 (s, 3H), 0.20 (s, 3H), 0.81 (t, J=7.0 Hz, 3H), 0.99 (s, 9H), 1.28 (s, 9H), 2.48–2.62 (m, 1H), 2.94 (dq, J=9.2 and 7.0 Hz, 1H), 3.04 (s, 3H), 3.52 (d, J=10.1 Hz, 1H), 3.71 (d, J=10.1 Hz, 1H), 6.80–7.30 (m, 4H), ppm.

IR (liquid film): 2960, 2936, 1604, 1586, 1256, 1106 cm$^{-1}$.

Mass (m/z, %): 378 (M$^+$–32, 8), 321 (13), 266 (25), 208 (24), 209 (100), 177 (33), 149 (18).

EXAMPLE 77

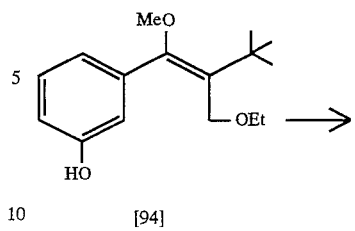

[94]

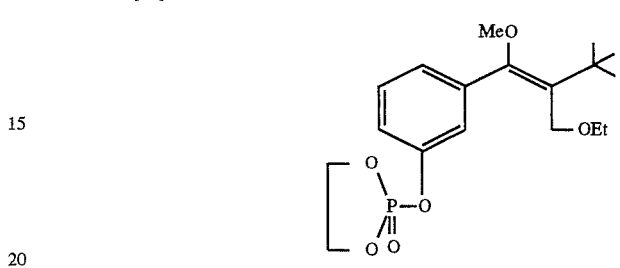

[97]

483 mg (1.83 mmol) of 2-t-butyl-3-ethoxy-1-(3-hydroxyphenyl)-1-methoxy-1-propene (Compound [94]) synthesized in Example 74 was added to 6 ml of anhydrous toluene, and the solution was stirred in an atmosphere of argon at 0° C.

To this solution, 0.31 ml (2.22 mmol) of triethylamine and 0.175 ml (1.89 mmol) of 2-chloro-1,3,2-dioxaphosphoran-2-oxide were successively added, and the mixture was stirred at 0° C. for 10 minutes, and then at room temperature for 50 minutes.

The reaction mixture was concentrated and diethyl ether was added thereto, so that insoluble components were filtered out from the mixture.

The filtrate was concentrated, whereby a crude 3-(2-t-butyl-3-ethoxy-1-methoxy-1-propen-1-yl) phenylethylenephosphate (Compound [97]) was obtained in the form of a colorless oil.

$^1$HNMR (300 MHz, CDCl$_3$): δ 1.15 (t, J=7.0 Hz, 3H), 1.28 (s, 9H), 3.24 (s, 3H), 3.30 (q, J=7.0 Hz, 2H), 3.66 (s, 2H), 4.27–4.60 (m, 4H), 7.12–7.38 (m, 4H) ppm.

EXAMPLE 78

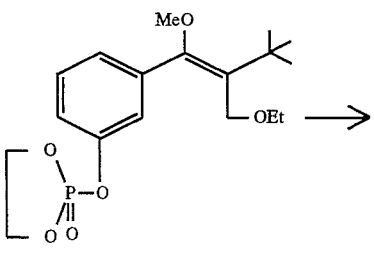

[97]

-continued

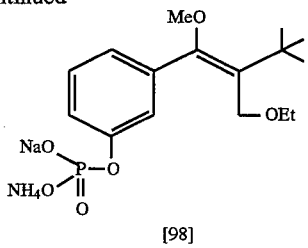

[98]

680 mg of the crude 3-(2-t-butyl-3-ethoxy-1-methoxy-1-propen-1-yl)phenylethylenephosphate (Compound [97]) synthesized in Example 77 was added to 8 ml of anhydrous DMF, And the solution was stirred in an atmosphere of argon at room temperature.

To this solution, 94 mg (1.82 mmol) of sodium cyanide (95%) was added, and the mixture was stirred overnight.

The reaction mixture was concentrated, and 5 ml of 28% ammonia water and 2 ml of THF were added thereto. The mixture was stirred for one day.

This reaction mixture was concentrated, and the residue was dissolved in water and washed with hexane.

The aqueous layer was subjected to freeze-drying, whereby a crude product of ammonium sodium 3-(2-t-butyl-3-ethoxy-1-methoxy-1-propen-1-yl)phenylphosphate (Compound [98]) was obtained in the form of a colorless amorphous solid in a yield of 733 mg.

$^1$HNMR (300 MHz, CD$_3$OD): δ 1.13 (t, J=7.0 Hz, 3H), 1.31 (s, 9H), 3.28 (s, 3H), 3.29 (q, J=7.0 Hz, 2H), 3.79 (s, 2H), 7.03 (d with fine coupling, J=7.1 Hz, 1H), 7.20 (broad s, 1H), 7.29 (dd, J=8.3 and 7.1 Hz, 1H), 7.35 (d, J=8.3 Hz, 1H), ppm.

IR (KBr): 2960, 2868, 1634, 1600, 1580, 1296, 1110 cm$^{-1}$.

Mass (FAB-pos, m/z, %): 389 ([M+H–NH$_4$+Na]$^+$, 28), 343 (24), 329 (23), 125 (100), 115 (19).

EXAMPLE 79

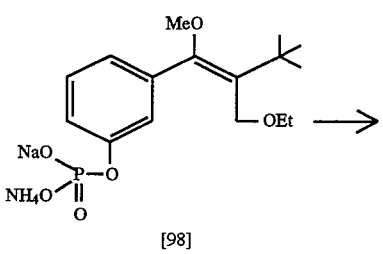

[98]

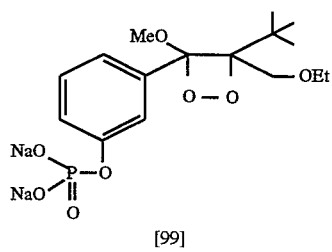

[99]

106 mg (0.277 mmol) of ammonium sodium 3(2-t-butyl-3-ethoxy-1-methoxy-1-propen-1-yl)phenylphosphate (Compound [98]) synthesized in Example 78 and 4 mg of TPP were dissolved in 30 ml of dichloromethane, and the solution was stirred in an atmosphere of oxygen at 0° C.

This solution was irradiated with a sodium lamp (180 W) for 8 hours.

The reaction mixture was concentrated, and methanol was added thereto, so that insoluble components were filtered out from the mixture.

The filtrate was concentrated, and the residue was dissolved in a mixed solvent composed of 2 ml of methanol and 2 ml of a 0.1% aqueous solution of sodium hydrogencarbonate, and filtered through a 0.45 μ polytetrafluoroethylene filter.

0.3 ml of the filtrate was subjected to HPLC using an octadecyl group introduced polymeric reversed phase column, and a fraction which was eluted with a gradient elution by using a 0.1% aqueous solution of sodium hydrogencarbonate and acetonitrile was subjected to freeze-drying, whereby a freeze-dried product was obtained.

Methanol was added to the thus obtained freeze-dried product, the portion which was soluble in the methanol was concentrated, whereby a crude product of 3-t-butyl-3-ethoxymethyl-4-methoxy-4(3'-phosphoryloxy)phenyl-1,2-dioxetane disodium salt (Compound [99]) was obtained in the form of a colorless amorphous solid.

$^1$HNMR (300 MHz, CD$_3$OD): δ0.87 (t, J=7.0 Hz, 3H), 1.30 (s, 9H), 2.54–2.68 (m, 1H), 2.97 (dq, J=9.0 and 7.0 Hz, 1 H), 3.05 (s, 3H), 3.51 (d, J=10.2 Hz, 1 H), 3.76 (d, J=10.2 Hz, 1H), 6.96–7.10 (m, 1 H), 7.24–7.44 (m, 2 H), 7.56–7.68 (m, 1 H) ppm.

Mass (FAB-pos, m/z, %): 443 ([M+Na]$^+$, 20), 421 ([M+H]$^+$, 24), 299 (22), 277 (23), 207 (17), 115 (100).

EXAMPLE 80

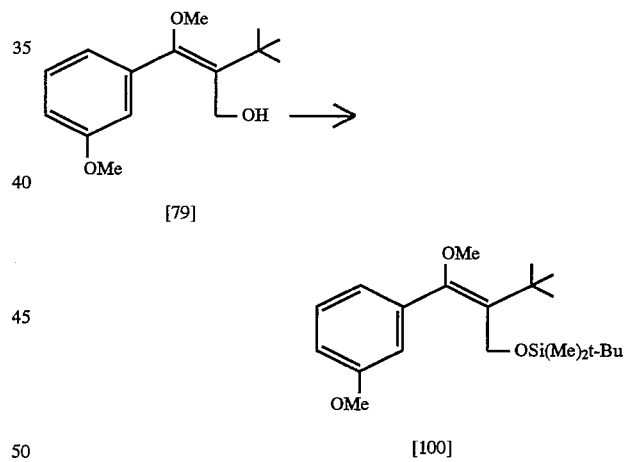

316 mg (1.26 mmol) of 2-t-butyl-3-methoxy-3-(3-methoxyphenyl)-2-propen-1-ol (Compound [79]) synthesized in Example 59 was dissolved in 4 ml of anhydrous DMF, and the solution was stirred in an atmosphere of argon at room temperature.

To this solution, 180 mg (2.64 mmol) of imidazole and 286 mg (1.90 mmol) of t-butyldimethylchlorosilane were added, and the mixture was stirred for 1 hour.

This reaction mixture was poured into a saturated aqueous solution of sodium chloride and extracted with ethyl acetate. The extracted layer was washed with a saturated aqueous solution of sodium chloride and water, dried over anhydrous magnesium sulfate and concentrated.

The residue was chromatographed on silica gel and eluted with a mixed solvent of hexane and dichloromethane (2:1), whereby 2-t-butyl-3-(t-butyldimethylsiloxy)-1-methoxy-1-(3-methoxyphenyl)-1-propene (Compound [100]) was obtained in the form of a colorless oil in a yield of 438 mg (95.2%).

¹HNMR (300 MHz, CDCl₃): δ–0.12 (s, 6 H), 0.86 (s, 9 H), 1.28 (s, 9 H), 3.23 (s, 3 H), 3.81 (s, 3 H), 3.89 (s, 2 H), 6.82–6.91 (m, 1H), 6.88 (s, 1 H), 6.96 (d with fine coupling, J=7.5 Hz, 1 H), 7.18–7.29 (m, 1 H) ppm.

IR (liquid film): 2956, 2932, 2860, 1638, 1596, 1580, 1254, 1046 cm⁻¹.

Mass (m/z, %): 364 (M⁺, 5), 308 (24), 307 (100), 251 (19), 233 (65), 201 (61), 177 (17).

EXAMPLE 81

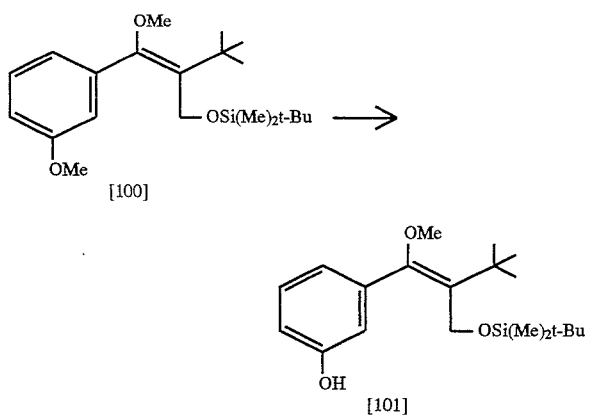

484 mg (1.33 mmol) of 2-t-butyl-3-(t-butyldimethylsiloxy)-1-methoxy-1-(3-methoxyphenyl)-1-propene (Compound [100]) and 106 mg (2.65 mmol) of sodium hydride (60%) were added to 5 ml of anhydrous DMF, and the solution was stirred in an atmosphere of argon at 0° C.

To this solution, 0.19 ml (2.57 mmol) of ethanethiol was added, and the mixture was stirred for 15 minutes and then heated to 1200° C., with stirring, for 3 hours.

This reaction mixture was poured into a saturated aqueous solution of sodium chloride and extracted with ethyl acetate. The extracted layer was washed with a saturated aqueous solution of sodium chloride and water, dried over anhydrous magnesium sulfate and concentrated.

The residue was chromatographed on silica gel and eluted with a mixed solvent of hexane and ethyl acetate (10:1), whereby 2-t-butyl-3-(t-butyldimethylsiloxy)-1-(3-hydroxyphenyl)-1-methoxy-1-propene (Compound [101]) was obtained in the form of a colorless amorphous solid in a yield of 221 mg (47.5%).

¹HNMR (300 MHz, CDCl₃): δ–0.10 (s, 6 H), 0.87 (s, 9 H), 1.27 (s, 9 H), 3.24 (s, 3H), 3.88 (s, 2 H), 4.57–4.67 (m, 1H), 6.79 (ddd, J=8.1, 2.6 and 0.9 Hz, 1H), 6.85 (s with fine coupling, 1 H), 6.94 (d with fine coupling, J=76. Hz, 1 H), 7.20 (dd, J=8.1 and &.6 Hz, 1 H) ppm.

IR (KBr): 3320, 2956, 2860, 1642, 1598, 1254, 1048 cm⁻¹.

Mass (m/z, %): 350 (M⁺, 4), 294 (22), 293 (100), 261 (14), 237 (19), 219 (64), 203 (18), 187 (76), 163 (22), 161 (18), 199 (24).

EXAMPLE 82

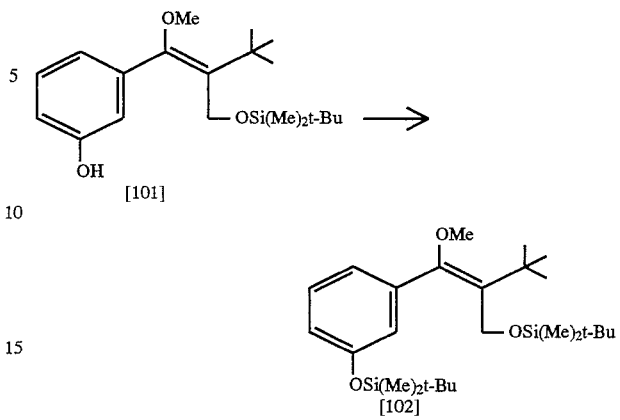

278 mg (0.794 mmol) of 2-t-butyl-3-(t-butyldimethylsiloxy)-1-(3-hydroxyphenyl)-1-methoxy-1-propene (Compound [101]) synthesized in Example 81 was dissolved in 3 ml of anhydrous DMF, and the solution was stirred in an atmosphere of argon at room temperature.

To this solution, 115 mg (1.69 mmol) of imidazole and 228 mg (1.51 mmol) of t-butyldimethylchlorosilane were added, and the mixture was stirred overnight.

This reaction mixture was poured into a saturated aqueous solution of sodium chloride and extracted with ethyl acetate. The extracted layer was successively washed with a saturated aqueous solution of sodium chloride and with water, dried over anhydrous magnesium sulfate and concentrated.

The residue was chromatographed on silica gel and eluted with a mixed solvent of hexane and dichloromethane (3:1), whereby 2-t-butyl-3-(t-butyldimethylsiloxy)-1-[3-(t-butyldimethylsiloxy)phenyl]-1-methoxy-1-propene (Compound [102]) was obtained in the form of a colorless oil in a yield of 270 mg (73.3%).

¹HNMR (300 MHz, CDCl₃): δ–0.14 (s, 6 H), 0.19 (s, 6H), 0.85 (s, 9 H), 0.98 (s, 9 H), 1.28 (s, 9 H), 3.22 (s, 3 H), 3.90 (s, 2 H), 6.76–6.83 (m, 2 H), 6.96 (d with fine coupling, J=7.6 Hz, 1 H), 7.17 (dd, J=8.8 and 7.6 Hz, 1 H) ppm.

IR (liquid film): 2960, 2936, 2860, 1640, 1596, 1578, 1256, 1046 cm⁻¹.

Mass (m/z, %): 464 (M⁺, 5), 408 (34), 407 (100), 350 (19), 334 (20), 333 (66), 302 (21), 301 (80).

EXAMPLE 83

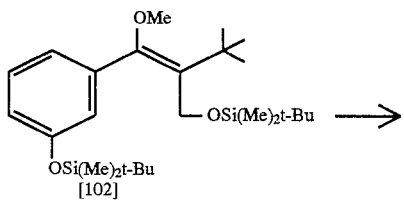

-continued

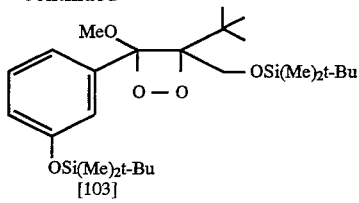
[103]

80 mg (0.172 mmol) of 2-t-butyl-3-(t-butyldimethylsiloxy)-1-[3-(t-butyldimethylsiloxy)phenyl]-1-methoxy-1-propene (Compound [102]) and 2 mg of TPP were dissolved in 20 ml of dichloromethane, and the solution was stirred in an atmosphere of oxygen at room temperature.

This solution was irradiated with a sodium lamp (180 W) for 3 hours.

The reaction mixture was concentrated, and the residue was chromatographed on silica gel and eluted with a mixed solvent of hexane and dichloromethane (4:1), whereby 3-t-butyl-3-[(t-butyldimethylsiloxy)methyl]-4-[3-(t-butyldimethylsiloxy)phenyl]-4-methoxy-1,2dioxetane (compound [103]) was obtained in the form of a colorless oil in a yield of 70 mg (81.9%).

$^1$HNMR (300 MHz, CDCl$_3$): δ–0.44 (s, 3 H), –0.21 (s, 3 H), 0.20 (s, 6 H), 0.73 (s, 9 H), 0.98 (s, 9 H), 1.31 (s, 9 H), 3.00 (s, 3 H), 3.64 (d, J=10.8 Hz, 1 H), 4.08 (d, J=10.8 Hz, 1 H), 6.78–7.28 (m, 4 H) ppm.

IR (liquid film): 2960, 2932, 2860, 1602, 1586, 1256, 1086 cm$^{-1}$.

Mass (m/z, %): 464 (M$^+$–32, trace), 266 (28), 210 (22), 209 (100), 177 (19), 173 (73), 115 (23).

EXAMPLE 84

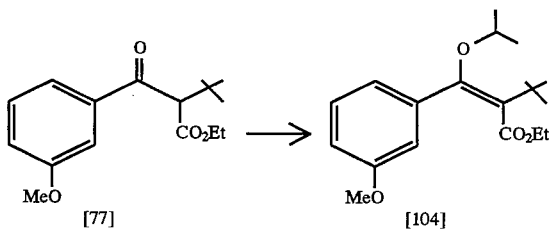
[77]   [104]

4.00 g (14.4 mmol) of ethyl 2-butyl-2-(3-methoxybenzoyl)acetate (compound [77]) synthesized in Referenced Example 12 was added to 30 ml of anhydrous DMSO, and the solution was stirred in an atmosphere of argon at room temperature.

To this solution, 3.26 g (29.1 mmol) of potassium t-butoxide was added, and the solution was stirred for 15 minutes. To this solution, 2.7 ml (28.8 mmol) of isopropyl bromide was added, and the solution was stirred for 4 hours. To this solution, 11.02 g(98.2 mmol) of potassium t-butoxide and 9.3 ml (99.0 mmol) of isopropyl bromide were further added, separated in 5 portions, over a period of 24 hours.

The reaction mixture was poured into a saturated aqueous solution of sodium chloride and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (9:1), whereby ethyl 2-t-butyl-3-isopropoxy-3-(3-methoxyphenyl)-2-propenoate (Compound [104]) was obtained in the form of a colorless oil in a yield of 3.73 g(81.0%).

$^1$HNMR (300 MHz, CDCl$_3$): δ0.86 (t, J=7.1 Hz, 3 H), 1.15 (d, J=6.2 Hz, 6H), 1.30 (s, 9 H), 3.79 (s, 3 H), 3.79 (q, J=7.2 Hz, 2 H), 3.87 (hept, J=6.2 Hz), 1H), 6.83 (ddd, J=8.2, 2.6 and 0.8 Hz, 1 H), 6.87 (s with fine coupling, 1 H), 6.91 (dd, J=7.5 and 0.9 Hz, 1 H), 7.21 (dd, J=8.2 and 7.5 Hz, 1 H) ppm.

IR (liquid film): 2976, 1718, 1632, 1598, 1580 cm$^{-1}$.

Mass (m/z, %): 320 (37), 275 (12), 263 (15), 233 (24), 232 (94), 217 (55), 176 (20), 135 (100).

EXAMPLE 85

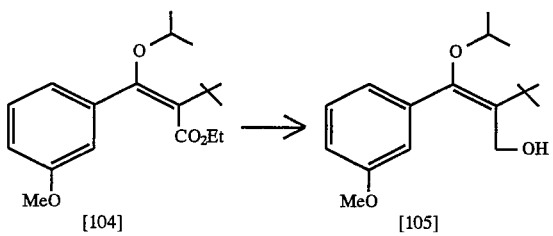
[104]   [105]

3.72 g (11.6 mmol) of ethyl 2-t-butyl-3-isopropoxy-3-(3-methoxyphenyl)-2-propenoate (Compound [104]) synthesized in Example 84 was added to 35 ml of anhydrous toluene, and the solution was stirred in an atmosphere of argon at =78° C. To this solution, 15.0 ml (26.4 mmol) of diisobutylaluminum hydride (25% hexane solution) was added, and the solution was stirred for 4 hours.

The reaction mixture was poured into a mixture of water and ethyl acetate, with stirring, at 0° C., and the mixture was stirred for 20 minutes.

This reaction mixture was filtered through Celite, and the organic layer was separated therefrom and washed with a saturated aqueous solution of sodium chloride, dried over magnesium sulfate and concentrated.

The residue was chromatographed on silica gel and eluted with a mixed solvent of hexane and ethyl acetate (4:1), whereby 2-t-butyl-3-isopropoxy-3-(3-methoxyphenyl)-2-propen-1-ol (Compound [105]) was obtained in the form of a colorless oil in a yield of 2.47 g (76.4%).

$^1$HNMR (300 MHz, CDCl$_3$): δ0.89 (t, J=5.6 Hz, 1 H), 1.12 (d, J=6.2 Hz, 6 H), 1.33 (s, 9 H), 3.75 (hept, J=6.2 Hz, 1 H), 3.82 (s, 3 H), 3.89 (d, J=5.6 Hz, 2 H), 6.82–6.92 (m, 3 H), 7.23–7.31 (m, 1 H) ppm.

IR (liquid film): 3460, 2976, 1628, 1598, 1580 cm$^{-1}$.

Mass (m/z, %): 278 (M$^+$, 31), 261 (20), 219 (46), 218 (24), 203 (54), 135 (100), 107 (20).

EXAMPLE 86

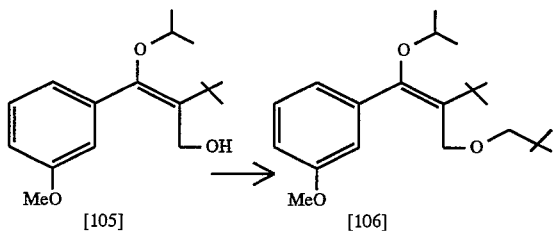
[105]   [106]

1.195 g (4.30 mmol) of 2-t-butyl-3-isopropoxy-3-(3-methoxyphenyl)-2-propen-1ol (Compound [105]) synthesized in Example 85 was added to 12 ml of anhydrous DMF, and the solution was stirred in an atmosphere of argon at room temperature.

To this solution, 325 mg (8.13 mmol) of sodium hydride (60%) and 1.20 ml (9.53 mmol) of neopentyl bromide were added, and the mixture was stirred at 100° for 1 hour.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (20:1), whereby 2-t-butyl-1-isopropoxy-1-(3-methoxyphenyl)-3-neopentyloxy-1-propene (Compound [106]) was obtained in the form of a colorless oil in a yield of 1.194 g (79.8%).

$^1$HNMR (300 MHz, CDCl$_3$): δ0.88 (s, 9 H), 1.12 (d, J=6.2 Hz, 6 H), 1.29 (s, 9 H), 2.76 (s, 2 H), 3.56 (s, 2 H), 3.77 (hept, J=6.2 Hz, 1 H), 3.80 (s, 3 H), 6.84 (ddd, J=8.0, 2.7 and 1.0 Hz, 1 H), 6.87 (s with fine coupling, 1 H), 6.94 (d with fine coupling, J=7.5 Mz, 1 H), 7.22 (dd with fine coupling, J=8.0 and 7.5 Hz, 1 H), ppm.

IR (liquid film): 1956, 1858, 1632, 1598, 1580 cm$^{-1}$

Mass (m/z, %): 348 (M$^+$, 50), 291 (40), 261 (18), 219 (43), 218 (23), 203 (75), 179 (27), 135 (100), 107 (18).

EXAMPLE 87

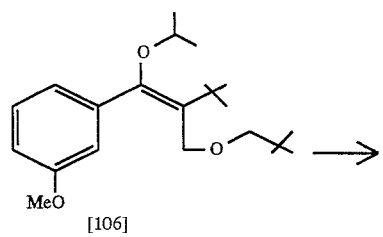
[106]

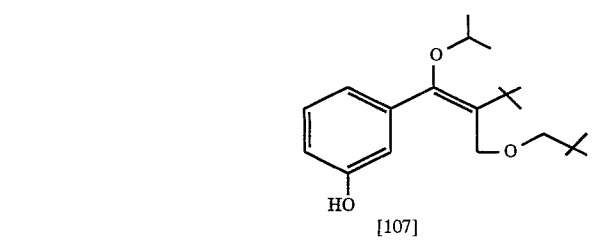
[107]

0.8 ml (10.8 mmol) of ethanethiol was added to a suspension of 389 mg (9.73 mmol) of sodium hydride (60%) suspended in 15 ml of anhydrous DMF at 0° C., and the solution was stirred for 20 minutes.

To this solution, a solution of 1.522 g (4.37 mmol) of 2-t-butyl-1-isopropoxy-1-(3-methoxyphenyl)-3-neopentyloxy-1-propene (Compound [106]) synthesized in Example 86 in 10 ml of anhydrous DMF was added, and the mixture was stirred at 120° C. for 6 hours.

This reaction mixture was poured into a saturated aqueous solution of sodium chloride and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (10:1 to 4:1), whereby 2-t-butyl-1-(3-hydroxyphenyl)-1-isopropoxy-3-neopentyloxy-1-propene (Compound [107]) was obtained in the form of a pale yellow oil in a yield of 1.208 g (82.7%).

$^1$HNMR (300 MHz, CDCl$_3$): δ0.90 (S, 9 H), 1.12 (d, J=6.1 Hz, 6 H), 1.27 (s, 9 H), 2.76 (s, 2 H), 3.53 (s, 2 H), 3.79 (hept, J=6.1 Hz, 1 H), 4.65 (s, 1 H), 6.78 (ddd, J=8.1, 1.6 and 0.9 Hz, 1 H), 6.84 (s, with fine coupling, 1 H), 6.92 (d with fine coupling, J=7.6 Hz, 1 H), 7.18 (dd, J=8.1 and 7.6 Hz, 1 H) ppm.

IR (liquid film): 3400, 2960, 2872, 1628 cm$^{-1}$.

Mass (M/z, %): 334 (M$^+$, 41), 277 (35), 247 (23), 205 (55), 204 (37), 189 (72), 165 (26), 121 (100), 93 (16).

EXAMPLE 88

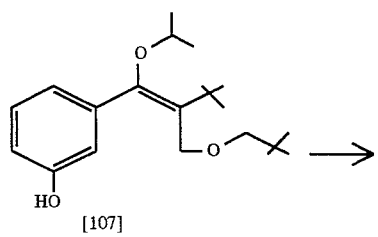
[107]

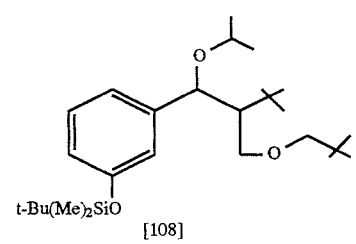
[108]

122 mg (0.365 mmol) of 2-t-butyl-1-(3-hydroxyphenyl)-1-isopropoxy-3-neopentyloxy-1-propene (Compound [107]) synthesized in Example 87 was dissolved in 2 ml of anhydrous DMF, and the solution was stirred in an atmosphere of argon at room temperature.

To this solution, 0.15 ml (1.08 mmol) of triethylamine and 110 mg (0.730 mmol) of t-butyldimethylchlorosilane were added, and the mixture was stirred overnight.

This reaction mixture was poured into water and extracted with ethyl acetate. The extracted layer was washed with saturated aqueous solution of sodium chloride, dried over magnesium sulfate and concentrated.

The residue was chromatographed on silica gel and eluted with a mixed solvent of hexane and ethyl acetate (25:1), whereby 2-t-butyl-1-[3-(t-butyldimethylsiloxy)phenyl]-1-isopropoxy-3-neopentyloxy-1-propene (Compound [108]) was obtained in the form of a colorless oil in a yield of 121 mg (73.9%).

$^1$HNMR (300 MHz, CDCl$_3$): δ0.18 (s, 6 H), 0.87 (s, 9H), 0.98 (s, 9 H), 1.11 (d, J=6.2 Hz, 6 H), 1.28 (s, 9 H), 2.75 (s, 2 H), 3.58 (s, 2 H), 3.74 (hept, J=6.2 Hz, 1 H), 6.75–6.82 (m, 2 H), 6.93 (d with fine coupling, J=7.6 Hz, 1 H), 7.15 (dd, J=7.6 and 7.4 Hz, 1 H), ppm.

IR (liquid film): 2956, 2864, 1630, 1596, 1578, 1260, 1086 cm$^{-1}$

Mass (m/z, %): 448 (M$^+$100), 391 (70), 361 (26), 319 (56), 318 (25), 303 (52), 279 (30), 261 (74), 235 (45).

EXAMPLE 89

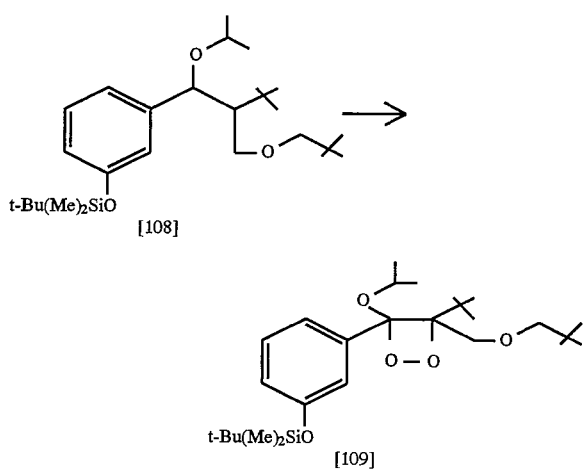

68 mg (0.152 mmol) of 2-t-butyl-1-[3-(t-butyldimethylsiloxy)phenyl]-1-isopropoxy-3-neopentyloxy-1-propene (Compound [108]) synthesized in Example 88 and 4 mg of TPP were dissolved in 20 ml of dichloromethane, and the solution was stirred in an atmosphere of oxygen at 0° C.

This solution was irradiated with a sodium lamp (180 W) for 2 hours. This reaction mixture was concentrated, chromatographed on silica gel and eluted with a mixed solvent of hexane and ethyl acetate (100:1), whereby 3-t-butyl-4-[3-(t-butyldimethylsiloxy)phenyl]-4-isopropoxy-3-neopentyloxymethyl-1,2-dioxetane (Compound [109]) was obtained in the form of a colorless oil in a yield of 52 mg (71.4%).

¹HNMR (300 MHz, CDCl₃): δ0.21 (broad s, 6 H), 0.72 (s, 9 H), 0.90–1.10 (m, 12 H), 1.15–1.30 (m, 3H), 1.32 (s, 9 H), 2.10–2.24 (m, 1 H), 2.56 (d, J=8.3 Hz, 1 H), 3.32 (d, J=10.1 Hz, 1 H), 3.40–3.64 (m, 2 H), 6.70–6.96 (m, 2 H), 7.14–7.40 (m, 2 H), ppm.

IR (liquid film): 2960, 2936, 2868, 1602, 1586, 1256, 1100 cm⁻¹,

Mass (m/z, %): 448 (M⁺–32, 7), 294 (45), 238 (25), 237 (67), 235 (25), 196 (36), 195 (100), 167 (19), 135 (21), 71 (54), 57 (70).

EXAMPLE 90

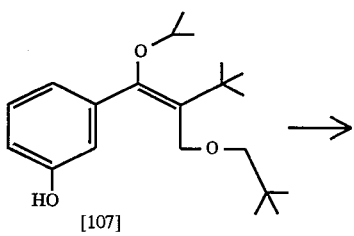

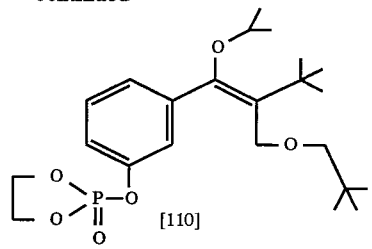

504 mg (1.51 mmol) of 2-t-butyl-1-(3-hydroxyphenyl)-1-isopropoxy-3-neopentyloxy-1-propene (Compound [107]) synthesized in Example 87 was added to 6 ml of anhydrous toluene, and the solution was stirred in an atmosphere of argon at 0° C.

To this solution, 0.25 ml (1.79 mmol) of triethylamine and 0.136 ml (0.147 mmol) of 2-chloro-1,3,2-dioxaphosphoran-2-oxide were successively added, and the mixture was stirred at 0° C. for 10 minutes and then at room temperature for 3 hours.

This reaction mixture was concentrated and diethyl ether was added thereto. Insoluble components were filtered out from the reaction mixture.

The filtrate was concentrated, whereby a crude 3-(2-t-butyl-1-isopropoxy-3-neopentyloxy-1-propen-1-yl)phenylethylenephosphate (Compound [110]) was obtained in the form of a colorless oil in a yield of 664 mg.

¹HNMR (300 MHz, CDCl₃): δ0.90 (s, 9 H), 1.12 (d, =6.2 Hz, 6 H), 1.28 (s, 9 H), 2.77 (s, 2 H), 3.51 (s, 2 H), 3.74 (hept, J=6.2 Hz, 1 H), 4.20–4.57 (m, 4 H), 7.11–7.35 (m, 4 H) ppm.

EXAMPLE 91

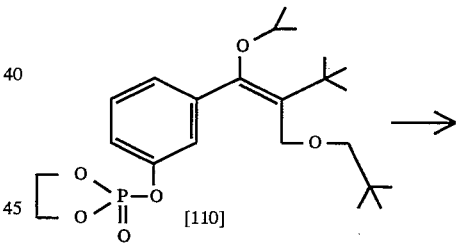

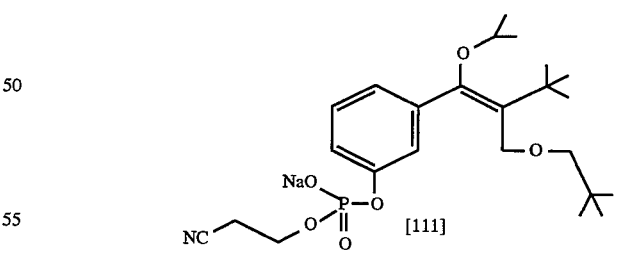

664 mg (1.51 mmol) of 3-(2-t-butyl-1-isopropoxy-3-neopentyloxy-1-propen-1-yl)phenylethylenephosphate (Compound [110]) synthesized in Example 90 was added to 7 ml of anhydrous DMF, and the solution was stirred in an atmosphere of argon at room temperature.

To this solution, 80 mg (1.55 mmol) of sodium cyanide (95%) was added, and the mixture was stirred overnight.

This reaction mixture was concentrated. The residue was dissolved in water and subjected to freeze-drying, whereby a crude sodium (3-(2-t-butyl-1-isopropoxy-3-neopentyloxy-1-propene-1yl)phenyl-2'-cyanoethylphosphate (Compound [111]) was obtained in the form of a colorless amorphous solid in a yield of 730 mg.

¹HNMR (300 MHz, CD₃OD): δ0.93 (s, 9 H), 1.17 (d, J=6.1 Hz, 6 H), 1.33 (s, 9 H), 1.80 (t, J=6.2 Hz, 2 H), 2.81 (s, 2 H), 3.64 (s, 2 H), 3.87 (hept, J=6.1 Hz, 1 H), 4.15 (dt, J=7.8 and 6.2 Hz, 2 H), 7.04–7.40 (m, 4 H) ppm.

EXAMPLE 92

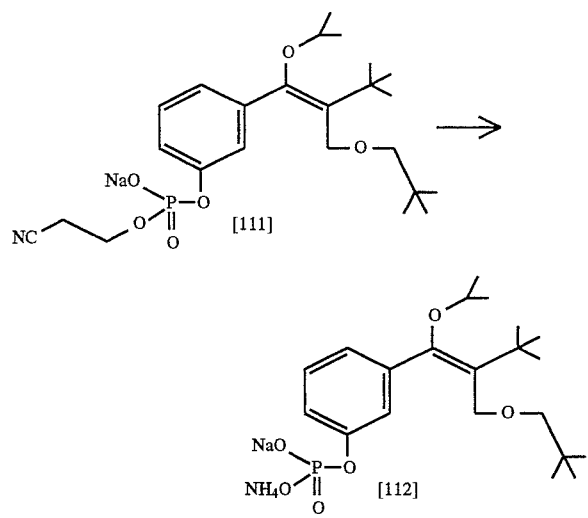

710 mg of the crude sodium 3-(2-t-butyl-1-isopropoxy-3-neopentyloxy-1-propen-1-yl)phenyl-2'-cyanoethylphosphate (Compound [111]) synthesized in Example 91 was added to 3 ml of THF, and the solution was stirred in an atmosphere of argon at room temperature.

To this solution, 5 ml of 28% ammonia water was added, and the mixture was stirred for 2 days.

This reaction mixture was concentrated. The residue was dissolved in water and washed with hexane. The aqueous layer was subjected to freeze-drying, whereby a crude ammonium sodium 3-I(2-t-butyl-1-isopropoxy-3-neopentyloxy-1-propen-1-yl)phenylphosphate (Compound [112]) was obtained in the form of a colorless amorphous solid in a yield of 562 mg.

¹HNMR (300 MHz, CD₃OD): δ0.92 (s, 9 H), 1.15 (d, J=6.2 Hz, 6 H), 1.33 (s, 9 H), 2.80 (s, 2 H), 3.65 (s, 2 H), 3.89 (hept, J=6.2 Hz, 1 H), 7.05 (d, J=7.5 Hz, 1 H), 7.13 (s with fine coupling, 1 H), 7.25 (dd, J=8.2 and 7.5 Hz, 1 H), 7.37 (d with fine coupling, J=8.2 Hz, 1 H) ppm.

IR (KBr): 2956, 2868, 1627, 1599, 1578, 1294, 1110 cm⁻¹.

Mass (FAB-pos, m/z, %): 459 ([M+H=NH₄+Na]⁺, 28), 431 (22), 329 (100), 307 (43), 125 (67), 115 (35).

EXAMPLE 93

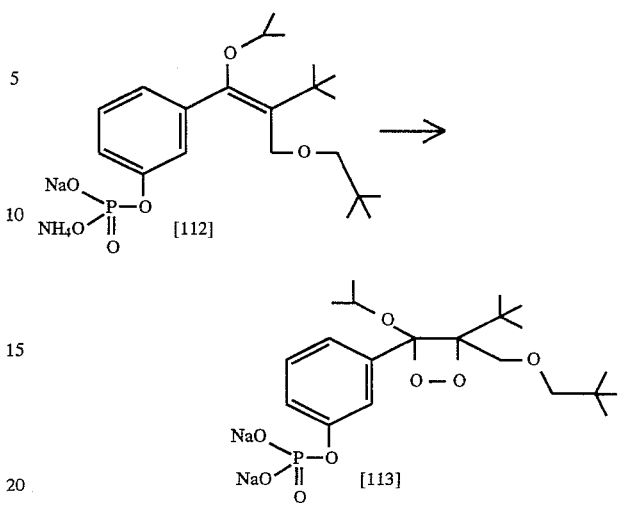

198 mg (0.438 mmol) of ammonium sodium 3-(2-t-butyl-1-isopropoxy-3-neopentyloxy-1-propen-1-yl)phenylphosphate (Compound [112]) synthesized in Example 92 and 4 mg of TPP were dissolved in 30 ml of dichloromethane, and the solution was stirred in an atmosphere of oxygen at 0° C.

This solution was irradiated with a sodium lamp (180 W) for 4 hours.

The reaction mixture was concentrated and methanol was added thereto. Insoluble components were filtered out from the mixture.

The filtrate was concentrated, and the residue was dissolved in a mixed solvent of 1 ml of methanol and 1 ml of a 0.1% aqueous solution of sodium hydrogencarbonate, and filtered through a 0.45 µ polytetrafluoroethylene filter.

The filtrate was subjected to HPLC using an octadecyl group introduced polymeric reversed phase column, and a fraction which was eluted with a gradient elution by using a 0.1% aqueous solution of sodium hydrogencarbonate and acetonitrile was subjected to freeze-drying, whereby a freeze-dried product was obtained.

The thus obtained freeze-dried product was dissolved in water and subjected to PHLC using an octadecyl group introduced polymeric reversed phase column, and a fraction which was desalted by a gradient elution using water and acetonitrile was subjected to freeze-drying, whereby 3-t-butyl-4-isopropoxy-3-neopentyloxymethyl-4-(3'-phosphoryloxy)phenyl-1,2-dioxetane disodium salt (Compound [113]) was obtained in the form of an amorphous solid in a yield of 80 mg (37.4%).

¹HNMR (300 MHz, DC₃OD): δ0.79 (s, 9 H), 1.00–1.13 (m, 3 H), 1.21 (d, J=6.1 Hz, 3 H), 1.37 (s, 9 H), 2.24–2.37 (m, 1 H), 2.60 (d, J=8.2 Hz, 1 H), 3.23–3.40 (m, 1 H), 3.50–3.70 (m, 2 H), 6.82–6.87 (m, 1 H), 7.20–7.40 (m, 1 H), 7.52–7.70 (m, 2 H) ppm.

IR (KBr): 2976, 2872, 1588, 1270, 1104 cm⁻¹.

Mass (FAB-pos, m/z, %): 513 ([M+Na]⁺, 17), 491 ([M+H]⁺, 37), 429 (50), 407 (29), 327 (52), 305 (100), 263 (38), 125 (65), 115 (49).

Reference Example 13

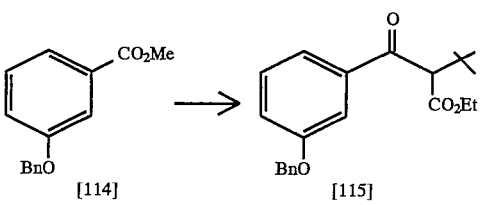

25.0 ml (0.178 mol) of diisopropylamine was added to 200 ml of anhydrous THF in an atmosphere of argon at room temperature, and the solution was stirred.

To this solution, 110 ml (0.178 mol) of butyl lithium (1.62M hexane solution) was added, and the solution was stirred for 1 hour.

This solution was cooled to −78° C. and 30.0 ml (0.178 mol) of ethyl t-butylacetate was added thereto. The mixture was stirred for 30 minutes and 21.0 g (86.8 mmol) of methyl 3-benzyloxybenzoate (Compound [114]) was added thereto. The mixture was stirred at room temperature for 3 hours.

This reaction mixture was poured into 1N hydrochloric acid and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (9:1), whereby ethyl 2-(3-benzyloxybenzoyl)-2-t-butylacetate (Compound [115]) was obtained in a yield of 28.31 g (92.2%).

Melting point: 53.5°–54.0° C. (colorless fine particle-shaped crystals, recrystallized from methanol)

$^1$HNMR (300 MHz, CDCl$_3$): δ1.14 (s, 9 H), 1.18 (t, J=7.1 Hz, 3 H), 4.13 (q, J=7.1 Hz, 2 H), 4.26 (s, 1 H), 5.11 (s, 2 H), 7.18 (d with fine coupling, J=8.2 Hz, 1 H), 7.32–7.48 (m, 6 H), 7.52–7.59 (m, 2 H) ppm.

IR (KBr): 2964, 1728, 1696, 1592 cm$^{-1}$.

Mass (m/z, %): 354 (M$^+$, 19), 298 (18), 211 (39), 91 (100).

EXAMPLE 94

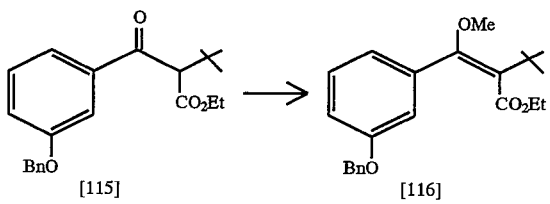

28.1 g (79.4 mmol) of ethyl 2-(3-benzyloxybenzoyl)-2-t-butylacetate (Compound [115]) synthesized in Reference Example 13 was added to 200 ml of anhydrous DMSO, and the solution was stirred in an atmosphere of nitrogen at room temperature.

To this solution, 20.1 g (0.179 mol) of potassium t-butoxide was added, and the solution was stirred for 15 minutes.

This solution was cooled to 0° C., and 15.0 ml (0.158 mol) of dimethyl sulfate was added dropwise thereto over a period of 15 minutes, and the solution was stirred at room temperature for 30 minutes.

This solution was cooled to 0° C., and 7.30 g (65.1 mmol) of potassium t-butoxide and then 5.4 ml (56.9 mmol) of dimethyl sulfate, separated into two portions, were successively added thereto over a period of 4 hours and 30 minutes, and the mixture was stirred at room temperature.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (10:1), whereby ethyl 3-(3-benzyloxyphenyl)-2-t-butyl-3-methoxy-2-propenoate (Compound [116]) was obtained in the form of a colorless oil in a yield of 24.9 g (85.2%).

$^1$HNMR (300 MHz, CDCl$_3$): δ0.90 (t, J=7.2 Hz, 3 H), 1.29 (s, 9 H), 3.30 (s, 3 H), 3.85 (q, J=7.1 Hz, 2 H), 5.06 (s, 2 H), 6.90–7.01 (m, 3 H), 7.22 (t, J=7.8 Hz, 1 H), 7.28–7.47 (m, 5 H) ppm.

IR (liquid film): 2960, 1718, 1636, 1596, 1580 cm$^{-1}$.

Mass (m/z, %): 368 (M$^+$, 59), 354 (25), 353 (100), 91 (83).

EXAMPLE 95

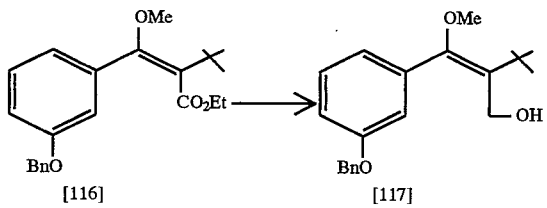

19.63 g (53.3 mmol) of ethyl 3-(3-benzyloxyphenyl)-2-t-butyl-3-methoxy-2-propenoate (Compound [116]) synthesized in Example 94 was added to 150 ml of anhydrous toluene, and the solution was stirred in an atmosphere of argon at −78° C.

To this solution, 70.0 ml (0.123 mol) of diisobutylaluminum hydride (15% toluene solution) was added, and the solution was stirred for 45 minutes. To this solution, 7.0 ml (12.3 mmol) of diisobutylaluminum hydride (25% toluene solution) was further added, and the mixture was stirred for 2 hours.

This reaction mixture was poured into 1N hydrochloric acid and extracted with ethyl acetate. The extracted layer was washed with a saturated aqueous solution of sodium chloride, dried over magnesium sulfate and concentrated.

The residue was crystallized from a mixed solvent of hexane and ethyl acetate, whereby 3-(3-benzyloxyphenyl)-2-t-butyl-3-methoxy-2-propen-1-ol (Compound [117]) was obtained in a yield of 8.70 g (50.0%).

The filtrate was concentrated, chromatographed on silica gel and eluted with a mixed solvent of hexane and ethyl acetate (4:1), whereby 3-(3-benzyloxyphenyl)-2-t-butyl-3-methoxy-2-propen-1-ol (Compound [117]) was also obtained in a yield of 6.80 g (39.1%).

Melting point: 59.5°–60.0° C. (colorless particle-shaped crystals, recrystallized from hexane and ethyl acetate)

$^1$HNMR (300 MHz, CDCl$_3$): δ0.94 (t, J=5.4 Hz, 1 H), 1.31 (s, 9 H), 3.23 (s, 3 H), 3.92 (d, J=5.4 Hz, 2 H), 5.09 (s, 2 H), 6.90–7.00 (m, 3 H), 7.25–7.47 (m, 6 H) ppm.

IR (KBr): 3464, 2956, 1634, 1588 cm$^{-1}$.

Mass (m/z, %): 326 (M$^+$, 46), 311 (43), 269 (39), 91 (100).

EXAMPLE 96

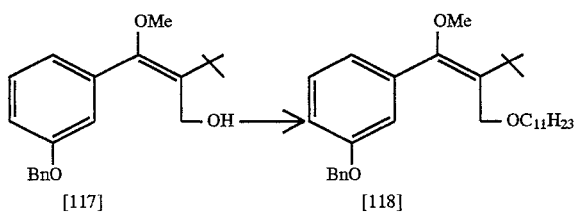

772 mg (2.37 mmol) of 3-(3-benzyloxyphenyl)-2-t-butyl-3-methoxy-2-propen-1-ol (Compound [117]) synthesized in Example 95 was added to 2.0 ml (8.96 mmol) of 1-bromoundecane, and the solution was stirred in an atmosphere of argon at room temperature.

To this solution, 2.0 ml (25.0 mmol) of a 50% aqueous solution of sodium hydroxide and 89 mg (0.276 mmol) of tetrabutylammonium bromide were added, and the solution was stirred at 80° C. for 3 hours.

To this solution, 99 mg (0.307 mmol) of tetrabutylammonium bromide was further added, and the mixture was stirred at 80° C. for 3 hours and 30 minutes.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (10:1), whereby 1-(3-benzyloxyphenyl)-2t-butyl-1-methoxy-3-undecanoxy-1-propene (Compound [118]) was obtained in the form of a colorless oil in a yield of 448 mg (39.4%).

$^1$HNMR (300 Mz, CDCl$_3$): δ0.84–0.92 (m, 3 H), 1.20–1.36 (m, 16 H), 1.28 (s, 9 H), 1.44–1.56 (m, 2H, 3.20 (t, J=6.6 Hz, 2 H), 3.23 (s, 3 H), 3.67 (s, 2 H), 5.07 (s, 2 H), 6.95 (d with fine coupling, J=8.2 Hz, 1 H), 6.99 (d, J=7.6 Hz, 1 H), 7.05 (s with fine coupling, 1 H), 7.25 (dd, J=8.2 and 7.6 Hz, 1 H), 7.28–7.48 (m, 5 H) ppm.

IR (liquid film): 2928, 2956, 1636, 1596, 1580 cm$^{-1}$.

Mass (m/z, %): 480 (M$^+$, 28), 424 (31), 423 (100), 333 (19), 309 (16), 91 (67).

EXAMPLE 97

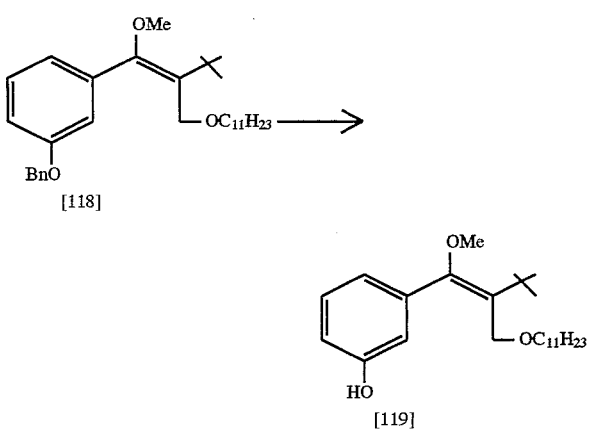

718 mg (1.50 mmol) of 1-(3-benzyloxyphenyl)-2-t-butyl-1-methoxy-3-undecanoxy-1-propene (Compound [118]) synthesized in Example 96 and 125 mg of 10% Pd-C were added to a mixed solvent of 7 ml of ethyl acetate and 2 ml of methanol. The mixture was stirred in an atmosphere of hydrogen at room temperature for 2 hours.

The reaction mixture was filtered through Celite and the filtrate was concentrated. The residue was chromatographed on silica gel and eluted with a mixed solvent of hexane and ethyl acetate (5:1), whereby 2-t-butyl-1-(3-hydroxyphenyl)-1-methoxy-3-undecanoxy-1-propene (Compound [119]) was obtained in the form of a color less oil in a yield of 528 mg (90.5%).

$^1$HNMR (300 MHz, CDCl$_3$): δ0.84–0.92 (m, 3 H), 1.18–1.35 (m, 16 H), 1.27 (s, 9 H), 1.43–1.59 (m, 2 H), 3.21 (t, J=6.5 Hz, 2 H), 3.24 (s, 3 H), 3.66 (s, 2 H), 6.80 (ddd, J=8.0, 2.6 and 0.8 MHz, 1 H), 6.86 (s with fine coupling, 1 H), 6.95 (d with fine coupling, J=7.6 Hz, 1 H), 7.21 (dd, J=8.0 and 7.6 Hz, 1 H), ppm.

IR (liquid film): 3384, 2928, 1856, 1636, 1596, 1584 cm$^{-1}$.

Mass (M/z, %): 390 (M$^+$, 16), 334 (23), 333 (100), 219 (17), 203 (32), 179 (22), 161 (20).

EXAMPLE 98

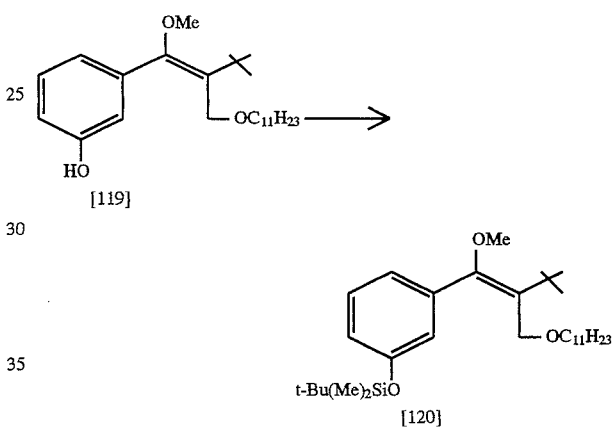

84 mg (0.215 mmol) of 2-t-butyl-1-(3-hydroxyphenyl)-1-methoxy-3-undecanoxy-1-propene (Compound [119]) synthesized in Example 97 was dissolved in 1.5 ml of DMF, and the solution was stirred in an atmosphere of argon at room temperature.

To this solution, 30 mg (0.441 mmol) of imidazole and 60 mg (0.398 mmol) of t-butyldimethylchlorosilane were added, and the solution was stirred for 2 hours.

To this solution, 18 mg (0.264 mmol) of imidazole and 36 mg (0.239 mmol) of t-butyldimethylchlorosilane were further added, and the solution was stirred for 1 hour.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (20:1), whereby 2-t-butyl-1-[3-(t-butyldimethylsiloxy)phenyl]-1-methoxy-3-undecanoxy-1-propene (Compound [120]) was obtained in the form of a colorless oil in a yield of 100 mg (92.1%).

$^1$HNMR (300 MHz, CDCl$_3$): δ0.19 (s, 6H), 0.84–0.92 (m, 3 H), 0.99 (s, 9 H), 1.18–1.35 (m, 16 H), 1.28 (s, 9 H), 1.42–1.53 (m, 2 H), 3.17 (t, J=6.6 Hz, 2 H), 3.23 (s, 3 H), 3.68 (s, 2 H), 6.80 (ddd, J=8.1, 2.5 and 0.9 Hz, 1 H), 6.84 (s with fine coupling, 1 H), 6.96 (d with fine coupling, J=7.6 Hz, 1 H), 7.18 (dd, J=8.1 and 7.6 Hz, 1 H) ppm.

EXAMPLE 99

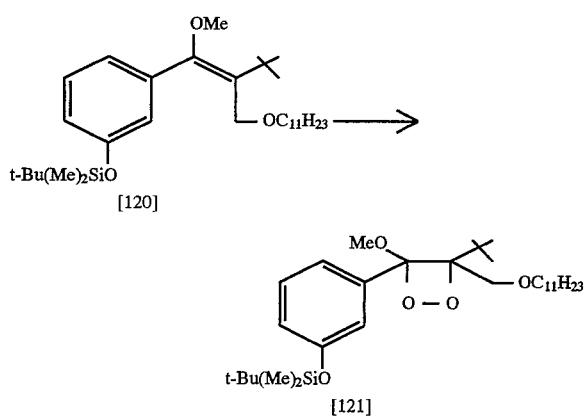

60 mg (0.119 mmol) of 2-t-butyl-1-[3-(t-butyldimethylsiloxy)phenyl]-1-methoxy-3-undecanoxy-1-propene (Compound [120]) synthesized in Example 98 an d5 mg of TPP were dissolved in 20 ml of dichloromethane, and the solution was stirred in an atmosphere of oxygen at 0° C.

This solution was irradiated with a sodium lamp (180 W) for 3 hours.

This reaction mixture was concentrated. The residue was subjected to preparative TLC and developed with a mixed solvent of hexane and benzene (20:1), whereby 3-t-butyl-4-[3-(t-butyldimethylsiloxy)phenyl]-4-methoxy-3-undecanoxymethyl-1,2-dioxetane (Compound [121]) was obtained in the form of a colorless oil in a yield of 38 mg (59.6%).

$^1$HNMR (300 MHz, CDCl$_3$): δ0.20 (s, 6 H), 0.84–0.92 (m, 3 H), 0.99 (s, 9 H), 1.02–1.35 (m, 18 H), 1.28 (s, 9 H), 2.47 (dt, J=9.0 and 6.2 Hz, 1 H), 2.87 (dt, J=9.0 and 6.4 Hz, 1 H), 3.03 (s, 3 H), 3.50 (d, J=10.1 Hz, 1 H), 3.72 (d, J=10.1 Hz, 1 H), 6.84 (dd, J=8.0, 2.4 and 1.0 Hz, 1 H), 6.90–7.18 (m, 2 H), 7.24 (t, J=8.0 Hz, 1 H), ppm.

EXAMPLE 100

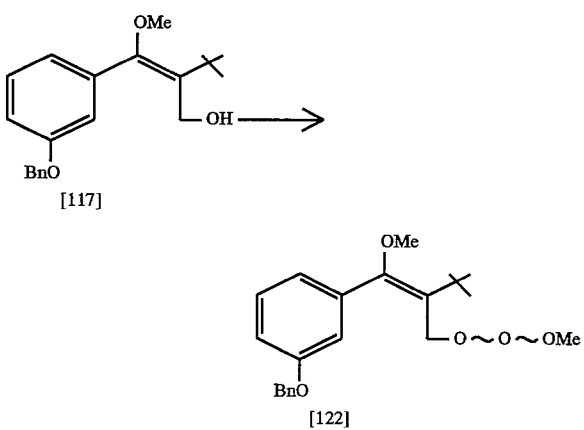

652 mg (2.00 mmol) of 3-(3-benzyloxyphenyl)-2-t-butyl-3-methoxy-2-propen-1-ol (Compound [117]) synthesized in Example 95 and 0.55 ml (4.05 mmol) of 2-(2-methoxyethoxy)ethyl bromide were dissolved in 4 ml of THF, and the solution was stirred in an atmosphere of argon at room temperature.

To this solution, 408 mg (10.2 mmol) of sodium hydroxide, 67 mg (0.208 mmol) of tetrabutylammonium-bromide and 0.1 ml of water were added, and the solution was refluxed, with stirring, for 8 hours and 40 minutes.

To this solution, 0.60 ml (4.42 mmol) of 2-(2-methoxyethoxy)ethyl bromide, 530 mg (13.3 mmol) of sodium hydroxide and 69 mg (0.214 mmol) of tetrabutylammonium bromide were further added, and the mixture was refluxed, with stirring, overnight.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (4:1), whereby 1-(3-benzyloxyphenyl)-2-t-butyl-1-methoxy-3-[2-(2-methoxyethoxy)ethoxy]-1-propene (Compound [122]) was obtained in the form of a colorless oil in a yield of 591 mg (69.0%).

$^1$HNMR (300 MHz, CDCl$_3$): δ1.28 (s, 9 H), 3.22 (s, 3 H), 3.34 (s, 3 H), 3.37–3.42 (m, 2 H), 3.46–3.51 (m, 2 H), 3.54–3.61 (m, 4 H), 3.77 (s, 2 H), 5.07 (s, 2 H), 6.92–7.02 (m, 3 H), 7.22–7.48 (m, 6 H), ppm.

IR (liquid film): 2876, 1636, 1596, 1580 cm$^{-1}$.

Mass (m/z, %): 428 (M$^+$, 49), 371 (10), 309 (16), 308 (13), 293 (26), 251 (67), 217 (29), 91 (100).

EXAMPLE 101

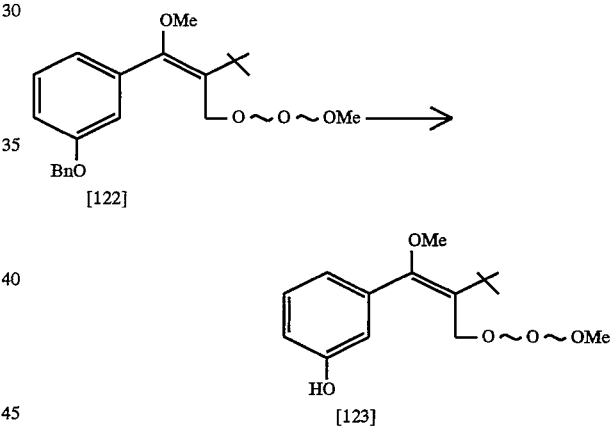

451 mg (1.05 mmol) of 1-(3-benzyloxyphenyl)-2-t-butyl-1-methoxy-3-[2-(2-methoxyethoxy)ethoxy]-1-propene (Compound [122]) synthesized in Example 100 and 54 mg of 10% Pd-C were added to 7 ml of a mixed solvent of ethyl acetate and methanol (5:2), and the mixture was stirred in an atmosphere of hydrogen at room temperature for 2 hours and 30 minutes.

This reaction mixture was filtered through Celite, and the filtrate was concentrated. The residue was chromatographed on silica gel and eluted with a mixed solvent of hexane and ethyl acetate (2:1), whereby 2-t-butyl-1-(3-hydroxyphenyl)-1-methoxy-3-[2-(2-methoxyethoxy)ethoxy]-1-propene (Compound [123]) was obtained in the form of a colorless oil in a yield of 300 mg (84.2%).

$^1$HNMR (300 MHz, CDCl$_3$): δ1.26 (s, 9 H), 3.29 (s, 3 H), 3.40–3.46 (m, 2 H), 3.44 (s, 3 H), 3.62 (s, 2 H), 3.60–3.74 (m, 6 H), 6.80–6.87 (m, 2 H), 7.18–7.25 (m, 2 H) ppm.

IR (liquid film): 3380, 2956, 2928, 2876, 1634, 1596, 1582 cm$^{-1}$.

Mass (m/z, %): 338 (M⁺, 77), 281 (33), 219 (30), 218 (23), 203 (73), 161 (100), 103 (36), 59 (31).

EXAMPLE 102

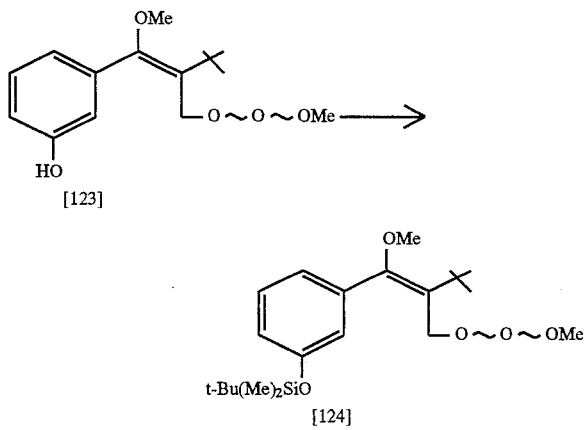

135 mg (0.399 mmol) of 2-t-butyl-1-(3-hydroxyphenyl)-1-methoxy-3-[2-(2-methoxyethoxy)ethoxy]-1-propene (Compound [123]) synthesized in Example 101 was dissolved in 2 ml of anhydrous DMF, and the solution was stirred in an atmosphere of argon at room temperature.

To this solution, 0.11 ml (0.789 mmol) of triethylamine and 78 mg (0.518 mmol) of t-butyldimethylchlorosilane were added, and the mixture was stirred for 1 hour and 30 minutes.

To this solution, 0.10 ml (0.717 mmol) of triethylamine and 58 mg (0.385 mmol) of t-butyldimethylchlorosilane were further added, and the mixture was stirred for 1 hour.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (4:1), whereby 2-t-butyl-1-[3-(t-butyldimethylsiloxy)phenyl]-1-methoxy-3-[2-(2-methoxyethoxy)ethoxy]-1-propene (Compound [124]) was obtained in the form of a colorless oil in a yield of 173 mg (95.8%).

¹HNMR (300 MHz, CDCl₃): δ0.19 (s, 6 H), 0.99 (s, 9 H), 1.28 (s, 9 H), 3.22 (s, 3 H), 3.37 (s, 3 H), 3.34–3.40 (m, 2 H), 3.49–3.62 (m, 6 H), 3.78 (s, 2 H), 6.77–6.83 (m, 2 H), 6.95 (d with fine coupling, J=7.6 Hz, 1 H), 7.19 (dd, J=8.7 and 7.6 Hz, 1 H) ppm.

IR (liquid film): 2956, 2936, 2864, 1636, 1596, 1578 cm⁻¹.

Mass (m/z %): 452 (M⁺, 55), 395 (11), 333 (27), 317 (45), 376 (29), 275 (100).

EXAMPLE 103

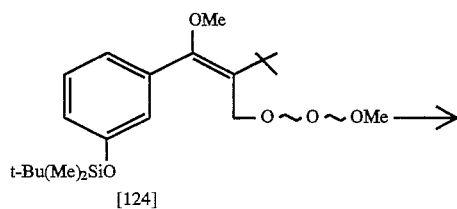

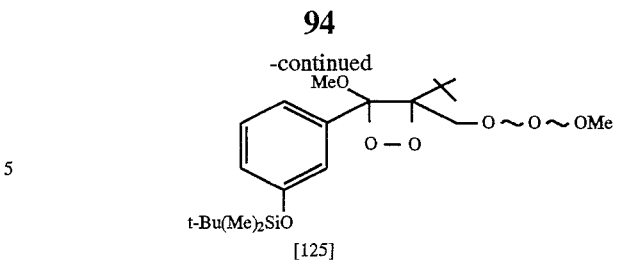

54 mg (0.119 mmol) of 2-t-butyl-1-[3-(t-butyldimethylsiloxy)phenyl]-1-methoxy-3-[2-(2-methoxyethoxy)ethoxy]-1-propene (Compound [124]) synthesized in Example 102 and 10 mg of TPP were dissolved in 20 ml of dichloromethane, and the solution was stirred in an atmosphere of oxygen at 0° C.

This solution was irradiated with a sodium lamp (180 W) for 8 hours.

This reaction solution was concentrated. The residue was chromatographed on silica gel and eluted with dichloromethane and then with a mixed solvent of dichloromethane and ethyl acetate (25:1), whereby 3-t-butyl-4-[3-(t-butyldimethylsiloxy)phenyl]-4-methoxy-3-[2-(2-methoxyethoxy)ethoxy]-1,2-dioxetane (Compound [125]) was obtained in the form of a pale yellow oil in a yield of 38 mg (65.7%).

¹HNMR (300 MHz, CDCl₃): δ0.20 (s, 6 H), 0.99 (s, 9 H), 1.28 (s, 9 H), 2.66–2.77 (m, 1 H), 2.99–3.10 (m, 1 H), 3.04 (s, 3 H), 3.20–3.32 (m, 2 H), 3.35 (s, 3 H), 3.40–3.52 (m, 4 H), 3.61 (d, J=10.3 Hz, 1 H), 3.77 (d with fine coupling, J=10.3 Hz, 1 H), 6.81–6.87 (m, 1 H), 6.92–7.30 (m, 3 H), ppm.

IR (liquid film): 2935, 2888, 1604, 1586, 1256, 1104 cm⁻².

Mass (m/z, %): 452 (M⁺–32, 1), 266 (27), 210 (22), 209 (100), 177 (19).

EXAMPLE 104

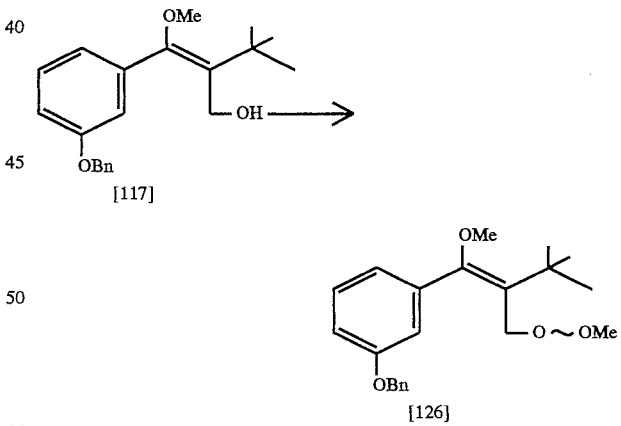

824 mg (2.53 mmol) of 3-(3-benzyloxyphenyl)-2-t-butyl-3-methoxy-2-propen-1-ol (Compound [117]) synthesized in Example 95 was dissolved in 10 ml of anhydrous DMF, and the solution was stirred in the atmosphere of argon at room temperature.

To this solution, 202 mg (5.05 mmol) of sodium hydride (60%), 0.48 ml (5.11 mmol) of 2-methoxyethyl bromide and 73 mg (0.226 mmol) of tetrabutylammonium bromide were added, and the solution was stirred at 100° C. for 5 hours.

To this solution, 220 mg (5.50 mmol) of sodium hydride (60%), 0.50 ml (5.32 mmol) of 2-methoxyethyl bromide and 81 mg (0.310 mmol) of tetrabutylammonium bromide were added, and the solution was stirred at 100° C. for 7 hours and 30 minutes.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (10:1), whereby 1-(3-benzyloxyphenyl)-2-t-butyl-1-methoxy-3-(2-methoxyethoxy)-1-propene (Compound [126]) was obtained in a yield of 630 mg (64.9%).

Melting point: 48.0°–49.0° C. (colorless columns, recrystallized from methanol)

$^1$HNMR (300 MHz, CDCl$_3$): δ1.29 (s, 9 H), 3.22 (s, 3 H), 3.30 (s, 3 H), 3.34–3.40 (m, 2 H), 3.42–3.48 (m, 2 H), 3.78 (s, 2 H), 5.08 (s, 2 H), 6.92–7.00 (m, 2 H), 7.00–7.04 (m, 1 H), 7.22–7.48 (m, 6 H) ppm.

IR (KBr): 2952, 2928, 2900, 1628, 1596, 1582 cm$^{-1}$.

Mass (m/z, %): 384 (M$^+$, 27), 327 (10), 309 (11), 293 (21), 251 (55), 161 (13), 91 (100).

EXAMPLE 105

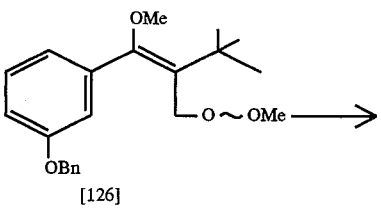

[126]

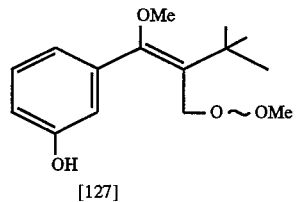

[127]

341 mg (0.888 mmol) of 1-(3-benzyloxyphenyl)-2-t-butyl-1-methoxy-3-(2-methoxyethoxy)-1-propane (Compound [126]) synthesized in Example 104 an d30 mg of 10% Pd-C were added to 4.5 ml of a mixed solvent of ethyl acetate and methanol (2:1), and the mixture was stirred in an atmosphere of hydrogen at room temperature for 5 hours.

This reaction mixture was filtered through Celite, and the filtrate was concentrated.

The residue was chromatographed on silica gel and eluted with a mixed solvent of hexane and ethyl acetate (5:1), whereby 2-t-butyl-1-(3-hydroxyphenyl)-1-methoxy-3-(2-methoxyethoxy)-1-propene (Compound [127]) was obtained in the form of a colorless oil in a yield of 236 mg (90.4%).

$^1$HNMR (300 MHz, CDCl$_3$): δ1.27 (s, 9 H), 3.34 (s, 3 H), 3.41–3.47 (m, 2 H), 3.48 (s, 3 H), 3.59–3.65 (m, 2 H), 3.64 (broad s, 2 H), 6.77 (s with fine coupling, 1 H), 6.83 (ddd, J=8.0, 2.6 and 0.9 Hz, 1 H), 6.89 (d with fine coupling, J=7.7 Hz, 1 H), 7.22 (dd, J=8.0 and 7.7 Hz, 1 H), 7.41 (broad s, 1 H), ppm.

IR (liquid film): 3384, 2952, 2836, 1634, 1596, 1582 cm$^{-1}$.

Mass (m/z, %): 294 (M$^+$, 32), 237 (24), 219 (20), 218 (24), 203 (87 ), 162 (26), 161 (100).

EXAMPLE 106

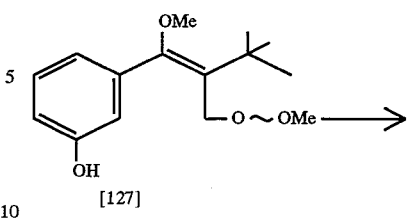

[127]

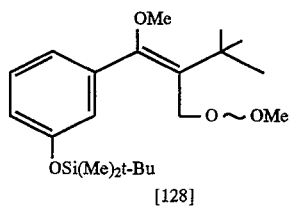

[128]

105 mg (0.357 mmol) of 2-t-butyl-1-(3-hydroxyphenyl)-1-methoxy-3-(2-methoxyethoxy)-1-propene (Compound [127]) synthesized in Example 105 was dissolved in 2 ml of anhydrous DMF, and the solution was stirred in an atmosphere of argon at room temperature.

To this solution, 52 mg (0.764 mmol) of imidazole and 98 mg (0.65 mmol) of t-butyldimethylchlorosilane were added, and the solution was stirred for 5 hours.

This reaction mixture was poured into water and extracted with ethyl acetate. The extracted layer was washed with a saturated aqueous solution of sodium chloride, dried over magnesium sulfate and concentrated.

The residue was chromatographed on silica gel and eluted with a mixed solvent of hexane and ethyl acetate (20:1), whereby 2-t-butyl-1-[3-(t-butyldimethylsiloxy)phenyl]-1-methoxy-3-(2-methoxyethoxy)-1-propene (Compound [128]) was obtained in the form of a colorless oil in a yield of 124 mg (85.1%).

$^1$HNMR (300 MHz, CDCl$_3$): δ0.19 (s, 6 H), 0.99 (s, 9 H), 1.28 (s, 9 H), 3.22 (s, 3 H), 3.33 (s, 3 H), 3.32–3.37 (m, 2 H), 3.41–3.47 (m, 2 H), 3.80 (s, 2 H), 6.77–6.84 (m, 1 H), 6.81 (d, J=1.4 Hz, 1 H), 6.94 (d with fine coupling, J=7.6 Hz, 1 H), 7.19 (dd, J=8.7 and 7.6 Hz, 1 H) ppm.

IR (liquid film): 2956, 1936, 1636, 1596, 1578, 1260 cm$^{-1}$.

Mass (m/z, %): 408 (M$^+$, 33), 351 (12), 333 (22), 317 (47), 276 (29), 275 (100), 249 (29), 219 (35), 179 (27), 121 (40).

EXAMPLE 107

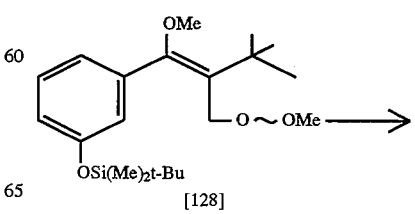

[128]

-continued

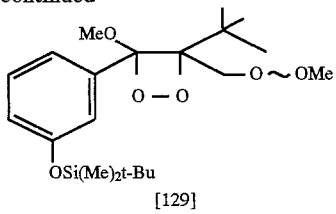

[129]

55 mg (0.135 mmol) of 2-t-butyl-1-[3-(t-butyldimethylsiloxy)phenyl]-1-methoxy-3-(2-methoxyethoxy)-1-propene (compound [128]) synthesized in Example 106 and 4 mg of TPP were dissolved in 20 ml of dichloromethane, and the solution was stirred in an atmosphere of oxygen at room temperature.

This solution was irradiated with a sodium lamp (180 W) for 6 hours and 30 minutes.

This reaction solution was concentrated. The residue was chromatographed on silica gel and eluted with dichloromethane and then with a mixed solvent of dichloromethane and ethyl acetate (50:1), whereby 3-t-butyl-4-[3-(t-butyldimethylsiloxy)phenyl]4-methoxy-3-(2-methoxyethoxy)methyl-1,2-dioxetane (Compound [129]) was obtained in the form of a pale yellow oil in a yield of 42 mg (70.8%).

$^1$HNMR (300 MHz, CDCl$_3$): δ0.20 (s, 6 H), 0.99 (s, 9 H), 1.28 (s, 9 H), 2.69 (dt, J=10.5 and 4.7 Hz, 1 H), 3.02 (dt, J=10.5 and 5.3 Hz, 1 H), 3.04 (s, 3 H), 3.16 (dd, H–5.3 and 4.7 Hz, 2 H), 3.23 (s, 3 H), 3.61 (d, J=10.3 Hz, 1 H), 3.77 (d, J=10.3 Hz, 1 H), 6.85 (d with fine coupling, J=8.0 Hz, 1 H), 6.90–7.20 (m, 2 H), 7.26 (dd, J=8.0 and 7.6 Hz, 1 H) ppm.

IR (liquid film): 2960, 2936, 1602, 1586, 1256, 1108 cm$^{-1}$.

Mass (m/z, %): 408 (M$^+$–32, 3), 266 (27), 210 (22), 209 (100), 177 (19), 89 (21).

EXAMPLE 108

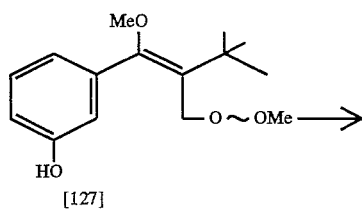

[127]

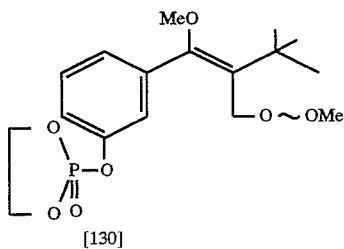

[130]

415 mg (1.41 mmol) of 2-t-butyl-1-(3-hydroxyphenyl)-1-methoxy-3-(2-methoxyethoxy)-1-propene (Compound [127]) synthesized in Example 105 was added to 6 ml of anhydrous toluene, and the solution was stirred in an atmosphere of argon at 0° C.

To this solution, 0.24 ml (1.72 mmol) of triethylamine and 0.13 ml (0.141 mmol) of 2-chloro-1,3,2-dioxaphosphoran-2-oxide were successively added, and the mixture was stirred at 0° C. for 20 minutes, and then at room temperature for 1 hour and 20 minutes.

This reaction mixture was concentrated, and diethyl ether was added thereto. Insoluble components were filtered out from the mixture and the filtrate was concentrated, whereby a crude 3-[2-t-butyl-1-methoxy-3-(2-methoxyethoxy)-1-propen-1-yl]phenylethylenephosphate (Compound [130]) was obtained in the form of a colorless oil in a yield of 560 mg.

$^1$HNMR (300 MHz, CDCl$_3$): δ1.28 (s, 9 H), 3.24 (s, 3 H), 3.35 (s, 3 H), 3.32–3.52 (m, 4 H), 3.37 (s, 2 H), 4.30–4.60 (m, 4 H), 7.12–7.39 (m, 4 H) ppm.

EXAMPLE 109

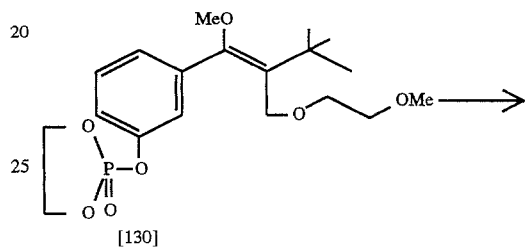

[130]

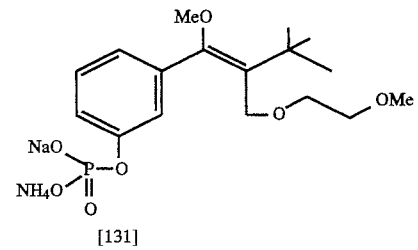

[131]

560 mg of the crude 3-[2-t-butyl-1-methoxy-3-(2-methoxyethoxy)-1-propen-1-yl]phenylethylenephosphate (Compound [130]) synthesized in Example 108 was added to 8 ml of anhydrous DMF, and the solution was stirred in an atmosphere of argon at room temperature.

To this solution, 73 mg (1.42 mmol) of sodium cyanide (95%) was added, and the mixture was stirred overnight.

This reaction mixture was concentrated, and 4 ml of 28% ammonia water was added thereto, and the mixture was stirred for 1 day.

This reaction mixture was concentrated. The residue was added to water and the mixture was washed with hexane. The aqueous layer was subjected to freeze-drying, whereby a crude ammonium sodium 3-[2-t-butyl-1-methoxy- 3-(2-methoxyethoxy)-1propen-1-yl]phenylphosphate (Compound [131]) was obtained in the form of a colorless amorphous solid in a yield of 525 mg.

$^1$ HNMR (300 MHz, CD$_3$OD): δ1.32 (s, 9 H), 3.29 (s, 3 H), 3.36 (s, 3 H), 3.35–3.42 (m, 2 H), 3.45–3.51 (m, 2 H), 3.84 (s, 2 H), 7.05 (d with fine coupling, J=6.8 Hz, 1 H), 7.22 (broad s, 1 H), 7.26–7.37 (m, 2 H) ppm.

IR (KBr): 2956, 1636, 1600, 1578, 1292, 1218 cm$^{-1}$.

Mass (FAB-pos, m/z, %): 419 ([M+H–NH$_4$+Na]$^+$, 84), 343 (37), 329 (26), 321 (48), 125 (100 ).

EXAMPLE 110

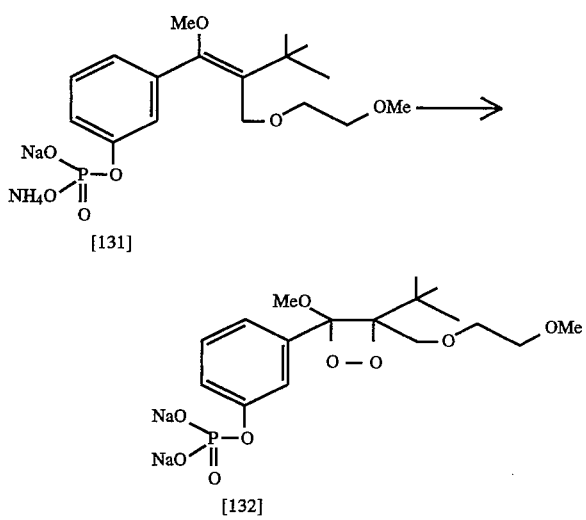

151 mg (0.366 mmol) of ammonium sodium 3-[2-t-butyl-1-methoxy-3-(2-methoxyethoxy)-1-propen-1-yl]phenylphosphate (Compound [131]) synthesized in Example 109 and 4 mg of TPP were dissolved in 30 ml of dichloromethane, and the solution was stirred in an atmosphere of oxygen at 0° C.

This solution was irradiated with a sodium lamp (180 W) for 7 hours.

The reaction mixture was concentrated and methanol was added thereto. Insoluble components were filtered out from the mixture.

The filtrate was concentrated, and the residue was dissolved in a mixed solvent of 3 ml of methanol and 3 ml of a 0.1% aqueous solution of sodium hydrogencarbonate, and filtered through a 0.45 µ polytetrafluoroethylene filter.

The filtrate was subjected to HPLC using an octadecyl group introduced polymeric reversed phase column, and a fraction which was eluted with a gradient elution by using a 0.1% aqueous solution of sodium hydrogencarbonate and acetonitrile was subjected to freeze-drying, whereby a freeze-dried product was obtained.

The thus obtained freeze-dried product was dissolved in water and subjected to HPLC using an octadecyl group introduced polymeric reversed phase column, and a fraction which was desalted by a gradient elution using water and acetonitrile was subjected to freeze-drying, whereby 3-t-butyl-4-methoxy-3-[(2-methoxyethoxy)methyl]-4-(3'-phosphoryloxy)phenyl-1,2-dioxetane disodium salt (Compound [132]) was obtained in the form of an amorphous solid in a yield of 43 mg (26.0%).

$^1$HNMR (300 MHz, CD$_3$OD): δ1.31 (s, 9 H), 2.70–2.79 (m, 1 H), 2.96–3.08 (m, 1H), 3.06 (s, 3 H), 3.20–3.30 (m, 2 H), 3.28 (s, 3 H), 3.61 (d, J=10.4 MHz, 1 H), 3.81 (d, J=10.4 MHz, 1 H), 6.98–7.14 (m, 1H), 7.26–7.42 (m, 2 H), 7.56–7.68 (m, 1 H) ppm.

IR (KBr): 1605, 1585, 1281, 1112 cm$^{-1}$.

Mass (FAB-pos, m/z, %): 473 ([M+Na]$^+$, 18), 451 ([M+H]$^+$, 10), 401 (60), 299 (100), 277 (56), 125 (56), 115 (28).

Test Example 1-1

3-isopropoxy-4,4-diisopropyl-3-(3'-phosphoryloxy)phenyl-1,2-dioxetane disodium salt (Compound [40]) synthesized in Example 26 was dissolved in a 0.1M diethanolamine/hydrochloric acid buffer solution (pH 10.0) containing 1 mM magnesium chloride and 0.05% sodium azide, in such an amount that the concentration of the dissolved Compound [40]) was 0.2 mg/ml, and the solution was stirred.

300 µl of this solution was placed in a cartridge for assay and incubated for 90 minutes.

After this incubation, 20 µl of an enzyme solution was added to the above solution, which enzyme solution was prepared by diluting an alkaline phosphatase solution for enzyme immunoassay (made by Boehringer Mannheim Co., Ltd.) (3 mg/0.3 ml) 154 times and then 10$^5$ times with a 50 mM Tris/cl buffer solution (pH 7.2) containing 0.15M sodium chloride, 1 mM magnesium chloride, 0.1 mM zinc chloride and 0.1% sodium azide.

The luminescence of the above diluted enzyme solution was measured at 37° C. at regular time intervals.

For comparison, the luminescence of a commercially available AMPPD (3-(2'-spiroadamantan)-4-methoxy-4-(3"-phosphoryloxy)phenyl-1,2-dioxetane disodium salt was measured under the same conditions as mentioned above, by replacing the Compound [40] with AMPPD in accordance with the above-mentioned procedure.

The results are shown in FIG. 1.

Test Example 1-2

1 mg of 3-isopropoxy-4,4-diisopropyl-3-(3'-phosphoryloxy)phenyl-1,2-dioxetane disodium salt (Compound [40]) synthesized in Example 26 was dissolved in methanol-d$_4$ (0.35 ml), and the solution was heated at 60° C. in a thermostated bath, so that the solution was subjected to $^1$HNMR measurement at intervals of 2 to 3 hours.

From the results of the $^1$HNMR measurement, the half-life of Compound [40] at 60° C. was calculated to be 14.3 hours.

In the above $^1$HNMR measurement, Compound [40] was replaced by the commercially available AMPPD (3-(2'-spiroadamantan)- 4-methoxy-4-(3"-phosphoryloxy)phenyl-1,2-dioxetane disodium salt), whereby the half-life of AMPPD at 60° C. was also calculated in the same manner as mentioned above.

The result was that the half-life of AMPPD at 60° was 5.5 hours.

Test Example 2-1

3-t-butyl-4-methoxy-3-neopentyloxymethyl-4-(3'-phosphoryloxy)phenyl-1,2-dioxetane disodium salt (Compound [86]) synthesized in Example 66 was dissolved in a 0.1M diethanolamine/hydrochloric acid buffer solution (pH 10.0 ) containing 0.4 mg/ml of quaternary ammonium salt (BDMG), 1 mM magnesium chloride and 0.05% sodium azide, in such an amount that the concentration of the dissolved Compound [86] was 0.2 mg/ml, and the solution was stirred.

300 µl of this solution was placed in a cartridge for assay and incubated for 90 minutes.

After this incubation, 20 µl of an enzyme solution was added to the above solution, which enzyme solution was prepared by diluting an alkaline phosphatase solution for enzyme immunoassay (made by Boehringer Mannheim Co., Ltd.) (3 mg/0.3 ml) 154 times with a 50 mM Tris/cl buffer solution (pH 7.2) containing 0.15M sodium chloride, 1 mM magnesium chloride, 0.1 mM zinc chloride and 0.1% sodium azide.

The luminescence of the above diluted enzyme solution was measured at 37° C. at regular time intervals.

For comparison, the luminescence of a commercially available AMPPD (3-(2'-spiroadamantan)-4-methoxy-4-(3"-phosphoryloxy)phenyl-1,2-dioxetane disodium salt) was measured under the same conditions as mentioned above, by replacing the Compound [86] with AMPPD in accordance with the above-mentioned procedure.

Figure 2:
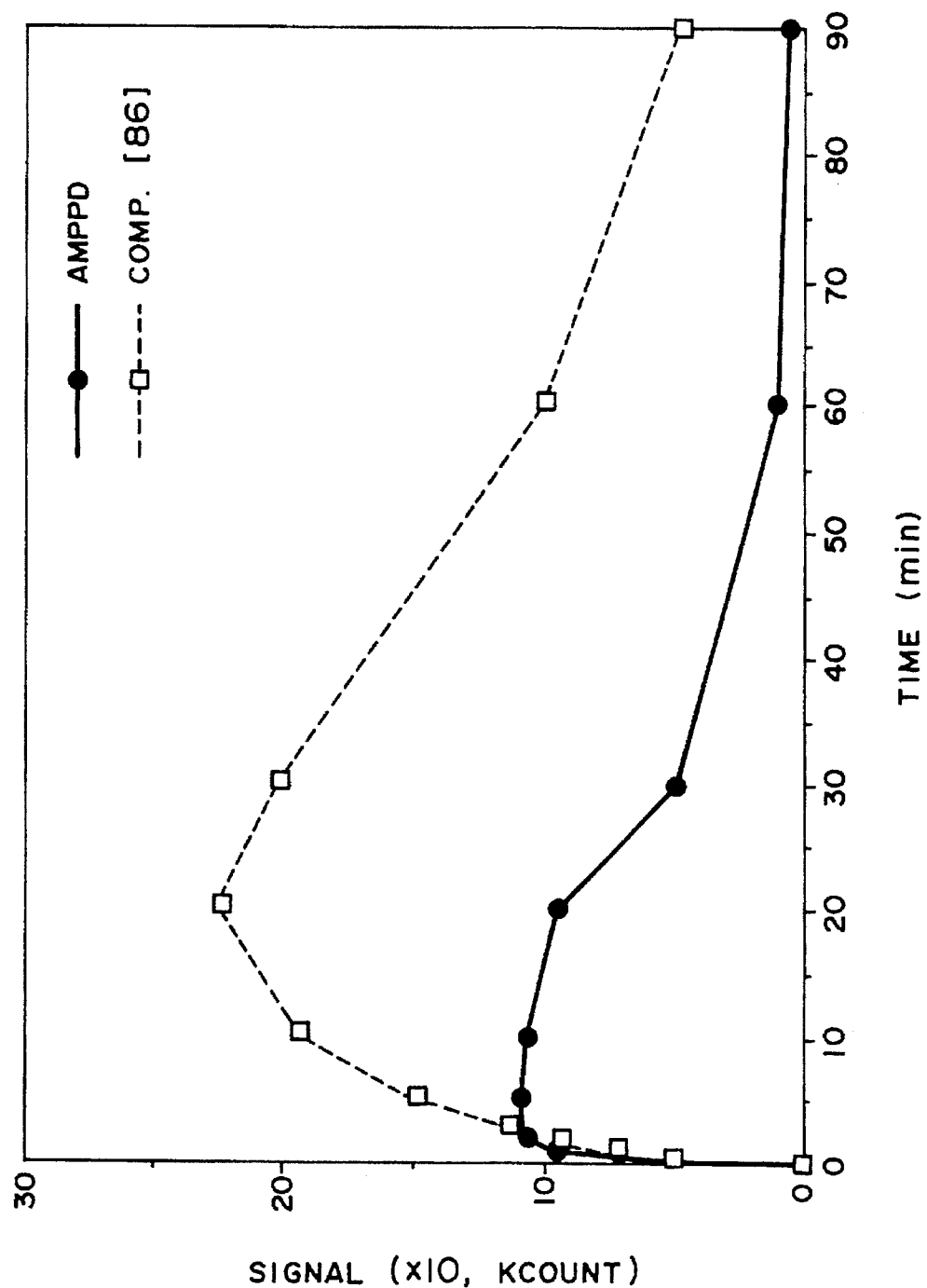
FIG. 2 is a graph showing the chemiluminescence of 3-t-butyl-4-methoxy-3-neopentyloxymethyl-4-(3'-phosphoryloxy)phenyl-1,2-dioxetane disodium salt (Compound [86]) synthesized in Example 66 in comparison with the chemiluminescence of the commercially available AMPPD.

The results are shown in FIG. 2.

Test Example 2-2

1 mg of 3-t-butyl-4-methoxy-3-neopentyloxymethyl-4-(3'-phosphoryloxy)phenyl-1,2-dioxetane disodium salt (Compound [86]) synthesized in Example 66 was dissolved in methanol-$d_4$ (0.35 ml), and the solution was heated at 60° C. in a thermostated bath, so that the solution was subjected to $^1$HNMR measurement at intervals of 2 to 3 hours.

From the results of the $^1$HNMR measurement, the half-life of Compound [86] at 60° C. was calculated to be 18.6 hours.

According to Test Example 1-2, the half-life of AMPPD at 60° was 5.5 hours under the same conditions as mentioned above.

The above results of Test Example 1-1to 2-2 indicate that the 1,2-dioxetane derivatives (Compounds [40] and [86]) of the present invention are thermally more stable and have chemiluminescence with higher intensity than the conventionally employed AMPPD (3-(2'-spiroadamantan)-4-methoxy-4-(3"-phosphoryloxy)phenyl-1,2-dioxetane disodium salt).

What is claimed is:

1. A 1,2-dioxetane derivative of formula (I):

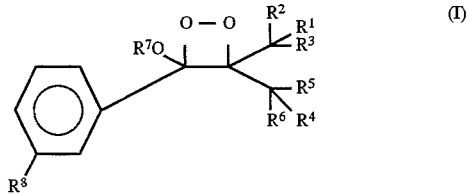

(I)

wherein $R^1$ and $R^4$ each represent, individually, hydrogen, an alkyl group, an alkoxyl group, a hydroxyl group, or —OSi($R^9R^{10}R^{11}$) in which $R^9$, $R^{10}$ and $R^{11}$ each represent an alkyl group; $R^2$, $R^3$, $R^5$ and $R^6$ each represent, individually, hydrogen or an alkyl group, provided that $R^2$, $R^3$, $R^5$ and $R^6$ each cannot be hydrogen at the same time, and that $R^2$ and $R^3$, and $R^5$ and $R^6$, each taken together, can form a cycloalkyl group; $R^7$ represents an alkyl group; $R^8$ represents hydrogen, an alkoxyl group, a phosphate salt group, or —OSi($R^9R^{10}R^{11}$).

2. The 1,2-dioxetane derivative as claimed in Claim 1, wherein at least one of $R^1$ or $R^4$ is a hydroxyl group, an alkoxyl group or —OSi($R^9R^{10}R^{11}$) in which $R^9$, $R^{10}$ $R^{11}$ each represent an alkyl group.

3. The 1,2dioxetane derivative as claimed in claim 1, wherein $R^1$ and $R^4$ are each hydrogen or an alkyl group; and $R^2$, $R^3$, $R^5$ and $R^6$ are each an alkyl group.

4. The 1,2-dioxetane derivative as claimed in claim 1, wherein $R^1$ and $R^4$ are each hydrogen or an alkyl group; and $R^2$ and $R^3$, and $R^5$ and $R^6$, each taken together, can form a cycloalkyl group.

* * * * *